(12) United States Patent
Taracido et al.

(10) Patent No.: US 8,685,993 B2
(45) Date of Patent: Apr. 1, 2014

(54) BI-HETEROARYL COMPOUNDS AS VPS34 INHIBITORS

(75) Inventors: Ivan Cornella Taracido, Somerville, MA (US); Edmund Martin Harrington, Plymouth, MA (US); Ayako Honda, Quincy, MA (US); Erin Keaney, Belmont, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/995,889

(22) PCT Filed: Dec. 19, 2011

(86) PCT No.: PCT/IB2011/055772
§ 371 (c)(1),
(2), (4) Date: Sep. 4, 2013

(87) PCT Pub. No.: WO2012/085815
PCT Pub. Date: Jun. 28, 2012

(65) Prior Publication Data
US 2013/0338159 A1 Dec. 19, 2013

Related U.S. Application Data

(60) Provisional application No. 61/425,416, filed on Dec. 21, 2010.

(51) Int. Cl.
*A01N 43/54* (2006.01)
*A61K 31/505* (2006.01)

(52) U.S. Cl.
USPC .......................... 514/275; 544/275

(58) Field of Classification Search
USPC .......................... 544/296; 514/275
See application file for complete search history.

(56) References Cited

U.S. PATENT DOCUMENTS

2009/0163463 A1 6/2009 Bruce et al.

FOREIGN PATENT DOCUMENTS

| WO | 97/33883 A1 | 9/1997 |
|---|---|---|
| WO | 02/22608 A1 | 3/2002 |
| WO | 2005/035507 A2 | 4/2005 |
| WO | WO 2005035507 A2 * | 4/2005 |
| WO | 2005/040133 A1 | 5/2005 |
| WO | 2005/040155 A1 | 5/2005 |
| WO | 2006/099231 A1 | 9/2006 |
| WO | 2006/127588 A2 | 11/2006 |
| WO | 2007/084786 A1 | 7/2007 |
| WO | 2008/098058 A1 | 8/2008 |
| WO | 2009/019656 A1 | 2/2009 |
| WO | 2010/068863 A2 | 6/2010 |
| WO | 2010/151747 A1 | 12/2010 |

OTHER PUBLICATIONS

Backer, Jonathan M., "The regulation and function of Class III PI3Ks: novel roles for Vps34", Biochemical Journal, vol. 410, No. 1, pp. 1-17, 2008.

* cited by examiner

*Primary Examiner* — James O Wilson
*Assistant Examiner* — Alexander R Pagano
(74) *Attorney, Agent, or Firm* — Laura K. Madden

(57) ABSTRACT

The present invention includes novel methods of treating a disease or disorder characterized by hyperactivity of Vps34, and compound as Vps34 inhibitors; particularly compounds of Formula I or a pharmaceutically acceptable salt thereof, as well as methods of treating a disease, disorder, or syndrome associated with Vps34 inhibition, particularly hyperproliferative diseases. The present invention also includes pharmaceutical compositions including compounds of formula I and pharmaceutically acceptable salts thereof.

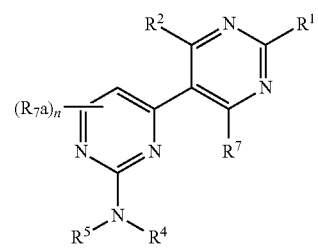

19 Claims, No Drawings

BI-HETEROARYL COMPOUNDS AS VPS34 INHIBITORS

FIELD OF INVENTION

The present invention relates to bi-hetereoaryl compounds that inhibit the Vps34 enzyme and uses thereof for the treatment of diseases associated with such inhibition. Consequently, the present invention includes bi-heteroaryl compounds, compositions thereof, methods of their use, and methods of their manufacture, where such compounds are generally pharmacologically useful in therapies whose mechanism of action rely on the inhibition of Vps34, and more particularly in therapies for the treatment of proliferative diseases, including cancer.

BACKGROUND

Phosphoinositide 3-kinases (hereafter, "PI3Ks") are enzymes that phosphorylate the 3-hydroxyl position of the inositol ring of phosphoinositides ("PIs"), and are involved in diverse cellular events such as cell migration, cell proliferation, oncogenic transformation, cell survival, signal transduction, and intracellular trafficking of proteins. In yeast (*S. cerevisiae*), Vps34 ("vacuolar protein sorting 34") encodes a PI 3-kinase gene product that mediates the active diversion of proteins from the secretory pathway to vacuoles; mammals have a corresponding family of PI3-kinases, including three classes of PI3Ks, with a variety of isoforms and types within. The closest human homolog of yeast Vps34 is an 887 residue protein called PI3Kclass3 ("PI3KC3")(also referred to herein as "hVps34," for human Vps34), which shares about 37% sequence identity with the yeast protein over its full length (Volinia et al. (1995) EMBO J. 14(14): 3339).

hVps34 is the enzymatic component of a multiprotein complex that includes a ser/thr kinase called Vps15p, and proautophagic tumor suppressors Beclin1/Atg6, and UVRAG, and Bif-1 in mammals (Vps15, Atg6, and Atg 14 in yeast)(Mari et al. (2007) Cell Biol. 9:1125). Of the three classes of PI3 kinase this has the most restricted substrate specificity, being strictly limited to PtdIns. Like class IA PI3-kinases, PI3KC3s (e.g., hVps34) play a well recognized role in the regulation of S6K1, and hence in nutrient-sensing.

The Vps34 gene product (Vps34p) is an enzyme required for protein sorting to the lysosome-like vacuole of the yeast, and appears to regulate intracellular protein trafficking decisions. Vps34p shares significant sequence similarity with the catalytic subunit of bovine phosphatidylinositol (PI) 3-kinase (the p110 subunit), which is known to interact with activated cell surface receptor tyrosine kinases. Yeast strains deleted for the Vps34 gene or carrying Vps34 point mutations lacked detectable PI 3-kinase activity and exhibited severe defects in vacuolar protein sorting. Overexpression of Vps34p resulted in an increase in PI 3-kinase activity, and this activity was specifically precipitated with antisera to Vps34p (Schu et al. (1993) Science 260 (5104): 88). hVps34 is an integral part of the autophagy process, or eukaryotic cell mechanism for cytoplasmic renewal. Autophagy is a cellular catabolic degradation response to starvation or stress whereby cellular proteins, organelles, and cytoplasm are engulfed, digested, and recycled to sustain cellular metabolism. Autophagy is characterized by the engulfment of cytoplasmic material into specialized double-membrane vesicles known as autophagosomes. The degradation of cellular cytoplasmic components helps eukaryotic cells jettison defective organelles and protein complexes (Yorimitsu et al (2005) Cell Death Differ. 12:1542). Nonselective autophagy can be initiated by starvation, allowing cells to convert organelles and proteins into nutrients for survival. Autophagy can also be employed to kill cells, in addition to or instead of apoptosis, for instance (Neufeld et al (2008) Autophagy).

Parodoxically, certain pathologies feature autophagy processes, such as tumorigenesis, aging, and neurodegeneration (Huang et al. (2007) Cell Cycle 6:1837). Cell death resulting from progressive cellular consumption has been attributed to unmitigated autophagy (Baehrecke et al. (2005) Nature Rev. Mol. Cell. Biol. 6:505). Autophagy is thought to prolong the survival of tumor cells defective in apoptosis, e.g., protecting them from metabolic stress. Inhibiting autophagy, and thereby sensitizing cells (e.g., apoptosis-resistant cells) to metabolic stress represents a promising tumor therapy regimen (Mathew et al. (2007) Nature Reviews 7:961). Known inhibitors of autophagy, including Wortmannin and 3-methyladenine, target and inhibit hVps34 (Petiot et al. (2000) J. Biol. Chem. 275:992).

Consistent with the autophagy and cancer link is recognition in the field that constitutive activation of PI3Ks is responsible for at least ovarian, head and neck, urinary tract, cervical and small cell lung cancers. PI3K signaling can be attenuated by the phosphatase activity of the tumor suppressor PTEN (phosphatase and tensin homologue detected in chromosome 10), which is absent in a number of human cancers. Inhibiting PI3K arrests a major cancer cell survival signaling pathway and overcomes the absence of tumor suppressor PTEN, providing antitumor activity and increased tumor sensitivity to a wide variety of drugs (Stein et al. (2001) Endocrine-Related Cancer 8:237).

SUMMARY

Compounds of formula (I), or a pharmaceutically acceptable salt thereof, are provided herein:

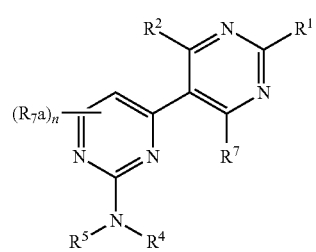

wherein $R^1$ is $C_{1-6}$alkyl, $NR^3R^6$, $C_{1-6}$alkoxy, or —S—$C_{1-6}$alkyl;

$R^2$ is $C_{1-6}$alkyl, $C_{2-6}$alkenyl, $C_{2-6}$alkynyl, a $C_{6-14}$aryl group, a $C_{3-14}$cycloalkyl group, a 5 to –14 membered heteroaryl containing 1 to 3 heteroatoms each independently selected from N, O, and S, $C_{1-6}$alkoxy, $C_{2-6}$-alkenyloxy, $C_{2-6}$-alkynyloxy, $C_{1-6}$alkyl-O—$R^{27}$, $C_{1-6}$alkyl-$C_{3-14}$cycloalkyl, $C_{1-6}$alkyl-O—$C_{0-6}$alkyl-$C_{6-14}$aryl, $C_{1-6}$alkyl-O—SiR$^8$R$^9$R$^{10}$, halogen, or $C_{1-6}$haloalkyl, wherein $R^2$ may be unsubstituted or substituted with OH, C1-6alkoxy, or halogen;

$R^4$ and $R^5$ are each independently H, $C_{1-6}$alkyl, $C_{2-6}$alkenyl, $C_{2-6}$alkynyl, $C_{6-14}$aryl, $C_{3-14}$cycloalkyl, a 3 to 14-membered cycloheteroalkyl containing 1 to 3 heteroatoms each independently selected from N, O, and S, a 5 to –14 membered heteroaryl containing 1 to 3 heteroatoms each independently selected from N, O, and S, $C_{1-6}$alkoxy, OH, $C_{1-6}$alkylNR$^{11}$R$^{12}$, $C_{1-6}$alkyl-O—R$^{13}$, $C_{1-6}$alkyl-5 to 14-membered heteroaryl containing 1 to 3 heteroatoms each independently selected from N, O, and S, or C(O)—$C_{1-6}$ alkyl, wherein said $C_{1-6}$alkyl, $C_{2-6}$alkenyl, $C_{2-6}$alkynyl, $C_{6-14}$aryl group, $C_{3-14}$cycloalkyl group, 3 to 14-membered cycloheteroalkyl group, 5- to 14-membered heteroaryl group, $C_{1-6}$alkoxy, $C_{1-6}$alkyl-$NR^{11}R^{12}$, $C_{1-6}$alkyl$OR^{13}$, $C_{1-6}$alkyl-5- to 14-membered heteroaryl group, or C(O)—$C_{1-6}$alkyl is optionally substituted by one or more substituents selected from the group consisting of halogen, a 5- to 14-membered heteroaryl containing 1 to 3 heteroaroms each independently selected from O, N, and S, —OH, $C_{1-6}$alkyl, $C_{1-6}$haloalkyl, —$C_{1-6}$alkyl$OR^{27}$, $C_{1-6}$alkoxy, —$NR^{14}R^{15}$, —$C(O)NR^{16}R^{17}$, —$NR^{18}C(O)R^{19}$, —$NR^{20}C(O)OR^{21}$, —$C(O)R^{22}$, —$C(O)OR^{23}$, —CN, —$SO_2R^{26}$, —O—, and —$NR^{24}SO_2R^{25}$;

$R^3$ and $R^6$ are independently H, $C_{1-6}$alkyl, $C_{1-6}$alkyl-$C_{6-14}$ aryl, $C_{1-6}$alkoxy, a $C_{3-14}$cycloalkyl, a 3- to 14-membered cycloheteroalkyl containing 1 to 3 heteroatoms each independently selected from O, N and S, a $C_{6-14}$aryl, a 5- to 14-membered heteroaryl containing 1 to 3 heteroatoms each independently selected from O, N, or S, or $C_{1-6}$alkyl-O—$R^8$, wherein $C_{1-6}$alkyl, $C_{1-6}$alkyl-$C_{6-14}$aryl, $C_{1-6}$alkoxy, a $C_{3-14}$cycloalkyl group, a 3- to 14-membered cycloheteroalkyl group, a $C_{6-14}$aryl group, a 5- to 14-membered heteroaryl group, or —$C_{1-6}$alkyl-O—$R^8$, may be substituted by one of more of $C_{1-6}$alkyl, and OH;

$R^{11}$ and $R^{12}$ are each independently hydrogen, $C_{1-6}$alkyl, $C_{3-8}$cycloalkyl, $C_{6-14}$ aryl, 5- to 14-membered heteroaryl containing 1 to 3 heteroatoms each independently selected from O, N or S, 3- to 14-membered cycloheteroalkyl containing 1 to 3 heteroatoms each independently selected from O, N, or S, or $NR^{11}R^{12}$ forms a non-aromatic four to seven membered ring optionally containing a second heteroatom selected from O, N and S, and optionally substituted by one or more substituents $R^{28}$ (preferably mono or di-substituted).

$R^7$ and $R^{7a}$ are independently H, $C_{1-6}$alkyl, halogen, OH, or $C_{1-6}$alkoxy.

n is 0, 1, or 2; and $R^8$, $R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are each independently H, $C_{1-6}$alkyl, $C_{2-6}$alkenyl, $C_{2-6}$alkynyl, $C_{6-14}$ aryl, $C_{3-14}$ cycloalkyl, 3- to 14-membered cycloheteroalkyl containing 1 to 3 heteroatoms selected from O, N or S, or a 5- to 14-membered heteroaryl containing 1 to 3 heteroatoms selected from O, N, or S.

The following specific embodiments of the invention according to formula (I) may be incorporated into the definition of formula (I) and combined in any number of suitable ways.

In an embodiment, $R^7$ and $R^{7a}$ are H or $C_{1-6}$alkyl, such as methyl, ethyl, propyl, or butyl. In another embodiment, $R^7$ is H or methyl, and in yet another embodiment, $R^7$ is H. In an embodiment, n is 0 or 1. In another embodiment, n is 0.

In an embodiment, $R^1$ is $C_{1-6}$alkyl, such as methyl, ethyl, or propyl; $C_{1-6}$alkoxy, such as methoxy, or ethoxy; —S—$C_{1-6}$alkyl, such as —$SCH_3$, or —$SCH_2CH_3$, or —$NR^3R^6$, where $R^3$ and $R^6$ are independently H, or $C_{1-6}$alkyl, such as methyl, ethyl, propyl, isopropyl, butyl, or pentyl; $C_{1-6}$alkyl-aryl, such as benzyl or ethyl-phenyl; $C_{1-6}$alkoxy, such as methoxy or ethoxy; a $C_{3-14}$cycloalkyl group (e.g., cyclopropyl, cyclopentyl, or cyclohexyl); a 3- to 14-membered cycloheteroalkyl containing 1 to 3 heteroatoms selected from O, S or N (e.g., moprholinyl, tetrahydropyranyl, tetrahydrofuranyl, piperidinyl, or piperazinyl); a $C_{6-14}$aryl group (e.g., phenyl); a 5- to 14-membered heteroaryl containing 1 to 3 heteroatoms selected from O, S or N (e.g., pyridinyl, pyrazinyl, or pyrimidyl); or —$C_{1-6}$alkyl-O—$R^8$, where $R^8$ is H or $C_{1-6}$alkyl (e.g., —$CH_2$—OH, —$CH_2CH_2$—OH, —$CH_2CH_2OH$, —CH $(CH_3)CH_2$—OH, —$CH_2CH(CH_3)$—OH), —$CH_2OCH_3$, —$CH_2CH_2$—O—$CH_3$, and so on).

In another embodiment, $R^1$ is methyl, ethyl, propyl, methoxy, ethoxy, methyl-phenyl, $NH_2$, NH—($C_5$-alkyl)-OH, —$NHCH_3$, —NH—$CH_2CH_2(CH_3)$, —$NHCH_2CH(CH_3)_2$, —NH($C_4$-alkyl)-OH, or —NH($C_4$-alkyl). In another embodiment, $R^1$ is $NH_2$, —NH—($C_5$-alkyl)-OH, —NH($C_4$-alkyl), —$NHCH_3$, or —$NHCH_2CH_2(CH_3)$.

In another embodiment, one of $R^3$ or $R^6$ is H, and the other may be $C_{1-6}$alkyl, such as methyl, ethyl, propyl, isopropyl, or butyl; $C_{1-6}$alkyl-aryl, such as benzyl, alpha-phenethyl, or beta-phenmethyl-phenyl; $C_{1-6}$alkoxy, such as methoxy or ethoxy; a $C_{3-14}$cycloalkyl, such as cyclopropyl, cyclopentyl, or cyclohexyl; a 3-14 membered cycloheteroalkyl, such as moprholinyl, tetrahydropyranyl, tetrahydrofuranyl, piperidinyl, or piperazinyl; a $C_{6-14}$aryl, such as phenyl; a 5-14 membered heteroaryl, such as pyridinyl, pyrazinyl, or pyrimidyl; or —$C_{1-6}$alkyl-O—$R^8$, where $R^8$ is H or $C_{1-6}$alkyl, (e.g., —$CH_2$OH, —$CH_2CH_2$OH, —$CH(CH_3)$OH, —$CH_2$—O—$CH_3$, or —$CH_2CH_2$—O—$CH_3$). In another embodiment, one of $R^3$ or $R^6$ is H, and the other is hydroxymethylene, hydroxyethylene (e.g., 1-hydroxyethyl or 2-hydroxyethyl), hydroxypropyl (e.g., 1-hydroxypropyl, 2-hydroxypropyl, 3-hydroxypropyl, or 1-hydroxy-1-methylethyl), hydroxybutyl (e.g., 1-hydroxybutyl, 2-hydroxybutyl, 3-hydroxybutyl, 4-hydroxybutyl, 1-hydroxy-1-methyl-propyl, 1-hydroxy-2,2-dimethyl-ethyl, or 2-hydroxy-1,1-dimethyl-ethyl). In another embodiment, both $R^3$ and $R^6$ are H.

In another embodiment, $R^2$ is $C_{1-6}$alkyl, such as methyl, ethyl, propyl, or butyl; $C_{2-6}$alkenyl, ethenyl, propenyl; $C_{2-6}$alkynyl, a $C_{6-14}$aryl group, such as phenyl; a $C_{3-14}$cycloalkyl group, such as cyclopropyl, cyclopentyl, or cyclohexyl; $C_{1-6}$alkoxy, such methoxy, or ethoxy; $C_{2-6}$-alkenyloxy, $C_{2-6}$-alkynyloxy, —$C_{1-6}$alkyl-O—$R^{27}$, where $R^{27}$ is H or $C_{1-6}$alkyl (e.g., —$CH_2$—O—$CH_3$, or —$CH_2CH_2$—O—$CH_3$, or $CH_2CH_2$—O—$CH_2CH_3$); $C_{1-6}$alkyl-$C_{3-14}$cycloalkyl (e.g., $CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, or —$CH_2CH_2$-cyclohexyl); —$C_{1-6}$alkyl-O—$C_{0-6}$alkyl-$C_{6-14}$ aryl (e.g., —$CH_2$—O—$CH_2$-phenyl, —$CH_2CH_2$—O—$CH_2$-phenyl, —$CH_2$—O—$CH_2CH_2$-phenyl, or —$CH_2CH_2$—O—$CH_2CH_2$-phenyl); $C_{1-6}$alkyl-O—$SiR^8R^9R^{10}$, where $R^8$, $R^9$, and $R^{10}$ are each independently H, $C_{1-6}$alkyl, $C_{6-14}$aryl, or a $C_{3-14}$cycloalkyl; or $C_{1-6}$haloalkyl (e.g, trifluoromethyl).

In another embodiment, $R^2$ is methyl, ethyl, propyl, ethenyl, propenyl, phenyl, cyclopropyl, cyclopentyl, cyclohexyl, methoxy, —$CH_2$—O—$CH_3$, —$CH_2CH_2$—O—$CH_3$, —$CH_2CH_2$—O—$CH_2CH_3$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, —$CH_2CH_2$-cyclohexyl, —$CH_2$—O—$CH_2$-phenyl, —$CH_2CH_2$—O—$CH_2$-phenyl, —$CH_2$—O—$CH_2CH_2$-phenyl, —$CH_2CH_2$—O—$CH_2CH_2$-phenyl, trifluoromethyl, or —$C_{1-6}$alkyl-O—$SiR^8R^9R^{10}$, where $R^8$, $R^9$, and $R^{10}$ are each independently H, methyl, ethyl, or propyl, phenyl, cyclopropyl, cyclopentyl, or cyclohexyl.

In a further embodiment, $R^2$ is methyl, ethyl, propyl, phenyl, cyclopropyl, cyclopentyl, cyclohexyl, methoxy, —$CH_2$—O—$CH_3$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, —$CH_2CH_2$-cyclohexyl, or —$CH_2$—O—$CH_2$-phenyl. In yet another embodiment, $R^2$ is methyl, ethyl, propyl, phenyl, cyclopropyl, methoxy, —$CH_2$—O—$CH_3$, —$CH_2$-cyclopropyl, —$CH_2$-cyclobutyl, —$CH_2$-cyclopentyl, —$CH_2$-cyclohexyl, or —CH$_2$CH$_2$-cyclopropyl. In yet another embodiment R$^2$ is —CH$_2$-cyclopropyl.

In another embodiment, R$^4$ and R$^5$ are each independently H, C$_{1-6}$alkyl, C$_{2-6}$alkenyl, C$_{2-6}$alkynyl, a C$_{6-14}$aryl, a C$_{3-14}$cycloalkyl, a 3- to 14-membered cycloheteroalkyl, a 5- to 14-membered heteroaryl group, C$_{1-6}$alkoxy, OH, —C$_{1-6}$alkylNR$^{11}$R$^{12}$, —C$_{1-6}$alkyl-O—R$^{13}$, C$_{1-6}$alkyl-5- to 14-membered heteroaryl group containing 1 to 3 heteroatoms each independently selected from O, N or S, or C(O)—C$_{1-6}$ alkyl, wherein R$^4$ or R$^5$ may be unsubstituted or substituted by substituents as iterated below.

In an embodiment, R$^{11}$, R$^{12}$, and R$^{13}$ are each independently H, C$_{1-6}$alkyl, C$_{2-6}$alkenyl, C$_{2-6}$alkynyl, a C$_{6-14}$ aryl, a C$_{3-14}$ cycloalkyl group, a 3- to 14-membered cycloheteroalkyl containing 1 to 3 heteroatoms each independently selected from O, N or S, or a 5-14 membered heteroaryl containing 1 to 3 heteroatoms each independently selected from O, N or S.

In another embodiment, the present invention includes compounds of Formula (I) where R$^4$ and R$^5$ are each independently H, a C$_{6-14}$aryl, C$_{3-14}$cycloalkyl, a 3- to 14-membered cycloheteroalkyl containing 1 to 3 heteroatoms each independently selected from O, N or S, or a 5-14 membered heteroaryl containing 1 to 3 heteroatoms each independently selected from O, N or S, wherein said C$_{6-14}$aryl, C$_{3-14}$cycloalkyl, 3- to 14-membered cycloheteroalkyl, or 5- to 14-membered heteroaryl is optionally mono- or di-substituted by substituents selected from the group consisting of halogen, OH, C$_{1-6}$alkyl, C$_{1-6}$haloalkyl, —C$_{1-6}$alkylOH, C$_{1-6}$alkoxy, —NR$^{14}$R$^{15}$, —C(O)ONR$^{16}$R$^{17}$, —NR$^{18}$C(O)R$^{19}$, —NR$^{20}$C(O)OOR$^{21}$, —C(O)R$^{22}$, —C(O)OR$^{23}$, and —NR$^{24}$SO$_2$R$^{25}$.

In another embodiment, R$^4$ is H, and R$^5$ is methyl, ethyl, propyl, phenyl, cyclopentyl, cyclohexyl, piperidinyl, piperazinyl, pyrrolidinyl, tetrahydropyranyl, pyridinyl, pyrimidinyl, or pyridazinyl; each of which may be unsubstituted or substituted with one or more of halogen, a 5- to 14 membered heteroaryl (preferably, pyridinyl); OH, C$_{1-6}$alkyl (preferably C$_{1-4}$alkyl; C$_{1-6}$haloalkyl (preferably, trifluoromethyl), C$_{1-6}$alkylOR$^{27}$, C$_{1-6}$alkoxy (preferably, methoxy, or ethoxy), —NR$^{14}$R$^{15}$, —C(O)NR$^{16}$R$^{17}$, —NR$^{18}$C(O)R$^{19}$, —NR$^{20}$C(O)OR$^{21}$, —C(O)R$^{22}$, —C(O)OR$^{23}$, —CN, —SO$_2$R$^{26}$, —O—, or —NR$^{24}$SO$_2$R$^{25}$.

In an embodiment, R$^{23}$, R$^{24}$, R$^{25}$, R$^{26}$, and R$^{27}$ are each independently H, C$_{1-6}$alkyl (preferably, C$_{1-4}$alkyl), C$_{2-6}$alkenyl, C$_{2-6}$alkynyl, a C$_{6-14}$ aryl (preferably, phenyl) C$_{3-14}$ cycloalkyl (preferably, cyclopropyl, cyclopentyl, or cyclohexyl) 3- to 14-membered cycloheteroalkyl containing 1 to 3 heteroatoms each independently selected from O, N or S, or 5- to 14-membered heteroaryl containing 1 to 3 heteroatoms each independently selected from O, N or S.

In yet another embodiment, one of R$^4$ or R$^5$ is H, and the other is a moiety selected from methyl, ethyl, propyl, phenyl, cyclopentyl, cyclohexyl, piperidinyl, piperazinyl, pyrrolidinyl, tetrahydropyranyl, pyridinyl, pyrimidinyl, or pyridazinyl; wherein said moiety is optionally with one to two substituents each independently selected from the group consisting of F, Cl, pyridinyl, OH, methyl, ethyl, trifluoromethyl, 1-hydroxyethyl, 2-hydroxyethyl, —C(O)OH, —NHC(O)O-isopropyl, —NH$_2$, —NHSO$_2$CH$_3$, —SO$_2$CH$_3$, —CN, or —NHC(O)CH$_3$. In another embodiment, R$^4$ is H, and R$^5$ is methyl, ethyl, phenyl, or piperidinyl, wherein said methyl, said ethyl, said phenyl and said piperidinyl groups are optionally substituted with one or more substituents each independently selected from —OH, —CN, Cl, or F.

In another embodiment, one of R$^4$ and R$^5$ is H, and the other is phenyl or pyridinyl, wherein said phenyl and said pyridinyl are optionally substituted with one or more substitutents selected from F, Cl, OH, methyl, ethyl, CN, or CF$_3$.

In another embodiment, the present invention includes compounds of Formula II:

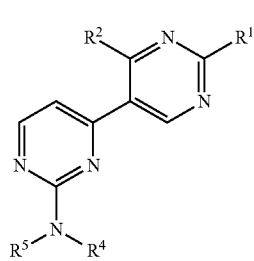

or a pharmaceutically acceptable salt thereof, wherein
R$^1$ is (C$_1$-C$_6$)alkyl, —OCH$_3$, —NH$_2$, —NH(C$_1$-C$_6$)alkyl, —NHCH$_2$(phenyl), —NHCH$_2$CH$_2$OH, —NHCH$_2$CH(OH)CH$_3$, —NHCH(CH$_3$)CH$_2$OH, —NHCH$_2$CH(CH$_3$)$_2$OH, —NHCH$_2$CH$_2$OCH$_3$, —NH(C$_3$-C$_6$)cycloalkyl, phenethylamino-, tetrahydropyranylamino-, or —SCH$_3$;
R$^2$ is (C$_1$-C$_6$)alkyl, —CF$_3$, —CH$_2$(cyclopropyl), —CH$_2$OH, or —CH$_2$OCH$_2$(phenyl);
R$^4$ is H; and
R$^5$ is (i) —(CH$_2$)$_n$—R$^{5a}$, where n is 0, 1 or 2 and R$^{5a}$ is pyridinyl, 6-methoxypyridin-3-yl, furanyl, imidazolyl, isoxazolyl, thiazolyl, thiadiazolyl, quinolinyl, 1H-indolyl, benzo[d][1,3]dioxolyl, morpholinyl, tetrahydropyranyl, or piperidinyl, where said chemical moiety is optionally substituted with a methyl or halo; or (ii) (C$_1$-C$_6$)alkyl, (C$_3$-C$_6$)cycloalkyl, or phenyl, wherein said (C$_1$-C$_6$)alkyl, said (C$_3$-C$_6$)cycloalkyl, and said phenyl are optionally substituted with one to two substituents each independently selected from F, Cl, —CH$_3$, —CN, —OH, —OCH$_3$, —NHC(O)—(C$_1$-C$_4$)alkyl, —NH$_2$, —N(CH$_3$)$_2$, —NHSO$_2$CH$_3$, —C(O)CH$_3$, —C(O)OH, or —SO$_2$CH$_3$.

In one embodiment of the invention R$^5$ is (i). In another embodiment —(CH$_2$)$_n$—R$^{5a}$ wherein n is 0 or 1. In another embodiment n is 0.

In another embodiment R$^5$ is (ii).

In another embodiment, the present invention includes a method of inhibiting Vps34 activity in a subject, wherein the method comprises administering to the subject a therapeutically effective amount of the compound of formula (I) or its prodrug or pharmaceutical composition comprising the compound of formula I or its prodrug and pharmaceutically acceptable excipients to a subject in need thereof.

In an embodiment, disease, disorder, or syndrome is hyperproliferative in a subject, wherein said subject is an animal including humans, and the disease or disorder is selected from a group comprising cancer and inflammation. In another embodiment, the present invention includes the compound of formula (I) for use in therapy.

In another embodiment, the present invention includes a pharmaceutical composition comprising a compound of formula I and a pharmaceutically acceptable carrier or excipient. In another embodiment, the present invention includes a pharmaceutical composition comprising a compound of formula I in combination with a second active agent, and a pharmaceutically acceptable carrier or excipient.

In yet another embodiment, the present invention includes a method of treating a mammal comprising administration of a Vps34 inhibitor. In an embodiment, the invention includes administration of a Vps34 inhibitor, where the Vps34 inhibitor is a compound of formula I.

In still another embodiment of the present invention, the compound is a stereoisomer or a tautomer.

Representative compounds of the invention include:

(1r,4r)-4-(2'-amino-4'-(cyclopropylmethyl)-4,5'-bipyrimidin-2-ylamino)cyclohexanol;

(1r,4r)-4-(4'-(cyclopropylmethyl)-2'-(methylamino)-4,5'-bipyrimidin-2-ylamino)cyclohexanol;

4-(4'-(cyclopropylmethyl)-4,5'-bipyrimidin-2-ylamino)cyclohexanol;

$N^2$-cyclohexyl-4'-(cyclopropylmethyl)-$N^{2'}$-methyl-4,5'-bipyrimidine-2,2'-diamine;

4'-(cyclopropylmethyl)-$N^{2'}$-methyl-$N^2$-(1-methylpiperidin-4-yl)-4,5'-bipyrimidine-2,2'-diamine;

$N^2$-(3-aminopropyl)-4'-(cyclopropylmethyl)-$N^{2'}$-methyl-4,5'-bipyrimidine-2,2'-diamine;

4'-(cyclopropylmethyl)-$N^2$-(3,5-dimethoxyphenyl)-$N^{2'}$-methyl-4,5'-bipyrimidine-2,2'-diamine;

4'-(cyclopropylmethyl)-$N^2$-(3,4-dimethoxyphenyl)-$N^{2'}$-methyl-4,5'-bipyrimidine-2,2'-diamine;

4'-(cyclopropylmethyl)-$N^2$-(6-methoxypyridin-3-yl)-$N^{2'}$-methyl-4,5'-bipyrimidine-2,2'-diamine;

4'-(cyclopropylmethyl)-$N^{2'}$-methyl-$N^2$-phenyl-4,5'-bipyrimidine-2,2'-diamine;

4'-(cyclopropylmethyl)-$N^{2'}$-methyl-$N^2$-(pyridin-4-yl)-4,5'-bipyrimidine-2,2'-diamine;

4'-(cyclopropylmethyl)-$N^{2'}$-methyl-$N^2$-(quinolin-3-yl)-4,5'-bipyrimidine-2,2'-diamine;

$N^2$-cyclobutyl-4'-(cyclopropylmethyl)-$N^{2'}$-methyl-4,5'-bipyrimidine-2,2'-diamine;

4'-(cyclopropylmethyl)-$N^{2'}$-methyl-$N^2$-(tetrahydro-2H-pyran-4-yl)-4,5'-bipyrimidine-2,2'-diamine; $N^2$-cyclopentyl-4'-(cyclopropylmethyl)-$N^{2'}$-methyl-4,5'-bipyrimidine-2,2'-diamine;

tert-butyl (1r,4r)-4-(4'-(cyclopropylmethyl)-2'-(methylamino)-4,5'-bipyrimidin-2-ylamino)cyclohexylcarbamate;

$N^2$-(4-aminocyclohexyl)-4'-(cyclopropylmethyl)-$N^{2'}$-methyl-4,5'-bipyrimidine-2,2'-diamine;

4'-(cyclopropylmethyl)-$N^{2'}$-methyl-$N^2$-(pyridin-3-yl)-4,5'-bipyrimidine-2,2'-diamine;

4'-(cyclopropylmethyl)-$N^2$-(4-methoxyphenyl)-$N^{2'}$-methyl-4,5'-bipyrimidine-2,2'-diamine;

(1r,4r)-4-(4'-(cyclopropylmethyl)-2'-(methylamino)-4,5'-bipyrimidin-2-ylamino)cyclohexanecarboxylic acid;

4'-(cyclopropylmethyl)-$N^2$-((1r,4r)-4-methoxycyclohexyl)-$N^{2'}$-methyl-4,5'-bipyrimidine-2,2'-diamine;

(1r,4r)-4-(4'-(cyclopropylmethyl)-2'-ethyl-4,5'-bipyrimidin-2-ylamino)cyclohexanol;

4-(4'-(cyclopropylmethyl)-2'-(methylamino)-4,5'-bipyrimidin-2-ylamino)cyclohexanol;

(1r,4r)-4-(4'-(cyclopropylmethyl)-2'-methyl-4,5'-bipyrimidin-2-ylamino)cyclohexanol;

4-(4'-(cyclopropylmethyl)-2'-methoxy-4,5'-bipyrimidin-2-ylamino)cyclohexanol;

4'-(cyclopropylmethyl)-2'-methoxy-N-(pyridin-4-yl)-4,5'-bipyrimidin-2-amine;

4'-(cyclopropylmethyl)-$N^2$-(pyridin-4-yl)-4,5'-bipyrimidine-2,2'-diamine;

4'-(cyclopropylmethyl)-2'-(methylthio)-N-(pyridin-4-yl)-4,5'-bipyrimidin-2-amine;

$N^{2'}$-cyclopropyl-4'-(cyclopropylmethyl)-$N^2$-(pyridin-4-yl)-4,5'-bipyrimidine-2,2'-diamine;

4'-(cyclopropylmethyl)-$N^{2'}$-isopropyl-$N^2$-(pyridin-4-yl)-4,5'-bipyrimidine-2,2'-diamine;

$N^{2'}$-cyclohexyl-4'-(cyclopropylmethyl)-$N^2$-(pyridin-4-yl)-4,5'-bipyrimidine-2,2'-diamine;

$N^{2'}$-benzyl-4'-(cyclopropylmethyl)-$N^2$-(pyridin-4-yl)-4,5'-bipyrimidine-2,2'-diamine;

4'-(cyclopropylmethyl)-$N^{2'}$-isobutyl-$N^2$-(pyridin-4-yl)-4,5'-bipyrimidine-2,2'-diamine;

$N^{2'}$-cyclopentyl-4'-(cyclopropylmethyl)-$N^2$-(pyridin-4-yl)-4,5'-bipyrimidine-2,2'-diamine;

$N^{2'}$-cyclobutyl-4'-(cyclopropylmethyl)-$N^2$-(pyridin-4-yl)-4,5'-bipyrimidine-2,2'-diamine;

4'-(cyclopropylmethyl)-$N^2$-(pyridin-4-yl)-$N^{2'}$-(tetrahydro-2H-pyran-4-yl)-4,5'-bipyrimidine-2,2'-diamine;

(R)-4'-(cyclopropylmethyl)-$N^{2'}$-(1-phenylethyl)-$N^2$-(pyridin-4-yl)-4,5'-bipyrimidine-2,2'-diamine; $N^{2'}$-tert-butyl-4'-(cyclopropylmethyl)-$N^2$-(pyridin-4-yl)-4,5'-bipyrimidine-2,2'-diamine;

1-(4'-(cyclopropylmethyl)-2-(pyridin-4-ylamino)-4,5'-bipyrimidin-2'-ylamino)propan-2-ol;

4'-(cyclopropylmethyl)-$N^{2'}$-(2-methoxyethyl)-$N^2$-(pyridin-4-yl)-4,5'-bipyrimidine-2,2'-diamine;

2-(4'-(cyclopropylmethyl)-2-(pyridin-4-ylamino)-4,5'-bipyrimidin-2'-ylamino)propan-1-ol;

4'-(cyclopropylmethyl)-$N^{2'}$-neopentyl-$N^2$-(pyridin-4-yl)-4,5'-bipyrimidine-2,2'-diamine;

$N^{2'}$-sec-butyl-4'-(cyclopropylmethyl)-$N^2$-(pyridin-4-yl)-4,5'-bipyrimidine-2,2'-diamine;

4'-(cyclopropylmethyl)-$N^{2'}$-ethyl-$N^2$-(pyridin-4-yl)-4,5'-bipyrimidine-2,2'-diamine;

4'-(benzyloxymethyl)-$N^2$-(pyridin-4-yl)-4,5'-bipyrimidine-2,2'-diamine;

(2'-amino-2-(pyridin-4-ylamino)-4,5'-bipyrimidin-4'-yl)methanol;

4'-(cyclopropylmethyl)-$N^2$-(tetrahydro-2H-pyran-3-yl)-4,5'-bipyrimidine-2,2'-diamine;

4'-(cyclopropylmethyl)-$N^2$-(piperidin-4-yl)-4,5'-bipyrimidine-2,2'-diamine;

N-((1r,4r)-4-(2'-amino-4'-(cyclopropylmethyl)-4,5'-bipyrimidin-2-ylamino)cyclohexyl)acetamide;

N-((1r,4r)-4-(2'-amino-4'-(cyclopropylmethyl)-4,5'-bipyrimidin-2-ylamino)cyclohexyl)methanesulfonamide;

2-(4'-(cyclopropylmethyl)-2-(pyridin-4-ylamino)-4,5'-bipyrimidin-2'-ylamino)ethanol;

1-(4'-(cyclopropylmethyl)-2-(pyridin-4-ylamino)-4,5'-bipyrimidin-2'-ylamino)-2-methylpropan-2-ol;

(S)-1-(4'-(cyclopropylmethyl)-2-(pyridin-4-ylamino)-4,5'-bipyrimidin-2'-ylamino)propan-2-ol;

(R)-2-(4'-(cyclopropylmethyl)-2-(pyridin-4-ylamino)-4,5'-bipyrimidin-2'-ylamino)propan-1-ol;

(S)-2-(4'-(cyclopropylmethyl)-2-(pyridin-4-ylamino)-4,5'-bipyrimidin-2'-ylamino)propan-1-ol;

1-(4'-(cyclopropylmethyl)-2-(pyridin-4-ylamino)-4,5'-bipyrimidin-2'-ylamino)propan-2-ol;

4'-methyl-$N^2$-(pyridin-4-yl)-4,5'-bipyrimidine-2,2'-diamine;

N-((1r,4r)-4-(4'-(cyclopropylmethyl)-2'-(2-hydroxy-2-methylpropylamino)-4,5'-bipyrimidin-2-ylamino)cyclohexyl)methanesulfonamide;

4'-(cyclopropylmethyl)-$N^2$-(pyridin-2-yl)-4,5'-bipyrimidine-2,2'-diamine;

3-(2'-amino-4'-(cyclopropylmethyl)-4,5'-bipyrimidin-2-ylamino)-2,2-dimethylpropan-1-ol;

4'-(cyclopropylmethyl)-$N^2$-(3-methylisoxazol-5-yl)-4,5'-bipyrimidine-2,2'-diamine;

4'-(cyclopropylmethyl)-$N^2$-(1,3,4-thiadiazol-2-yl)-4,5'-bipyrimidine-2,2'-diamine;

4'-(cyclopropylmethyl)-N²-(4-fluorophenyl)-4,5'-bipyrimidine-2,2'-diamine;

4'-(cyclopropylmethyl)-N²-(furan-2-ylmethyl)-4,5'-bipyrimidine-2,2'-diamine;

4'-(cyclopropylmethyl)-N²-(1H-indol-5-yl)-4,5'-bipyrimidine-2,2'-diamine;

N²-(benzo[d][1,3]dioxol-5-yl)-4'-(cyclopropylmethyl)-4,5'-bipyrimidine-2,2'-diamine;

N²-(2-chloropyridin-4-yl)-4'-(cyclopropylmethyl)-4,5'-bipyrimidine-2,2'-diamine;

N-(4-(2'-amino-4'-(cyclopropylmethyl)-4,5'-bipyrimidin-2-ylamino)phenyl)acetamide;

N²-(4-chlorophenyl)-4'-(cyclopropylmethyl)-4,5'-bipyrimidine-2,2'-diamine;

N²-(2-(1H-indol-3-yl)ethyl)-4'-(cyclopropylmethyl)-4,5'-bipyrimidine-2,2'-diamine;

4'-(cyclopropylmethyl)-N²-(pyridin-3-ylmethyl)-4,5'-bipyrimidine-2,2'-diamine;

4'-(cyclopropylmethyl)-N²-(2-morpholinoethyl)-4,5'-bipyrimidine-2,2'-diamine;

N²-(2-(1H-imidazol-4-yl)ethyl)-4'-(cyclopropylmethyl)-4,5'-bipyrimidine-2,2'-diamine;

N²-(4-aminophenyl)-4'-(cyclopropylmethyl)-4,5'-bipyrimidine-2,2'-diamine;

N²-(5-chloropyridin-2-yl)-4'-(cyclopropylmethyl)-4,5'-bipyrimidine-2,2'-diamine;

4'-(cyclopropylmethyl)-N²-(2-methyl-1H-indol-5-yl)-4,5'-bipyrimidine-2,2'-diamine;

4-(2'-amino-4'-(cyclopropylmethyl)-4,5'-bipyrimidin-2-ylamino)benzonitrile;

4'-(cyclopropylmethyl)-N²-(3-(dimethylamino)phenyl)-4,5'-bipyrimidine-2,2'-diamine;

4'-(cyclopropylmethyl)-N-(pyridin-4-yl)-4,5'-bipyrimidin-2-amine;

N²-(4-fluorophenyl)-4'-methyl-4,5'-bipyrimidine-2,2'-diamine;

N²-(4-fluorophenyl)-4,5'-bipyrimidine-2,2'-diamine;

1-(2-(2-chloropyridin-4-ylamino)-4'-(cyclopropylmethyl)-4,5'-bipyrimidin-2'-ylamino)-2-methylpropan-2-ol;

4-(4'-(cyclopropylmethyl)-2'-(2-hydroxy-2-methylpropylamino)-4,5'-bipyrimidin-2-ylamino)benzonitrile;

1-(4'-(cyclopropylmethyl)-2-(4-fluorophenylamino)-4,5'-bipyrimidin-2'-ylamino)-2-methylpropan-2-ol;

1-(4'-(cyclopropylmethyl)-2-(4-(methylsulfonyl)phenylamino)-4,5'-bipyrimidin-2'-ylamino)-2-methylpropan-2-ol;

1-(2-(4-chlorophenylamino)-4'-(cyclopropylmethyl)-4,5'-bipyrimidin-2'-ylamino)-2-methylpropan-2-ol;

N-(4-(4'-(cyclopropylmethyl)-2'-(2-hydroxy-2-methylpropylamino)-4,5'-bipyrimidin-2-ylamino)phenyl)acetamide;

2-methyl-1-(2-(pyridin-4-ylamino)-4'-(trifluoromethyl)-4,5'-bipyrimidin-2'-ylamino)propan-2-ol;

N²-(pyridin-4-yl)-4'-(trifluoromethyl)-4,5'-bipyrimidine-2,2'-diamine;

4-(2'-(2-hydroxy-2-methylpropylamino)-4'-(trifluoromethyl)-4,5'-bipyrimidin-2-ylamino)benzonitrile;

4-(4'-ethyl-2'-(2-hydroxy-2-methylpropylamino)-4,5'-bipyrimidin-2-ylamino)benzonitrile; and 4-(2'-(2-hydroxy-2-methylpropylamino)-4'-phenyl-4,5'-bipyrimidin-2-ylamino)benzonitrile.

DEFINITIONS

As used herein, "alkyl" or "alkylene" refers to a straight chain or branched hydrocarbon from 1 to 20 carbon atoms. Alkyl moieties having from 1 to 5 carbons are referred to as "lower alkyl" and examples include, but are not limited to, methyl, ethyl, n-propyl, isopropyl, n-butyl, t-butyl, isobutyl, n-pentyl, iso-pentyl, neopentyl and.

"$C_{1-6}$-haloalkyl" refers to an alkyl group substituted by up to seven halogen groups, e.g. fluoro groups. For example, where the substituent is fluoro, common haloalkyl groups are trifluoroalkyl, 2,2,2-trifluoroethyl or 2,2,2,1,1-pentafluoroethyl groups.

The term "alkenyl" refers to a monovalent group derived from a hydrocarbon having at least one carbon-carbon double bond. The term "$C_2$-$C_6$-alkenyl" refers to a monovalent group derived from a hydrocarbon having two to six carbon atoms and comprising at least one carbon-carbon double bond.

The term "alkynyl" refers to a monovalent group derived from a hydrocarbon having at least one carbon-carbon triple bond. The term "$C_2$-$C_6$-alkynyl" refers to a monovalent group derived from a hydrocarbon having two to six carbon atoms and comprising at least one carbon-carbon triple bond.

The term "alkoxy" refers to a group in which an alkyl group is attached to oxygen, wherein alkyl is as previously defined.

"Cycloalkyl" or "cycloalkylene" refers to a 3-14 membered monocyclic or bicyclic carbocyclic ring, The cycloalkyl or cycloalklene may optionally include one to three ring members selected from —C(═O), —N($R^{29}$)q-, —O— and S(O)r where $R^{29}$ is H or $C_{1-6}$-alkyl, q is 0-1 and r is 0-2. The cycloalkyl may be attached using any of the ring members. Suitable cycloalkyl groups include cyclopropyl, cyclobutyl, cyclopentyl, cyclohexyl, cycloheptyl or cyclooctyl.

"Aryl" or "arylene" represents a 6-14 membered single or fused ring system, wherein at least one of the fused rings is aromatic and the other ring is another aromatic ring or a saturated or partially unsaturated cycloalkyl. The aryl may be attached using any of the ring members. Suitable aryl groups include phenyl, naphthyl, anthracyl and phenanthryl.

"Heteroaryl" or "heteroarylene" refers to a 5-14 membered monocyclic or fused ring system, wherein the monocyclic and at least one of the bicyclic fused rings is an aromatic ring comprising either (a) 1 to 4 nitrogen atoms, (b) one oxygen or one sulphur atom or (c) 1 oxygen atom or 1 sulphur atom and 1 or 2 nitrogen atoms, and the fused ring may be an aryl group, another heteroaryl, a saturated or partially unsaturated cycloalkyl, or a saturated or partially unsaturated heterocycle. The heteroaryl may optionally include one to three ring members selected from the group consisting of —C(O), —N($R^{31}$)q-, —O— and S(O)r where $R^{31}$ is H or $C_{1-6}$-alkyl, q is 0-1 and r is 0-2. The heteroaryl may be attached using any of the ring members. Suitable monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Suitable fused heteroaryl groups include indolyl, benzofuranyl, quinolyl, isoquinolyl indazolyl, indolinyl, isoindolyl, indolizinyl, benzamidazolyl, and quinolinyl "Cycloheteroalkyl" or "cycloheteroalkylene" or "heterocycle" refers to a 3-14 membered nonaromatic rings that are either partially or fully hydrogenated and may exist as a single ring, bicyclic ring or a spiral ring comprising one or two ring members selected from the group consisting of —N($R^{32}$)—, —O— and —S(O)$_r$—. The cycloheteroalkyl may optionally include one to three ring members selected from —C(═O), —N($R^{33}$)q-, —O— and S(O)r where $R^{32}$ or $R^{33}$ is H or $C_{1-6}$-alkyl, q is 0-1 and r is 0-2. The cycloheteroalkyl may be attached using any of the ring members. Suitable heterocycloalkyl groups include [1,3]dioxolane, [1,4]dioxane, oxiranyl, aziridinyl, oxetanyl, azetidinyl, tetrahydrofuranyl, pyrrolidinyl, tetrahydropyranyl, piperidinyl, morpholino, thiomorpholinyl, piperazinyl, azepinyl, oxapinyl, oxazepinyl and diazepinyl.

"Halogen" or "halo" may be fluorine, chlorine, bromine or iodine.

It is to be understood that the terminology C(O) refers to a —C═O group, whether it be ketone, aldehyde or acid or acid derivative. Similarly, S(O) refers to a —S═O group.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compounds of the present invention" (unless specifically identified otherwise) refer to compounds of Formula (I), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by the inhibition of Vps34.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Compounds of Formula I where $G^3$ is C—H, and $G^4$ and $G^5$ are both nitrogen can be prepared using the synthesis outlined below in Scheme I.

Scheme I

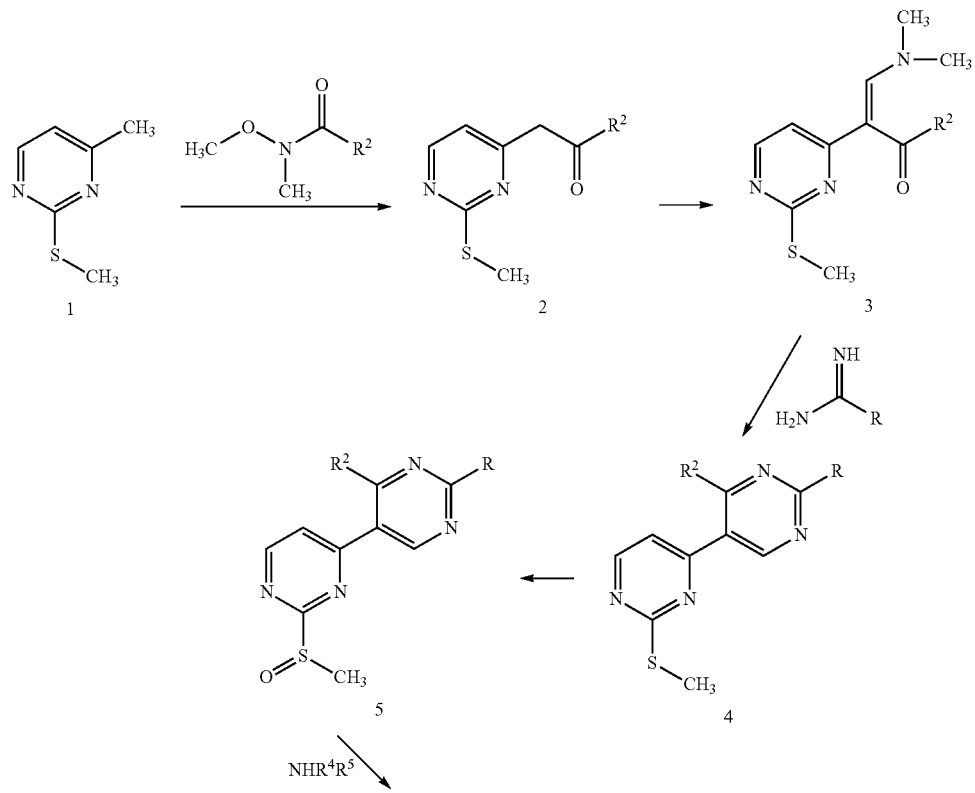

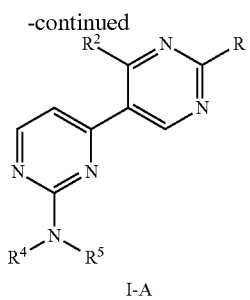

I-A

Generally, the compounds of formula I-A can be prepared according to Scheme 1, which contains five steps. As to the individual steps in the scheme above, step 1 involves the alkylation of commercially available 4-methyl-2-(methylthio)pyrimidine with R2 substituted Weinreb amides, or alternatively R2-substituted benzyl esters. Further reaction of ketones of formula 2 with N,N-dimethylformamide dimethyl acetal in the absence of solvent at 80° C. affords vinylogous amides 3. Intermediates of the formula 4a-f are prepared by cyclization of intermediate 3 with R-substituted guanidines at 120° C. in the presence of a base such as potassium carbonate. In step 4, the sulfide is converted to the sulfoxide or sulfone by reaction with a suitable oxidizing agent, such as m-Chloroperoxybenzoic acid. Conversion to final compounds I-A can be accomplished by reaction of intermediates 5 with aliphatic amines in the microwave at 160° C. or by addition of deprotonated aryl or heteroarylamines.

Scheme II

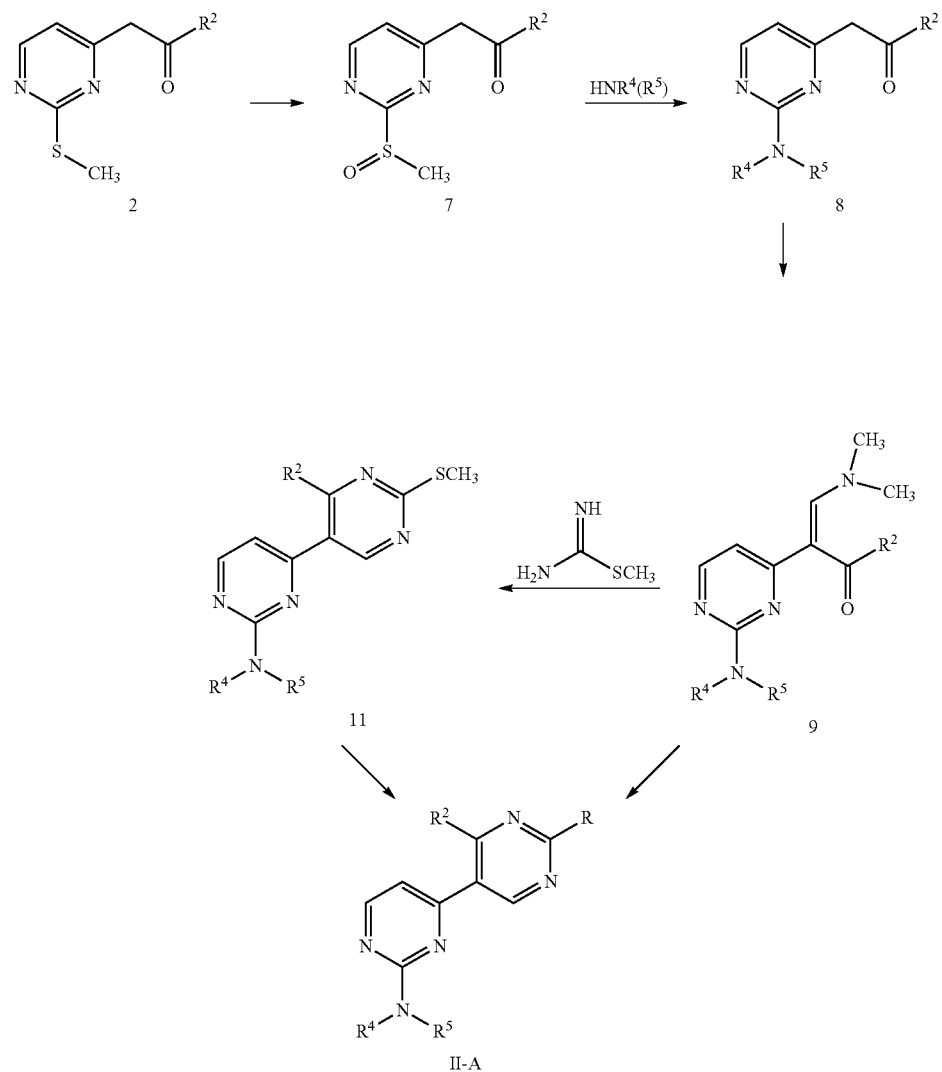

II-A

Generally, the compounds of formula II-A can be prepared according to Scheme 2, starting from intermediate 2, which is prepared as described in Scheme 1. As to the individual steps in the scheme above, step 1 involves the oxidation of the sulfide to the sulfone or sulfoxide utilizing a suitable oxidizing agent such as m-Chloroperoxybenzoic acid. The sulfoxide or sulfone moiety can then be displaced by reaction with aliphatic amines in the microwave at 160° C. or alternatively by addition of deprotonated aryl or heteroarylamines. Further reaction of ketones of formula 8 with N,N-dimethylformamide dimethyl acetal in the absence of solvent at 80° C. affords vinylogous amides 9. Compounds II-A can be prepared from intermediate 9 via reaction with 2-methyl-2-thiopseudourea sulfate in the presence of a suitable base such as potassium carbonate at 120° C. followed by reaction of intermediate 11 with R substituted amines in the microwave at 160° C. Alternatively, Compounds I-A can be prepared from intermediate 9 by heating with R substituted guanidines.

Scheme III below describes an alternative synthesis for preparing Compounds of Formula III-A Scheme III

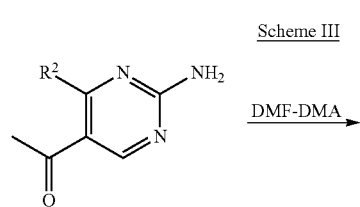

DMF-DMA

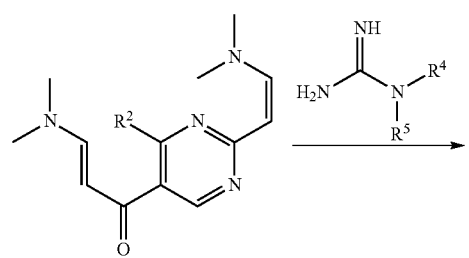

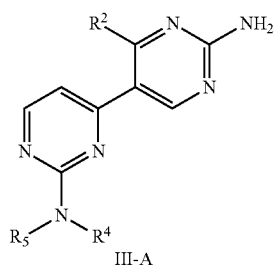

III-A

Generally, the compounds of formula III-A can be prepared according to Scheme 3, starting from 5-acetyl-2-amino-4-methylpyrimidine (Alfa Aesar) and heating in N,N-dimethylformamide dimethyl acetal, followed by reaction with substituted guanidines in the presence of a suitable base such as potassium carbonate at 120° C.

Scheme IV below describes the synthesis for preparing compounds of the formula IV-A.

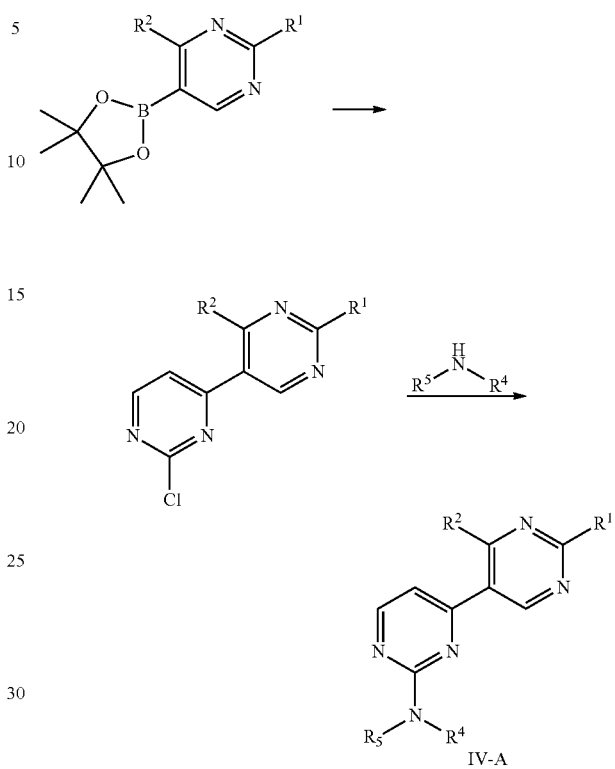

IV-A

Generally, the compounds of formula 1V-A can be prepared according to scheme 4, utilizing a Suzuki coupling with the appropriate boronate ester and 2,4-dichloropyrimidine. Subsequent reaction with various amines in the microwave affords the desired aminopyrimidines.

Scheme V below describes and alternate synthesis of the compounds of formula I-A, or V-A.

Scheme V

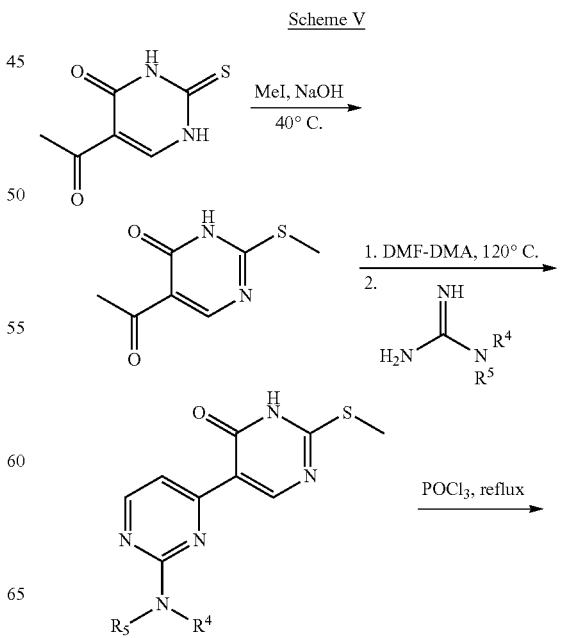

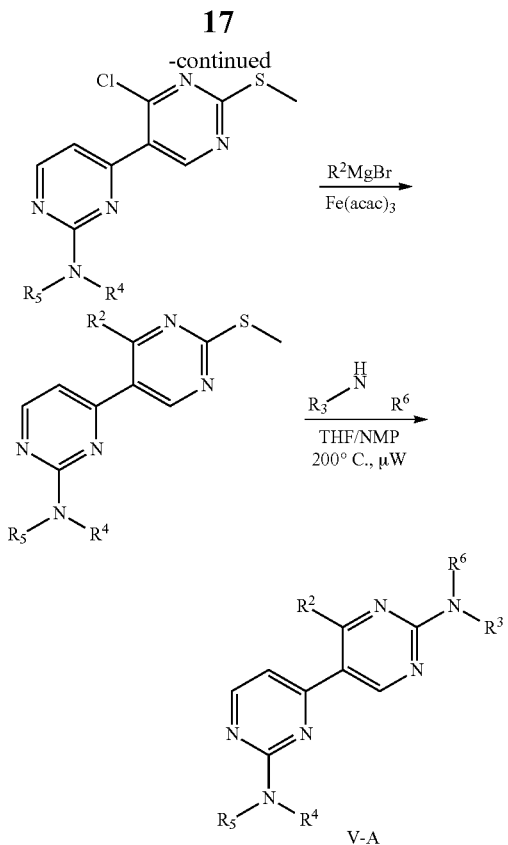

Generally, the compounds of formula V-A can be prepared according to Scheme 5, starting from 5-acetyl-2-thioxo-2,3-dihydropyrimidin-4(1H)-one (Ryan Scientific). Step 1 involves methylation, which is followed by reaction with N,N-dimethylformamide dimethyl acetal at 120° C. and subsequent reaction with substituted guanidines in the presence of a suitable base such as potassium carbonate at 120° C. Final compounds are prepared by chlorination with a reagent such as $POCl_3$ followed by reaction with various amines at 200° C. in the microwave.

The compounds of the present invention may be isolated and used per se or in the form of its pharmaceutically acceptable salt, solvate and/or hydrate. Many of the compounds represented by Formula I are capable of forming acid addition salts, particularly pharmaceutically acceptable acid addition salts. Pharmaceutically acceptable acid addition salts of the compound of the present invention include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I and Id by known salt-forming procedures.

Compounds of the present invention which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula I by known salt-forming procedures.

For those compounds containing an asymmetric carbon atom, the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a commercially available chiral HPLC column.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of Formula I (or pharmaceutically acceptable salt thereof) in combination with an excipient, wherein the excipient is a solvent.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention includes all pharmaceutically acceptable isotopically-labeled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

Compounds of the present invention are useful for treating diseases, conditions and disorders modulated by the inhibition of the Vps34 enzyme; consequently, the compounds of the present invention (including the compositions and processes used therein) may be used in the manufacture of a medicament for the therapeutic applications described herein. Hence, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention are useful as both prophylactic and therapeutic treatments for diseases or conditions related to the hyperactivity of VPS34, as well as diseases or conditions modulated by the autophagy and endocytic pathways.

Vps34 inhibitors can be used to inhibit autophagy in a variety of diseases, including but not limited to a variety of human cancers including colon/rectum, lung, breast, prostrate, urinary, kidney, and pancreatic. Other diseases where Vps34 can be used to modulate autophagy include neurodegenerative disorders such as HD, PD, ALS, inflammatory bowel disease (including Crohn's disease), malarial infection, and dengue.

Thus, as a further aspect, the invention relates to a method for treating a disease or condition related to the hyperactivity of Vps34, or a disease or condition modulated by the Vps34, comprising administration of an effective therapeutic amount of a compound of formula (I) or a pharmaceutically acceptable salt thereof.

As a further aspect, the invention relates to a method for treating proliferative diseases, such as cancer, comprising administration of an effective amount of a compound of formula (I) or a pharmaceutically acceptable salt thereof.

Examples of cancers include but are not limited to acute and chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma, colorectal cancer, kidney, lung, liver, pancreatic, breast, glioma, or neuroblastoma.

Additionally, compounds of formula (I) may also be useful as therapeutics for diseases such as muscle diseases such as central nuclear myopathies (e.g. X-linked myotubular myopathies), chloroquine-induced myopathy, myopathies with excessive autophagy, Duchene's muscular dystrophy, Charcot Marie Tooth Disease (e.g. type 4B), demyelinating neuropathies, celiac disease, inflammatory bowel disease, Crohns' disease and various autoimmune diseases.

An Vps34 inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from, e.g., proteosome inhibitors, Bcl-2 inhibitors, Bcr-Abl inhibitors such as Gleevec and derivatives, mTOR inhibitors, PI3K inhibitors, dual PI3K-mTOR inhibitors, lipid kinase inhibitors, Ras, Raf, MEK, ERK1/2 inhibitors, TNF-R ligands, UPR/ER stress inducers, or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

Compounds of the present invention may also be combined with disease-modifying anti-rheumatic agents (DMARDs), e.g. methotrexate, leflunamide, sulfasalazine; gold salts, penicillamine, hydroxychloroquine and chloroquine.

The term "mTOR inhibitors" relates to compounds which inhibit the mammalian target of rapamycin (mTOR) and which possess antiproliferative activity such as sirolimus (Rapamune), everolimus (CerticanÔ), CCI-779, RAD001, and ABT578. Other examples of mTOR inhibitors would include "catalytic" modulators such as NVP-BEZ235 and Ku-0063794.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341. The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Ax1 receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as com-pounds which target decrease or inhibit the activity of c-AbI family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

EXAMPLES

The abbreviations listed below have the corresponding meanings:
DCM: Dichloromethane
DME: Dimethyl ether
DMF: Dimethylformamide
DMF-DMA: N,N-Dimethylformamide dimethyl acetal
DMSO: Dimethylsulfoxide
EtOAc: Ethyl acetate
Fe(acac)$_3$: Ferric acetylanetonate
HCl: Hydrochloric acid
HPLC: High performance liquid chromatography
hr: Hour
HRMS: High resonance mass spectrometry
K$_2$CO$_3$: Potassium carbonate LCMS: Liquid chromatography mass spectrometry
LHMDS: Lithium hexamethyldisilazide
LiHMDS: Lithium hexamethyldisilazide
mCPBA: m-Chloroperoxybenzoic acid
MeCN: Acetonitrile
MeI: Methyl iodide
MeOH: Methanol
Min: Minutes
MS: Mass spectrometry
MSCl: Methanesulfonyl chloride
NaOH: Sodium hydroxide
$Na_2CO_3$: Sodium carbonate
NMP: 1-Methyl-2-pyrrolidinone
$PdCl_2.CH_2Cl_2$: [1,1'-Bis(diphenylphosphino)ferrocene]dichloropalladium(II), complex with dichloromethane
$POCl_3$: Phosphorus oxychloride
rt: Room temperature
TBAF: Tetrabutylammonium fluoride
THF: Tetrahydrofuran
TLC: Thin layer chromatography
Tol: Toluene
$t_R$: Retention time
UV: Ultraviolet
μW: Microwave Analytical HPLC Methods:

Method 1: Inertsil ODS3 100×3 mm C18 column at the flow rate of 1.0 mL/min, with a gradient of 5-95% acetonitrile/water with 0.1% formic acid over 7.75 min Method 2: Inertsil $C_{8-3}$ column with a gradient of 5-95% acetonitrile/water with 5 mM ammonium formate over 2.0 min All HPLC retention times refer to Method 1 unless otherwise denoted by (*), which refers to Method 2.

Preparation of intermediate 1-Cyclopropyl-3-[2-(methylsulfanyl)pyrimidin-4-yl]propan-2-one (2)

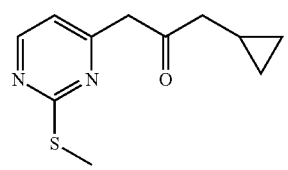

To a solution of 4-methyl-2-(methylthio)pyrimidine (5.63 mL, 40.4 mmol) in THF (20 mL) at −10° C., LiHMDS (60.6 mL, 60.6 mmol) (1N in MBTE) was added dropwise under nitrogen. The reaction mixture coagulated, and stopped stirring. For this, additional THF (40 mL) was added to dissolve the highly viscous mixture. The reaction was warmed up to rt and was stirred for 30 minutes. The reaction mixture was re-cooled to −10° C., then 2-cyclopropyl-N-methoxy-N-methylacetamide (7.47 g, 40.4 mmol) was added dropwise. The reaction mixture was warmed up to rt, then stirred for an additional 2 hours. The reaction was partitioned between ammonium chloride solution and EtOAc. The organic layer was separated, and the aqueous layer was back-extracted. The organic extracts were combined, washed with brine, dried over sodium sulfate, then concentrated in vacuo. The crude product was purified by Biotage™ silica gel chromatography [100 g SNAP column, 10% EtOAc/heptane to 100% EtOAc] to obtain the desired product, which was still contaminated significantly with the starting material, 4-methyl-2-(methylthio)pyrimidine (5.63 g, 48% yield). The product was carried on to the next step without further purification. MS (ES+): m/z=223.2/224.3 (100/50) [MH$^+$]. HPLC: $t_R$=0.84 minute over 3 minutes. Purity: 77% [HPLC (LC/MS) at 220 nm].

Preparation of intermediate (3Z)-1-Cyclopropyl-4-(dimethylamino)-3-[2-(methylsulfanyl)pyrimidin-4-yl]but-3-en-2-one (3)

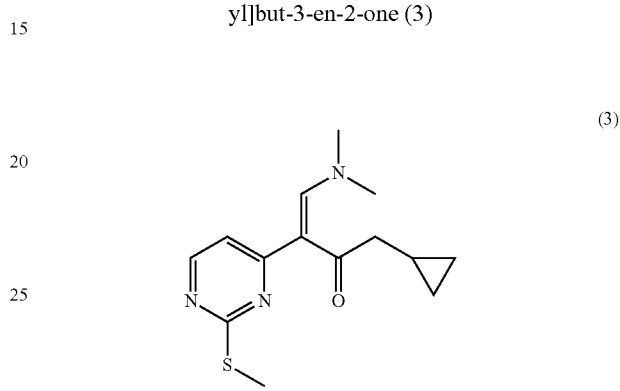

A solution of 1-cyclopropyl-3-[2-(methylsulfanyl)pyrimidin-4-yl]propan-2-one (2) (216.3 mg, 0.973 mmol) in DMF-DMA (1303 μl, 9.73 mmol) was stirred at 80° C. for 2 hours. The reaction was partitioned between water and EtOAc. The organic layer was separated, and the aqueous layer was back-extracted. The organic extracts were combined, washed with brine, dried over sodium sulfate, then concentrated in vacuo. The crude product was purified by Biotage™ silica gel chromatography [25 g ISOLUTE column, 100% DCM to 10% MeOH/DCM] to obtain the desired product as a orange-yellow solid (186.8 mg, 69.2% yield). MS (ES+): m/z=278.2/279.2 (100/50) [MH$^+$]. HPLC: $t_R$=0.99 minute over 3 minutes. Purity: 100% [HPLC (LC/MS) at 220 nm].

Preparation of intermediate 4'-(Cyclopropylmethyl)-2-(methylsulfanyl)-4,5'-bipyrimidine (4a)

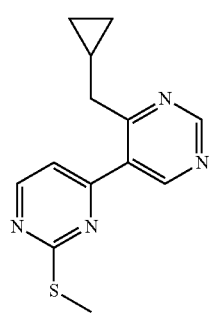

A solution of (3Z)-1-cyclopropyl-4-(dimethylamino)-3-[2-(methylsulfanyl)pyrimidin-4-yl]but-3-en-2-one (3) (200 mg, 0.721 mmol), formamidine acetate (75 mg, 0.721 mmol), and K$_2$CO$_3$ (299 mg, 2.163 mmol) in DMF (6 mL) was stirred at 120° C. for 30 minutes, followed by stirring at rt for 18 hours. The reaction was partitioned between water and EtOAc. The organic layer was separated, and the aqueous layer was back-extracted. The organic extracts were combined, washed with brine, dried over sodium sulfate, then concentrated in vacuo. The crude product was purified by Biotage™ silica gel chromatography [10 g SNAP column, 30% EtOAc/heptane to 100% EtOAc] to obtain the desired product as a white solid (62.5 mg, 29.4% yield). The desired product contained a small amount of an unknown by-product and was carried on to the next step without further purification. MS (ES+): m/z=259.3 (100) [MH$^{+2}$]. HPLC: $t_R$=1.77 minutes over 3 minutes. Purity: 87.5% [HPLC (LC/MS) at 220 nm].

Preparation of intermediate 4'-(cyclopropylmethyl)-2-(methylsulfinyl)-4,5'-bipyrimidine (5a)

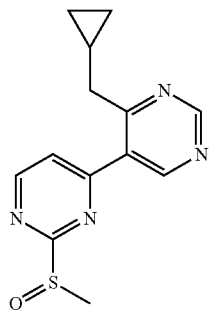

(5a)

To a solution of 4'-(cyclopropylmethyl)-2-(methylsulfanyl)-4,5'-bipyrimidine (4a) (62.5 mg, 0.242 mmol) in DCM (968 µl), mCPBA (65.1 mg, 0.290 mmol) was added and the reaction mixture was stirred at rt for 1 hour. The crude reaction mixture was partitioned between saturated sodium bicarbonate solution and DCM. The aqueous layer was separated and back-extracted twice with DCM. The combined organic extracts were washed with brine, dried over sodium sulfate, then concentrated in vacuo. The crude product was carried on to the next step without further purification. MS (ES+): m/z=275.2 (100) [MH$^+$]. HPLC: $t_R$=0.72 minute over 3 minutes. Purity: 100% [HPLC (LC/MS) at 220 nm].

Preparation of Trans-4-{[4'-(cyclopropylmethyl)-4,5'-bipyrimidin-2-yl]amino}cyclohexanol (6a)

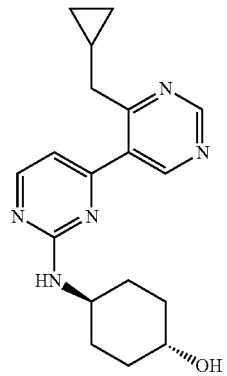

(6a)

To a solution of 4'-(cyclopropylmethyl)-2-(methylsulfinyl)-4,5'-bipyrimidine (46.0 mg, 0.168 mmol) in DMSO (1 mL), 4-trans-aminocyclohexanol (97 mg, 0.838 mmol) was added and the reaction was microwaved for 20 minutes at 160° C. Additional 4-trans-aminocyclohexanol (97 mg, 0.838 mmol) was added to the reaction mixture, and the reaction was microwaved at 160° C. for an additional 30 minutes. Almost no reaction (<10%) was observed by LC/MS. Additional 4-trans-aminocyclohexanol (194 mg, 1.676 mmol) was added, and the reaction mixture was microwaved at 160° C. for additional 1 hour. The reaction was cooled to rt and the crude reaction mixture was purified by reverse-phase HPLC [30-100% organic phase over 15 minutes] followed by Biotage™ silica gel chromatography [10 g SNAP column, 100% DCM to 10% MeOH/DCM] to obtain the desired product. The desired product was further purified by a trituration with acetone to remove a yellow impurity, and was dried over high vacuum for 5 hours to afford the title compound as a white solid (23.49 mg, 43.1% yield). 1H NMR (400 MHz, DMSO-d$_6$) δ ppm 0.14 (br. s., 2H) 0.41 (d, J=7.07 Hz, 2H) 1.07-1.37 (m, 5H) 1.86 (t, J=14.40 Hz, 6H) 2.74-3.01 (m, 2H) 3.34-3.47 (m, 1H) 3.59-3.77 (m, 1H) 4.50 (d, J=4.55 Hz, 1H) 6.81 (d, J=4.55 Hz, 1H) 7.21 (d, J=7.58 Hz, 1H) 8.39 (d, J=5.05 Hz, 1H) 8.77 (br. s., 1H) 9.16 (s, 1H). HRMS (ES+) for C18H23N5O.H$^+$ [MH$^+$]: calcd, 326.1981; found, 326.1980. UV-LC: 100/100% UV purity at 254/214 nm; $t_R$=3.79 minutes over 7.75 minutes.

The compounds listed in Table 1 below were prepared using procedures analogous to those described above for the synthesis of Compound 6a using the appropriate starting materials.

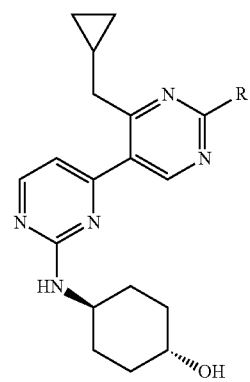

TABLE 1

| Example | R | HRMS (ES+ m/z) | HPLC $t_R$ (min) | 1H NMR |
|---|---|---|---|---|
| 6b | NH$_2$ | M + 1 = 341.2085 | 2.84 | (400 MHz, DMSO-d$_6$) δ ppm 0.09 (br. s., 2 H) 0.37 (d, J = 27.58 Hz, 2 H) 1.01-1.13 (m, 1 H) 1.14-1.39 (m, 4 H) 1.74-1.95 (m, 4 H) 2.79 (br. s., 2 H) 3.35-3.45 (m, 1 H) 3.67 (dd, J = 7.83, 3.79 Hz, 1 H) 4.51 (d, J = 4.04 Hz, 1 H) 6.69 (d, J = 5.05 Hz, 1 H) 6.85 (s, 2 H) 6.95 (d, J = 28.08 Hz, 1 H) 8.24 (d, J = 5.05 Hz, 1 H) 8.31 (s, 1 H) |
| 6c | Methyl | M + 1 = 340.2148 | 3.91 | (400 MHz, DMSO-d$_6$) δ ppm 0.11 (br. s., 2 H) 0.38 (d, J = 7.07 Hz, 2 H) 1.06-1.36 (m, 5 H) 1.85 (t, J = 14.15 Hz, 4 H) 2.65 (s, 3 H) 2.73-2.95 (m, 2 H) 3.33-3.45 (m, 1 H) 3.59-3.78 (m, 1 H) 4.50 (d, J = 4.55 Hz, 1 H) 6.78 (d, J = 5.05 Hz, 1 H) 7.16 (d, J = 7.58 Hz, 1 H) 8.36 (d, J = 4.55 Hz, 1 H) 8.65 (s, 1 H) |
| 6d | Ethyl | M + 1 = 354.2290 | 4.46 | (400 MHz, DMSO-d$_6$) δ ppm 0.13 (br. s., 2 H) 0.39 (d, J = 7.58 Hz, 2 H) 1.06-1.36 (m, 8 H) 1.73-1.96 (m, 4 H) 2.07 (s, 2 H) 2.75-3.00 (m, 4 H) 3.37-3.50 (m, 5 H) 3.68 (dd, J = 7.33, 3.79 Hz, 1 H) 6.79 (d, J = 5.05 Hz, 1 H) 7.16 (d, J = 8.08 Hz, 1 H) 8.36 (d, J = 5.05 Hz, 1 H) 8.69 (br. s., 1 H) |
| 6e | ---NH-- (N-methyl) | M + 1 = 355.2237 | 3.28 | (400 MHz, DMSO-d$_6$) δ ppm 0.05-0.24 (m, 2 H) 0.38 (d, J = 6.57 Hz, 2 H) 0.95-1.15 (m, 1 H) 1.15-1.40 (m, 4 H) 1.74-1.97 (m, 4 H) 2.82 (br. s., 2 H) 2.85 (d, J = 5.05 Hz, 3 H) 3.34-3.46 (m, 1 H) 3.58-3.78 (m, 1 H) 4.51 (d, J = 4.55 Hz, 1 H) 6.69 (d, J = 5.05 Hz, 1 H) 6.94 (d, J = 7.58 Hz, 1 H) 7.30 (br. s., 1 H) 8.24 (d, J = 4.55 Hz, 1 H) 8.37 (br. s., 1 H) |
| 6f | ---O--methyl | M + 1 = 356.2082 | 4.29 | (400 MHz, DMSO-d$_6$) δ ppm 0.15 (br. s., 2 H) 0.42 (d, J = 7.07 Hz, 2 H) 1.06-1.36 (m, 5 H) 1.85 (t, J = 14.15 Hz, 4 H) 2.86 (br. s., 2 H) 3.33-3.48 (m, 1 H) 3.58-3.76 (m, 1 H) 3.97 (s, 3 H) 4.51 (d, J = 4.04 Hz, 1 H) 6.77 (d, J = 5.05 Hz, 1 H) 7.12 (d, J = 8.08 Hz, 1 H) 8.34 (d, J = 5.05 Hz, 1 H) 8.62 (br. s., 1 H) |

Preparation of intermediate 4'-(Cyclopropylmethyl)-N-methyl-2-(methylsulfanyl)-4,5'-bipyrimidin-2'-amine (4-1)

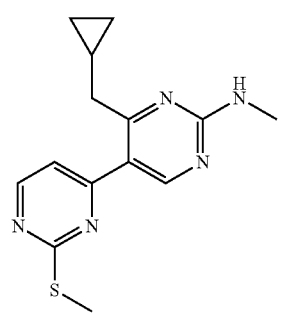

(4-1)

A solution of (3Z)-1-cyclopropyl-4-(dimethylamino)-3-[2-(methylsulfanyl)pyrimidin-4-yl]but-3-en-2-one (3) (810 mg, 2.92 mmol), N-methylguanidine (480 mg, 4.38 mmol), and K$_2$CO$_3$ (1211 mg, 8.76 mmol) in DMF (28 mL) was stirred at 120° C. for 2 hours, followed by stirring at rt for 18 hours. The reaction was partitioned between water and EtOAc. The organic layer was separated, and the aqueous layer was back-extracted. The organic extracts were combined, washed with brine, dried over sodium sulfate, then concentrated in vacuo. The crude product was purified by Biotage™ silica gel chromatography [100 g SNAP column, 30% EtOAc/heptane to 100% EtOAc] to afford the desired product as a white solid (720 g, 86% yield). $^1$H NMR (400 MHz, DMSO-d$_6$) δ ppm 0.12 (br. s., 2H) 0.37 (d, J=7.07 Hz, 2H) 1.07 (br. s., 1H) 2.81 (d, J=6.57 Hz, 2H) 2.87 (d, J=5.05 Hz, 3H) 7.39 (d, J=5.05 Hz, 1H) 7.49 (br. s., 1H) 8.49 (br. s., 1H) 8.60 (d, J=5.05 Hz, 1H). MS (ES+): m/z=288.2/289.2/290.2 (100/20/10) [MH$^+$]. HPLC: $t_R$=1.28 minutes over 3 minutes. Purity: 100% [HPLC (LC/MS) at 220 nm].

Preparation of intermediate 4'-(Cyclopropylmethyl)-N-methyl-2-(methylsulfinyl)-4,5'-bipyrimidin-2'-amine (5-1)

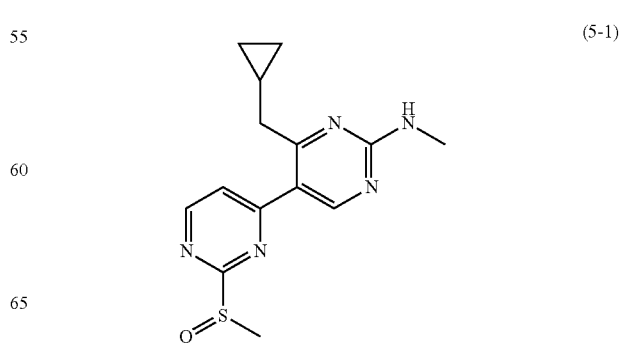

(5-1)

To a solution of 4'-(cyclopropylmethyl)-N-methyl-2-(methylsulfanyl)-4,5'-bipyrimidin-2'-amine (4-1) (770 mg, 2.68 mmol), m-CPBA (925 mg, 5.36 mmol) was added and the reaction mixture was stirred at rt for 2 hours. The reaction was partitioned between water and DCM. The organic layer was separated, and the aqueous layer was back-extracted. The organic extracts were combined, washed with brine, dried over sodium sulfate, then concentrated in vacuo. The crude product was purified by Biotage™ silica gel chromatography [50 g SNAP column, 100% DCM to 10% MeOH/DCM] to obtain a mixture of the desired product and the corresponding sulfone (645 mg, 79% yield). MS (ES+): m/z=304.2/305.2 (100/20) [MH$^+$]. HPLC: $t_R$=0.85 minute over 3 minutes. Purity: 73.2% [HPLC (LC/MS) at 220 nm].

Examples 14a-14s

General Method: Synthesis of 14a-d, 14l-m, 14p-q

Preparation of 4'-Cyclopropylmethyl-N$^2$-(6-methoxy-pyridin-3-yl)-N$^{2'}$-methyl-[4,5]bipyrimidinyl-2,2'-diamine (14a)

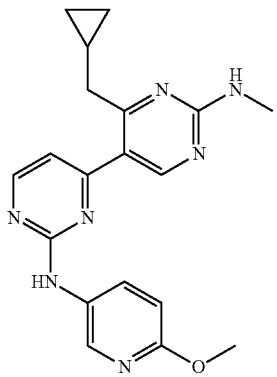

(14a)

To a solution of 6-methoxypyridin-3-amine (61.4 mg, 0.494 mmol) in THF (5 mL) cooled to −78° C., lithium bis(trimethylsilyl)amide (1M in THF, 0.494 mL, 0.494 mmol) was added dropwise under nitrogen. After the reaction was stirred at −78° C. for 10 minutes, a solution of 4'-(cyclopropylmethyl)-N-methyl-2-(methylsulfinyl)-4,5'-bipyrimidin-2'-amine (5-1) (30 mg, 0.099 mmol) in THF (1 mL) was added to the reaction at −78° C. The reaction was slowly warmed up to rt, then the reaction was allowed to stir for 1 hour. The reaction was quenched with saturated ammonium chloride solution, then concentrated in vacuo. The reaction was taken up in acetonitrile, purified by reverse-phase HPLC [10-90% organic phase over 15 minutes], then further purified by Biotage™ silica gel chromatography [10 g SNAP column, 100% DCM to 7% MeOH/DCM] to afford the title compound as a white solid (19.49 mg, 46.0% yield). 1H NMR (400 MHz, DMSO-d$_6$) δ ppm 0.04 (br. s., 2H) 0.34 (d, J=7.58 Hz, 2H) 1.01 (br. s., 1H) 2.77 (d, J=6.57 Hz, 2H) 2.86 (d, J=4.55 Hz, 3H) 3.74-3.86 (m, 3H) 6.78 (d, J=9.09 Hz, 1H) 6.97 (d, J=5.05 Hz, 1H) 7.36 (d, J=4.04 Hz, 1H) 7.99 (dd, J=8.59, 2.53 Hz, 1H) 8.35-8.50 (m, 3H) 9.46 (s, 1H). HRMS (ES+) for C19H21N7O.H$^+$ [MH$^+$]: calcd, 364.1886; found, 364.1891. UV-LC: 94.60/100% UV purity at 254/214 nm; $t_R$=5.08 minutes over 7.75 minutes.

General Method for Synthesis of 14e-k, 14n-o, 14r-s

Preparation of N$^2$-Cyclohexyl-4'-cyclopropylmethyl-N$^{2'}$-methyl-[4,5']bipyrimidinyl-2,2'-diamine (14e)

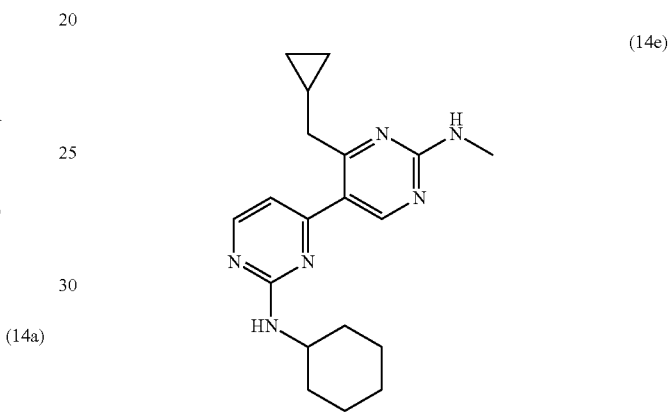

(14e)

To a solution of 4'-(cyclopropylmethyl)-N-methyl-2-(methylsulfinyl)-4,5'-bipyrimidin-2'-amine (5-1) (50 mg, 0.165 mmol) in DMSO (1 mL), cyclohexylamine (94 μL, 0.824 mmol) was added, and the reaction was heated in the microwave at 160° C. for 10 minutes. The crude reaction was purified by reverse-phase HPLC [30-100% organic phase with 3% n-propanol modifier over 15 minutes] followed by Biotage™ silica gel chromatography [10 g SNAP column, 100% DCM to 10% MeOH/DCM] to obtain the pure desired product as a white solid (39.0 mg, 69.9% yield). 1H NMR (400 MHz, DMSO-d$_6$) δ ppm 0.04-0.20 (m, 2H) 0.37 (d, J=7.58 Hz, 2H) 0.99-1.19 (m, 2H) 1.19-1.36 (m, 4H) 1.59 (d, J=11.62 Hz, 1H) 1.65-1.80 (m, 2H) 1.88 (d, J=8.59 Hz, 2H) 2.72-2.90 (m, 5H) 3.63-3.80 (m, 1H) 6.68 (d, J=5.05 Hz, 1H) 6.96 (d, J=8.08 Hz, 1H) 7.29 (br. s., 1H) 8.24 (d, J=5.05 Hz, 1H) 8.36 (br. s., 1H). HRMS (ES+) for C19H26N6.H$^+$ [MH$^+$]: calcd, 339.2297; found, 339.2312. UV-LC: 100% UV purity at 254/214 nm; $t_R$=6.70 minutes over 7.75 minutes.

The compounds listed in Table 2 below were prepared using the procedures as indicated above using the appropriate starting materials.

TABLE 2

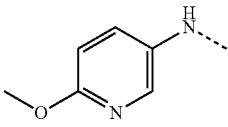

| Example | R | MS (ES+ m/z) | HPLC $t_R$ (min) | 1H NMR |
|---|---|---|---|---|
| 14a | 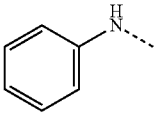 | M +1 = 364.1891 | 5.08 | (400 MHz, DMSO-$d_6$) δ ppm 0.04 (br. s., 2 H) 0.34 (d, J = 7.58 Hz, 2 H) 1.01 (br. s., 1 H) 2.77 (d, J = 6.57 Hz, 2 H) 2.86 (d, J = 4.55 Hz, 3 H) 3.74-3.86 (m, 3 H) 6.78 (d, J = 9.09 Hz, 1 H) 6.97 (d, J = 5.05 Hz, 1 H) 7.36 (d, J = 4.04 Hz, 1 H) 7.99 (dd, J = 8.59, 2.53 Hz, 1 H) 8.35-8.50 (m, 3 H) 9.46 (s, 1 H) |
| 14b | 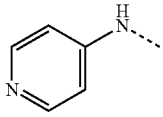 | M + 1 = 333.1823 | 5.89 | (400 MHz, DMSO-$d_6$) δ ppm 0.04 (br. s., 2 H) 0.34 (d, J = 7.58 Hz, 2 H) 1.01 (br. m, 1 H) 2.81 (d, J = 7.07 Hz, 2 H) 2.87 (d, J = 4.55 Hz, 3 H) 6.86-7.04 (m, 2 H) 7.27 (t, J = 8.08 Hz, 2 H) 7.36 (d, J = 4.04 Hz, 1 H) 7.75 (d, J = 7.58 Hz, 2 H) 8.42 (br. s., 1 H) 8.48 (d, J = 5.05 Hz, 1 H) 9.56 (s, 1 H). |
| 14c | 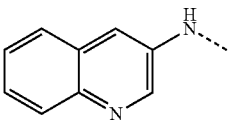 | M + 1 = 334.1769 | 2.80 | (400 MHz, DMSO-$d_6$) δ ppm 0.04 (br. m, 2 H) 0.35 (d, J = 7.07 Hz, 2 H) 1.01 (br. s., 1 H) 2.83 (d, J = 7.07 Hz, 2 H) 2.87 (d, J = 4.55 Hz, 3 H) 7.15 (d, J = 5.56 Hz, 1 H) 7.41 (d, J = 3.03 Hz, 1 H) 7.77 (d, J = 6.57 Hz, 2 H) 8.35 (d, J = 6.57 Hz, 2 H) 8.45 (br. s., 1 H) 8.59 (d, J = 5.05 Hz, 1 H) 10.07 (s, 1 H) |
| 14d | 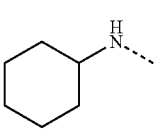 | M + 1 = 384.1943 | 4.99 | (400 MHz, DMSO-$d_6$) δ ppm 0.03 (br. s., 3 H) 0.32 (d, J = 7.07 Hz, 2 H) 1.03 (br. s., 1 H) 2.75-2.96 (m, 5 H) 7.12 (d, J = 5.56 Hz, 1 H) 7.41 (d, J = 4.55 Hz, 1 H) 7.48-7.67 (m, 2 H) 7.83 (d, J = 7.58 Hz, 1 H) 7.93 (d, J = 8.08 Hz, 1 H) 8.48 (br. s., 1 H) 8.59 (d, J = 5.05 Hz, 1 H) 8.79 (d, J = 2.02 Hz, 1 H) 9.10 (d, J = 2.53 Hz, 1 H) 10.08 (s, 1 H) |
| 14e |  | M + 1 = 339.2312 | 6.70 | (400 MHz, DMSO-$d_6$) δ ppm 0.04-0.20 (m, 2 H) 0.37 (d, J = 7.58 Hz, 2 H) 0.99-1.19 (m, 2 H) 1.19-1.36 (m, 4 H) 1.59 (d, J = 11.62 Hz, 1 H) 1.65-1.80 (m, 2 H) 1.88 (d, J = 8.59 Hz, 2 H) 2.72-2.90 (m, 5 H) 3.63-3.80 (m, 1 H) 6.68 (d, J = 5.05 Hz, 1 H) 6.96 (d, J = 8.08 Hz, 1 H) 7.29 (br. s., 1 H) 8.24 (d, J = 5.05 Hz, 1 H) 8.36 (br. s., 1 H) |

TABLE 2-continued

| Example | R | MS (ES+ m/z) | HPLC t$_R$ (min) | 1H NMR |
|---|---|---|---|---|
| 14f | cyclobutyl-NH- | M + 1 = 311.1976 | 5.86 | (400 MHz, DMSO-d$_6$) δ ppm 0.10 (br. s., 2 H) 0.37 (d, J = 7.58 Hz, 2 H) 0.97-1.20 (m, 1 H) 1.53-1.74 (m, 2 H) 1.89-2.06 (m, 2 H) 2.16-2.30 (m, 2 H) 2.72-2.93 (m, 5 H) 4.27-4.46 (m, 1 H) 6.71 (d, J = 5.05 Hz, 1 H) 7.30 (d, J = 3.03 Hz, 1 H) 7.39 (d, J = 8.08 Hz, 1 H) 8.25 (d, J = 5.05 Hz, 1 H) 8.36 (br. s., 1 H) |
| 14g | tetrahydropyran-4-yl-NH- | M + 1 = 341.2090 | 4.85 | (400 MHz, DMSO-d$_6$) δ ppm 0.04-0.22 (m, 2 H) 0.37 (d, J = 7.58 Hz, 2 H) 1.08 (br. s., 1 H) 1.44-1.59 (m, J = 11.87, 11.87, 11.62, 4.04 Hz, 2 H) 1.82 (dd, J = 12.38, 2.27 Hz, 2 H) 2.73-2.91 (m, 5 H) 3.31-3.44 (m, 3 H) 3.87 (d, J = 11.12 Hz, 2 H) 3.91-4.03 (m, 1 H) 6.72 (d, J = 5.05 Hz, 1 H) 7.11 (d, J = 8.08 Hz, 1 H) 7.30 (br. s., 1 H) 8.27 (d, J = 5.05 Hz, 1 H) 8.37 (br. s., 1 H) |
| 14h | cyclopentyl-NH- | M + 1 = 325.2 | 6.26 | (400 MHz, DMSO-d$_6$) δ ppm 0.03-0.23 (m, 2 H) 0.29-0.46 (m, 2 H) 1.07 (br. s., 1 H) 1.41-1.60 (m, 4 H) 1.60-1.79 (m, 2 H) 1.79-2.00 (m, 2 H) 2.71-2.93 (m, 5 H) 4.09-4.26 (m, 1 H) 6.69 (d, J = 5.05 Hz, 1 H) 7.09 (d, J = 7.58 Hz, 1 H) 7.29 (d, J = 4.04 Hz, 1 H) 8.25 (d, J = 5.05 Hz, 1 H) 8.36 (br. s., 1 H) |
| 14i | trans-4-(Boc-amino)cyclohexyl-NH- | M + 1 = 454.2926 | 5.17 | (400 MHz, DMSO-d$_6$) δ ppm 0.08-0.26 (m, 2 H) 0.38 (d, J = 5.56 Hz, 2 H) 1.07 (br. s., 1 H) 1.15-1.34 (m, 4 H) 1.34-1.45 (m, 10 H) 1.89 (br. s., 4 H) 2.71-2.94 (m, 5 H) 3.17 (d, J = 5.05 Hz, 1 H) 3.66 (dd, J = 11.37, 3.28 Hz, 1 H) 5.75 (s, 1 H) 6.62-6.80 (m, 2 H) 6.95 (d, J = 8.08 Hz, 1 H) 7.29 (d, J = 4.04 Hz, 1 H) 8.24 (d, J = 5.05 Hz, 1 H) 8.36 (br. s., 1 H) |
| 14j | trans-4-aminocyclohexyl-NH- | M + 1 = 354.2414 | 4.99 | (400 MHz, DMSO-d$_6$) δ ppm 0.03-0.22 (m, 2 H) 0.32-0.51 (m, 2 H) 1.09 (br. s., 1 H) 1.38-1.66 (m, 4 H) 1.98-2.27 (m, 4 H) 2.77-2.92 (m, 2 H) 2.98 (s, 3 H) 3.05-3.21 (m, J = 11.56, 11.56, 3.92, 3.79 Hz, 1 H) 3.77-3.95 (m, 1 H) 6.74 (d, J = 5.05 Hz, 1 H) 8.26 (d, J = 5.56 Hz, 1 H) 8.34 (s, 1 H) |

TABLE 2-continued

| Example | R | MS (ES+ m/z) | HPLC t$_R$ (min) | 1H NMR |
|---|---|---|---|---|
| 14k | (trans-4-hydroxycyclohexylamino) | M + 1 = 355.2243 | 3.56 | (400 MHz, DMSO-d$_6$) δ ppm 0.10 (br. s., 2 H) 0.36 (d, J = 7.07 Hz, 2 H) 1.07 (br. s., 1 H) 1.46 (t, J = 12.13 Hz, 2 H) 1.53-1.81 (m, 6 H) 2.08 (s, 1 H) 2.81 (d, J = 6.57 Hz, 2 H) 2.85 (d, J = 5.05 Hz, 3 H) 3.74 (br. s., 2 H) 4.31 (d, J = 3.03 Hz, 1 H) 6.69 (d, J = 5.05 Hz, 1 H) 6.95 (d, J = 7.58 Hz, 1 H) 7.29 (d, J = 3.03 Hz, 1 H) 8.24 (d, J = 5.05 Hz, 1 H) 8.36 (br. s., 1 H) |
| 14l | (pyridin-3-ylamino) | M + 1 = 334.1785 | 3.08 | (400 MHz, DMSO-d$_6$) δ ppm 0.34 (d, J = 7.58 Hz, 2 H) 1.01 (br. s., 1 H) 2.80 (d, J = 6.57 Hz, 2 H) 2.87 (d, J = 4.55 Hz, 3 H) 7.05 (d, J = 5.05 Hz, 1 H) 7.31 (dd, J = 8.08, 4.55 Hz, 1 H) 7.39 (d, J = 4.04 Hz, 1 H) 8.11-8.25 (m, 2 H) 8.43 (br. s., 1 H) 8.51 (d, J = 5.05 Hz, 1 H) 8.89 (d, J = 2.53 Hz, 1 H) 9.77 (s, 1 H) |
| 14m | (4-methoxyphenylamino) | M + 1 = 363.1926 | 5.52 | (400 MHz, DMSO-d$_6$) δ ppm 0.01-0.12 (m, 2 H) 0.34 (d, J = 7.58 Hz, 2 H) 1.00 (br. s., 1 H) 2.79 (d, J = 7.07 Hz, 2 H) 2.86 (d, J = 4.55 Hz, 3 H) 3.72 (s, 3 H) 6.87 (m, 2 H) 6.91 (d, J = 5.05 Hz, 1 H) 7.34 (d, J = 4.04 Hz, 1 H) 7.61 (m, 2 H) 8.30-8.48 (m, 2 H) 9.35 (s, 1 H) |
| 14n | (trans-4-carboxycyclohexylamino) | M + 1 = 383.2184 | 3.71 | (400 MHz, DMSO-d$_6$) δ ppm 0.11 (br. s., 2 H) 0.37 (d, J = 7.58 Hz, 2 H) 1.08 (br. s., 1 H) 1.19-1.48 (m, 4 H) 1.94 (t, J = 10.36 Hz, 4 H) 2.05-2.22 (m, 1 H) 2.70-2.96 (m, 5 H) 3.62-3.87 (m, 1 H) 6.71 (d, J = 5.05 Hz, 1 H) 6.99 (d, J = 8.08 Hz, 1 H) 7.30 (br. s., 1 H) 8.25 (d, J = 4.55 Hz, 1 H) 8.37 (br. s., 1 H) |
| 14o | (trans-4-methoxycyclohexylamino) | M + 1 = 369.2399 | 4.29 | (400 MHz, MeOD) δ ppm 0.15 (d, J = 5.05 Hz, 2 H) 0.30-0.49 (m, 2 H) 1.10 (br. s., 1 H) 1.22-1.48 (m, 5 H) 2.08 (ddd, J = 8.72, 4.55, 4.42 Hz, 4 H) 2.85 (d, J = 6.57 Hz, 2 H) 2.98 (s, 3 H) 3.13-3.28 (m, 1 H) 3.70-3.95 (m, 1 H) 6.70 (d, J = 5.05 Hz, 1 H) 8.23 (d, J = 5.05 Hz, 1 H) 8.34 (s, 1 H) |
| 14p* | (3,5-dimethoxyphenylamino) | M + 1 = 393.3 | 1.3 | (400 MHz, MeOD) δ ppm 0.13 (d, J = 5.56 Hz, 2 H) 0.44 (d, J = 7.07 Hz, 2 H) 1.01-1.16 (m, 1 H) 2.98 (d, J = 7.07 Hz, 2 H) 3.03-3.10 (m, 4 H) 3.77 (s, 6 H) 6.24 (s, 1 H) 6.90 (d, J = 2.02 Hz, 2 H) 7.04 (d, J = 5.56 Hz, 1 H) 8.45 (d, J = 5.05 Hz, 1 H) 8.52 (s, 1 H) |

TABLE 2-continued
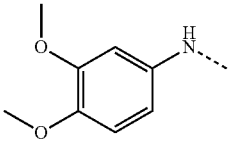
| Example | R | MS (ES+ m/z) | HPLC t$_R$ (min) | 1H NMR |
|---|---|---|---|---|
| 14q* | 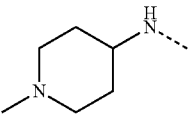 | M + 1 = 393.3 | 1.17 | (400 MHz, MeOD) δ ppm 0.16 (d, J = 3.54 Hz, 2 H) 0.46 (d, J = 7.07 Hz, 2 H) 1.11 (br. s., 1 H) 2.96 (d, 2 H) 3.09 (s, 3 H) 3.87 (s, 6 H) 6.98 (d, J = 8.59 Hz, 1 H) 7.08 (d, J = 5.56 Hz, 1 H) 7.14 (d, J = 8.08 Hz, 1 H) 7.31 (br. s., 1 H) 8.38 (d, J = 5.05 Hz, 1 H) 8.58 (br. s., 1 H) |
| 14r* | 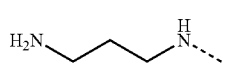 | M + 1 = 354.2 | 0.65 | (400 MHz, MeOD) δ ppm 0.20 (d, J = 4.55 Hz, 2 H) 0.40-0.54 (m, 2 H) 1.12 (br. s., 1 H) 1.87 (d, J = 14.65 Hz, 1 H) 2.34 (d, J = 14.15 Hz, 3 H) 2.87-3.00 (m, 7 H) 3.10-3.21 (m, 2 H) 3.61 (d, 2 H) 4.14-4.29 (m, 1 H) 7.01 (d, J = 4.04 Hz, 1 H) 8.32 (d, J = 6.06 Hz, 1 H) 8.55 (br. s., 1 H) (m, 1 H) |
| 14s* | H$_2$N∼∼N(H)- | M + 1 = 314.2 | | (400 MHz, MeOD) δ ppm 0.37 (d, J = 5.05 Hz, 2 H) 0.55-0.71 (m, 3 H) 1.32 (br. s., 1 H) 2.09-2.23 (m, 3 H) 3.13 (d, J = 6.57 Hz, 2 H) 3.19 (d, J = 8.08 Hz, 2 H) 3.77 (t, J = 6.06 Hz, 2 H) 7.22 (d, J = 2.53 Hz, 1 H) 8.46 (d, J = 6.06 Hz, 1 H) 8.75 (br. s., 1 H) |

Preparation of intermediate 4'-(Cyclopropylmethyl)-2-(methylthio)-4,5'-bipyrimidin-2'-amine (4-2)

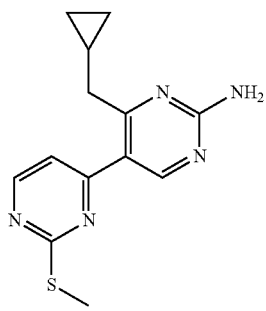

(4-2)

To a solution of (Z)-1-cyclopropyl-4-(dimethylamino)-3-(2-(methylthio)pyrimidin-4-yl)but-3-en-2-one (3) (2.07 g, 7.46 mmol) in DMF (62.2 ml) was added potassium carbonate (3.09 g, 22.39 mmol) and guanidine hydrochloride (1.065 g, 11.19 mmol). The resulting suspension was stirred at 120° C. After 45 minutes, the reaction was complete. The reaction mixture was concentrated in vacuo, then was taken up in EtOAc. The organic solution was washed with water, followed by brine, dried over sodium sulfate, then concentrated in vacuo. The crude residue was dried over high vacuum for 18 h to obtain the desired product as a bright orange product (2.17 g, quant. yield). MS (ES+): m/z=250.1 (50) [MH$^+$]. HPLC: $t_R$=1.13 min over 3 min. Purity: 100% [HPLC (LC/MS) at 220 nm]. $^1$H NMR (400 MHz, DMSO-d$_6$) d ppm 0.06-0.13 (m, 2H) 0.33-0.41 (m, 2H) 0.96-1.11 (m, 1H) 2.52-2.57 (m, 3H) 2.79 (d, J=7.07 Hz, 2H) 7.03 (s, 2H) 7.39 (d, J=5.56 Hz, 1H) 8.44 (s, 1H) 8.60 (d, J=5.56 Hz, 1H).

Preparation of intermediate 4'-(cyclopropylmethyl)-2-(methylsulfinyl)-4,5'-bipyrimidin-2'-amine (5-2)

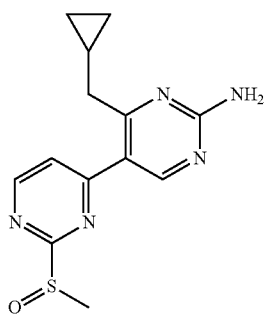

(5-2)

To a solution of 4'-(cyclopropylmethyl)-2-(methylthio)-4,5'-bipyrimidin-2'-amine (4a) (2.17 g, 7.14 mmol) in DCM (14.29 ml) was added m-CPBA (1.761 g, 7.14 mmol). Immediately after the addition of m-CPBA, the reaction completion was observed. The reaction mixture was diluted with DCM and water. The organic layer was washed with saturated sodium bicarbonate and brine, dried with sodium sulfate, and concentrated in vacuo. The crude residue was purified by Biotage flash chromatography [100 g SNAP column, eluted with 1-15% MeOH/DCM] to obtain the desired product as a slightly pale yellow solid (1.47 g, 71% yield). MS (ES+): m/z=290.4/291.5 (100/10) [MH$^+$]. HPLC: $t_R$=0.76 min over 3 min. Purity: 100% [HPLC (LC/MS) at 220 nm].

Examples 15a-15y

General Method for Synthesis of 15e-f, 15h-o, 15u-y

Preparation of 4'-Cyclopropylmethyl-N$^2$-(3-methyl-isoxazol-5-yl)-[4,5]bipyrimidinyl-2,2'-diamine (15h)

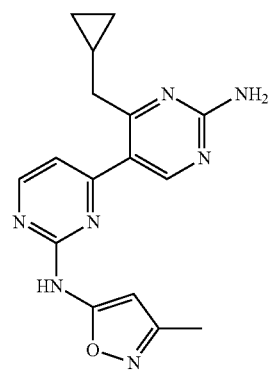

(15h)

To a solution of 3-methyl-isoxazol-5-ylamine in THF was added LiHMDS at −78° C., then the solution was stirred for 15 minutes, and 4'-(cyclopropylmethyl)-2-(methylsulfinyl)-4,5'-bipyrimidin-2'-amine (5-2) in THF was added to the reaction mixture. The reaction was warmed to rt and stirred for 1 hour. The reaction mixture was quenched with saturated ammonium chloride, extracted with ethyl acetate, dried over anhydrous sodium sulfate, and evaporated to give a crude product which was further purified by reverse-phase HPLC to give the desired product.

General Method for Synthesis of 15a-d, 15g, 15p-t, 16g

Preparation of 4'-(cyclopropylmethyl)-N2-(tetrahydro-2H-pyran-3-yl)-4,5'-bipyrimidine-2,2'-diamine (15d)

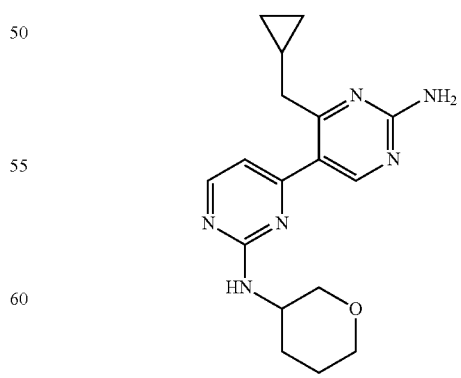

(15d)

To a solution of 4'-(cyclopropylmethyl)-2-(methylsulfinyl)-4,5'-bipyrimidin-2'-amine (5-2) (50 mg, 0.173 mmol) in DMSO (1 ml), was added Tetrahydro-pyran-3-ylamine HCl (119 mg, 0.864 mmol) and triethylamine (0.120 ml, 0.864 mmol) and the reaction was microwaved for 45 min at 160° C. The reaction was purified directly by reverse phase HPLC with a gradient of 10-90% acetonitrile in water over 15 minutes and then further purified by flash chromatography with a gradient of 25-100% ethyl acetate in heptane to give the desired product as a white solid (7.36 mg).

The compounds listed in Table 3 below were prepared using the procedures as indicated above using the appropriate starting materials.

TABLE 3

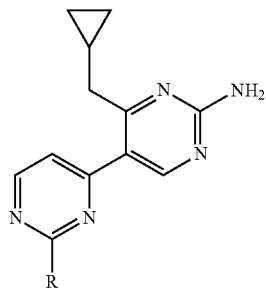

15

| Example | R | HRMS (ES+ m/z) | HPLC $t_R$ (min) | 1H NMR |
|---|---|---|---|---|
| 15a | | M + 1 = 382.2355 | 3.07 | (400 MHz, DMSO-$d_6$) δ ppm 0.07-0.17 (m, 2 H) 0.37 (d, J = 7.58 Hz, 2 H) 1.13-1.42 (m, 4 H) 1.77 (s, 3 H) 1.78-2.00 (m, 4 H) 2.71-2.89 (m, 2 H) 3.41-3.55 (m, 1 H) 3.70 (d, J = 8.08 Hz, 1 H) 6.70 (d, J = 5.05 Hz, 1 H) 6.85 (br. s., 2 H) 6.98 (d, J = 7.07 Hz, 1 H) 7.71 (d, J = 7.58 Hz, 1 H) 8.25 (d, J = 5.05 Hz, 1 H) 8.32 (br. s., 1 H) |
| 15b | | M + 1 = 418.2040 | 3.29 | (400 MHz, DMSO-$d_6$) δ ppm 0.04-0.20 (m, 2 H) 0.37 (d, J = 7.07 Hz, 2 H) 1.06 (br. s., 1 H) 1.20-1.46 (m, 4 H) 1.92 (d, J = 10.11 Hz, 4 H) 2.78 (d, J = 4.04 Hz, 2 H) 2.91 (s, 3 H) 3.08 (br. s., 1 H) 3.67 (br. s., 1 H) 6.70 (d, J = 5.05 Hz, 1 H) 6.84 (s, 2 H) 6.93-7.08 (m, 2 H) 8.25 (d, J = 5.05 Hz, 1 H) 8.31 (br. s., 1 H) |
| 15c | | M + 1 = 326.2107 | 2.96 | (400 MHz, CDCl3) δ ppm 0.13-0.18 (m, 2 H) 0.41-0.46 (m, 2 H) 1.05-1.15 (m, 1 H) 1.36-1.48 (m, 3 H) 1.97 (d, J = 11.62 Hz, 3 H) 2.84 (d, J = 6.57 Hz, 2 H) 2.99- 3.14 (m, 3 H) 4.77 (d, J = 13.14 Hz, 2 H) 5.12 (s, 2 H) 6.58 (d, J = 5.05 Hz, 1 H) 8.34 (d, J = 5.05 Hz, 1 H) 8.38 (s, 1 H) |
| 15d | | M + 1 = 327.1925 | 3.62 | (400 MHz, CDCl3) δ ppm 0.14-0.19 (m, 2 H) 0.41-0.48 (m, 2 H) 1.06-1.15 (m, 1 H) 1.59-1.75 (m, 2 H) 1.97-2.06 (m, 1 H) 2.82 (d, J = 7.07 Hz, 2 H) 3.45-3.52 (m, 1 H) 3.61-3.68 (m, 1 H) 3.69-3.76 (m, 1 H) 3.94 (dd, J = 11.12, 3.54 Hz, 3 H) 4.07-4.15 (m, 3 H) 5.23 (s, 5 H) 5.45 (d, J = 6.57 Hz, 2 H) 6.64 (d, J = 5.05 Hz, 1 H) 8.30 (d, J = 5.05 Hz, 1 H) 8.37 (s, 1 H) |

TABLE 3-continued
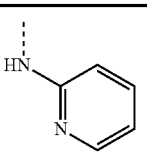
| Example | R | HRMS (ES+ m/z) | HPLC $t_R$ (min) | 1H NMR |
|---|---|---|---|---|
| 15e | 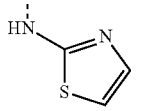 | M + 1 = 320.1639 | 2.50 | |
| 15f |  | M + 1 = 326.1192 | 3.98 | |
| 15g | 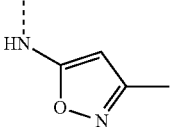 | M + 1 = 329.2084 | 3.53 | |
| 15h | 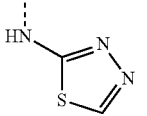 | M + 1 = 324.1583 | 4.28 | (400 MHz, DMSO-$d_6$) δ ppm 0.00-0.04 (m, 2 H) 0.31-0.37 (m, 2 H) 0.93-1.04 (m, 1 H) 2.17 (s, 3 H) 2.80 (d, J = 6.57 Hz, 2 H) 6.18 (s, 1 H) 6.98 (s, 2 H) 7.19 (d, J = 5.05 Hz, 1 H) 8.39 (s, 1 H) 8.58 (d, J = 5.05 Hz, 1 H) 11.16 (s, 1 H) |
| 15i | 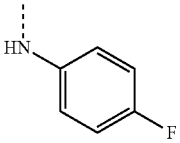 | M + 1 = 327.1131 | 3.63 | |
| 15j | 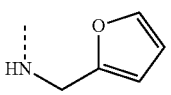 | M + 1 = 337.1570 | 5.21 | (400 MHz, DMSO-$d_6$) δ ppm 0.00-0.03 (m, 2 H) 0.30-0.35 (m, 2 H) 0.93-1.02 (m, 1 H) 2.77 (d, J = 6.57 Hz, 2 H) 6.91 (s, 2 H) 6.99 (d, J = 5.56 Hz, 1 H) 7.09-7.15 (m, 2 H) 7.72-7.77 (m, 2 H) 8.36 (s, 1 H) 8.46 (d, J = 5.05 Hz, 2 H) 9.61 (s, 1 H) |
| 15k | 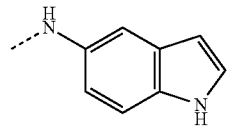 | M + 1 = 323.1625 | 4.21 | |
| 15l |  | M + 1 = 358.1773 | 4.21 | |

TABLE 3-continued
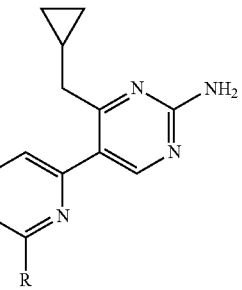
15
| Example | R | HRMS (ES+ m/z) | HPLC t$_R$ (min) | 1H NMR |
|---|---|---|---|---|
| 15m | HN—[benzo[1,3]dioxol-5-yl] | M + 1 = 363.1574 | 4.81 | |
| 15n | HN—[4-(acetamido)phenyl] | M + 1 = 376.1900 | 3.80 | (400 MHz, DMSO-d$_6$) δ ppm 0.01-0.07 (m, 2 H) 0.31-0.37 (m, 2 H) 0.94-1.02 (m, 1 H) 2.01 (s, 3 H) 2.82 (d, J = 6.57 Hz, 2 H) 6.98 (d, J = 5.05 Hz, 1 H) 7.47 (d, J = 9.09 Hz, 1 H) 7.62 (d, J = 9.09 Hz, 1 H) 8.40 (br. s., 1 H) 8.47 (d, J = 5.05 Hz, 1 H) 9.55 (s, 1 H) 9.83 (s, 1 H) |
| 15o | HN—[4-chlorophenyl] | M + 1 = 353.1280 | 5.83 | |
| 15p | HN—[2-(1H-indol-3-yl)ethyl] | M + 1 = 386.2098 | 4.44 | |
| 15q | HN—[CH$_2$-(pyridin-3-yl)] | M + 1 = 334.1785 | 3.90 | |
| 15r | HN—[CH$_2$-(pyridin-4-yl)] | M + 1 = 334.1794 | 3.80 | |
| 15s | HN—[2-(morpholin-4-yl)ethyl] | M + 1 = 356.2215 | 3.48 | |
| 15t | HN—[2-(1H-imidazol-4-yl)ethyl] | M + 1 = 337.1896 | 3.53 | |

TABLE 3-continued
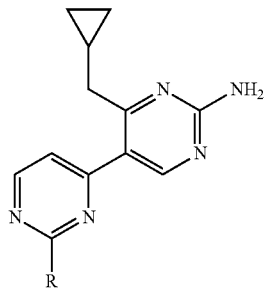
15
| Example | R | HRMS (ES+ m/z) | HPLC $t_R$ (min) | 1H NMR |
|---|---|---|---|---|
| 15u | HN—⟨⟩—NH$_2$ | M + 1 = 334.1782 | 2.50 | (400 MHz, DMSO-d$_6$) δ ppm 0.00-0.04 (m, 2 H) 0.30-0.35 (m, 2 H) 0.93-1.01 (m, 1 H) 2.76 (d, J = 6.57 Hz, 2 H) 4.77 (br. s., 2 H) 6.50 (d, J = 8.59 Hz, 2 H) 6.83 (d, J = 5.05 Hz, 1 H) 6.90 (s, 2 H) 7.28 (d, J = 8.59 Hz, 2 H) 8.32 (s, 1 H) 8.35 (d, J = 5.56 Hz, 1 H) 9.05 (s, 1 H) |
| 15v | HN—pyridyl-Cl | M + 1 = 354.1244 | 4.95 | |
| 15w | HN—(2-methylindol-5-yl) | M + 1 = 372.1954 | 4.49 | (400 MHz, DMSO-d$_6$) δ ppm 0.00-0.04 (m, 2 H) 0.29-0.34 (m, 2 H) 0.94-1.02 (m, 1 H) 2.35 (s, 3 H) 2.78 (d, J = 6.57 Hz, 2 H) 6.85-6.89 (m, 3 H) 7.15 (d, J = 8.59 Hz, 1 H) 7.21 (dd, J = 8.59, 2.02 Hz, 1 H) 7.74 (s, 1 H) 8.34 (s, 1 H) 8.40 (d, J = 5.05 Hz, 1 H) 9.21 (s, 1 H) 10.71 (s, 1 H) |
| 15x | HN—⟨⟩—CN | M + 1 = 344.1626 | 5.11 | (400 MHz, DMSO-d$_6$) δ ppm 0.00-0.03 (m, 2 H) 0.30-0.36 (m, 2 H) 0.92-1.02 (m, 1 H) 2.79 (d, J = 7.07 Hz, 2 H) 6.97 (s, 2 H) 7.14 (d, J = 5.05 Hz, 1 H) 7.73 (d, J = 9.09 Hz, 2 H) 7.98 (d, J = 9.09 Hz, 2 H) 8.39 (s, 1 H) 8.57 (d, J = 5.56 Hz, 1 H) 10.18 (s, 1 H) |
| 15y | HN—⟨⟩—N(CH$_3$)$_2$ | M + 1 = 362.2092 | 3.65 | |

Preparation of intermediate 1-(4'-(Cyclopropylmethyl)-2-(methylthio)-4,5'-bipyrimidin-2'-ylamino)-2-methylpropan-2-ol (4-3)

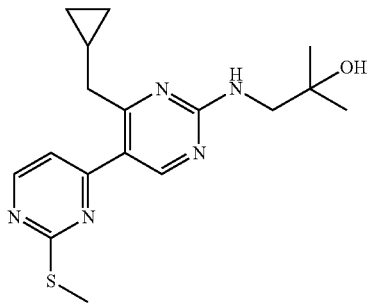 [SMILES: CSc1nccc(-c2cnc(NCC(C)(C)O)nc2CC2CC2)n1]

To a solution of (Z)-1-cyclopropyl-4-(dimethylamino)-3-(2-(methylthio)pyrimidin-4-yl)but-3-en-2-one (3) in DMF (4 mL), 1-(2-hydroxy-2-methylpropyl)guanidine (529 mg, 3.15 mmol) and potassium carbonate (872 mg, 6.31 mmol) were added, and the reaction mixture was stirred at 120° C. for 2 h. The reaction mixture was purified by a reverse-phase Gilson HPLC [30-90% organic phase over 15 min] followed by a Biotage silica gel chromatography [10 g SNAP column, 100% DCM to 12% MeOH/DCM] to obtain the desired product as a glassy solid (90 mg, 21% yield). MS (ES+): m/z=392.2/393.2/394.3 (100/40/10) [MH$^+$]. HPLC: $t_R$=1.12 min over 3 min. Purity: 100% [HPLC (LC/MS) at 220 nm].

Preparation of intermediate 1-(4'-(cyclopropylmethyl)-2-(methylsulfinyl)-4,5'-bipyrimidin-2'-ylamino)-2-methylpropan-2-ol (5-3)

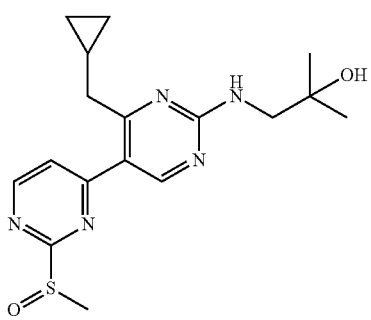

(5-3)

To a solution of 1-(4'-(Cyclopropylmethyl)-2-(methylthio)-4,5'-bipyrimidin-2'-ylamino)-2-methylpropan-2-ol (90 mg, 0.261 mmol) in DCM (521 μl), mCPBA (70.6 mg, 0.287 mmol) was added in portions, and the reaction mixture was stirred at rt for 1 h. The crude product was purified by a Biotage silica gel chromatography [10 g SNAP column, 100% DCM to 12% MeOH/DCM] to obtain the desired product as a yellow solid (38 mg, 40% yield). MS (ES+):m/z=362.2 (100) [MH$^+$]. HPLC: $t_R$=0.90 min over 3 min. Purity: 100% [HPLC (LC/MS) at 220 nm].

1-(2-(2-chloropyridin-4-ylamino)-4'-(cyclopropylmethyl)-4,5'-bipyrimidin-2'-ylamino)-2-methylpropan-2-ol (16a)

To a solution of 4-amino-2-chloropyridine (53.3 mg, 0.415 mmol) in THF (277 μl) cooled to −78° C. under nitrogen, LiHMDS (415 μl, 0.415 mmol) was added dropwise. The reaction mixture was warmed up to rt, then was stirred for 30 min. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 h. According to LC/MS, the reaction was complete. The crude product was purified by reverse-phase HPLC [30-100% organic phase over 15 min] followed by Biotage silica gel chromatography [10 g SNAP column, 100% DCM to 12% MeOH/DCM] to obtain the desired product (29 mg, 49%).

4-(4'-(cyclopropylmethyl)-2'-(2-hydroxy-2-methylpropylamino)-4,5'-bipyrimidin-2-ylamino)benzonitrile (16b)

To a solution of 4-aminobenzonitrile (16.34 mg, 0.138 mmol) in THF (277 μl) cooled to −78° C. under nitrogen, LiHMDS (415 μl, 0.415 mmol) was added dropwise. The reaction mixture was warmed up to rt, then was stirred for 30 min. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 h. According to LC/MS, the reaction was complete. The crude product was purified by reverse-phase HPLC [30-100% organic phase over 15 min] followed by Biotage silica gel chromatography [10 g SNAP column, 100% DCM to 12% MeOH/DCM] to obtain the desired product (16 mg, 28%).

1-(4'-(cyclopropylmethyl)-2-(4-(methylsulfonyl)phenylamino)-4,5'-bipyrimidin-2'-ylamino)-2-methylpropan-2-ol (16d)

To a solution of 4-sulfonylaniline (71.1 mg, 0.415 mmol) in THF (277 μl) cooled to −78° C. under nitrogen, LiHMDS (69.4 mg, 0.415 mmol) was added dropwise. The reaction mixture was warmed up to rt, then was stirred for 30 min. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 h. According to LC/MS, the reaction was complete. The crude product was purified by reverse-phase HPLC [30-100% organic phase over 15 min] followed by Biotage silica gel chromatography [10 g SNAP column, 100% DCM to 12% MeOH/DCM] to obtain the desired product (11 mg, 17%).

TABLE 4

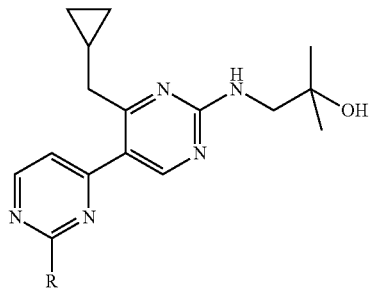

16

| Example | R | HRMS (ES+ m/z) | HPLC t$_R$ (min) | 1H NMR |
|---|---|---|---|---|
| 16a | [4-amino-2-chloropyridin-4-yl] | M + 1 = 426.1819 | 5.57 | (400 MHz, DMSO-d$_6$) δ ppm 0.05 (br. s., 2 H) 0.37 (d, J = 6.57 Hz, 2 H) 0.97 (br. s., 1 H) 1.08 (d, J = 7.07 Hz, 1 H) 1.13 (s, 7 H) 2.83 (d, J = 7.07 Hz, 2 H) 3.39 (d, J = 3.54 Hz, 2 H) 4.57 (s, 1 H) 7.17 (br. s., 1 H) 7.23 (d, J = 5.05 Hz, 2 H) 7.64-7.73 (m, 1 H) 8.01 (s, 1 H) 8.17 (d, J = 5.56 Hz, 1 H) 8.45 (s, 1 H) 8.63 (d, J = 5.05 Hz, 1 H) 10.35 (s, 1 H) |
| 16b | [4-amino-4-cyanophenyl] | M + 1 = 416.2200 | 5.71 | (400 MHz, DMSO-d$_6$) δ ppm 0.04 (br. s., 2 H) 0.35 (d, J = 7.07 Hz, 2 H) 0.99 (d, J = 14.15 Hz, 1 H) 1.13 (s, 6 H) 2.81 (d, J = 6.57 Hz, 2 H) 3.38 (d, J = 5.56 Hz, 2 H) 4.57 (br. s., 1 H) 7.15 (d, J = 5.05 Hz, 1 H) 7.22 (br. s., 1 H) 7.73 (m, J = 9.09 Hz, 2 H) 7.98 (m, J = 8.59 Hz, 2 H) 8.43 (s, 1 H) 8.58 (d, J = 5.05 Hz, 1 H) 10.17 (s, 1 H) |
| 16c | [4-amino-4-fluorophenyl] | M + 1 = 409.2154 | 6.09 | (400 MHz, DMSO-d$_6$) δ ppm 0.04 (br. s., 2 H) 0.35 (d, J = 7.07 Hz, 2 H) 0.89-1.07 (m, 1 H) 1.12 (s, 6 H) 2.79 (d, J = 6.57 Hz, 2 H) 3.37 (d, J = 5.56 Hz, 2 H) 4.57 (br. s., 1 H) 6.99 (d, J = 5.05 Hz, 1 H) 7.12 (t, J = 8.84 Hz, 2 H) 7.14-7.22 (m, 1 H) 7.74 (dd, J = 9.09, 5.05 Hz, 2 H) 8.40 (s, 1 H) 8.47 (d, J = 5.05 Hz, 1 H) 9.59 (s, 1 H) |
| 16d | [4-amino-4-methylsulfonylphenyl] | M + 1 = 469.2026 | 5.01 | (400 MHz, MeOD) δ ppm 0.09 (d, J = 4.55 Hz, 2 H) 0.36-0.48 (m, 2 H) 1.08 (d, J = 13.14 Hz, 1 H) 1.21-1.30 (m, 6 H) 2.88 (d, J = 6.57 Hz, 2 H) 3.05-3.13 (m, 3 H) 3.52 (s, 2 H) 7.06 (d, J = 5.56 Hz, 1 H) 7.84 (m, J = 8.59 Hz, 2 H) 8.01 (m, J = 9.09 Hz, 2 H) 8.44 (s, 1 H) 8.53 (d, J = 5.05 Hz, 1 H) |
| 16e | [4-amino-4-chlorophenyl] | M + 1 = 425.1857 | 6.47 | (400 MHz, MeOD) δ ppm 0.02-0.15 (m, 2 H) 0.29-0.51 (m, 2 H) 0.96-1.16 (m, 1 H) 1.16-1.34 (m, 6 H) 2.85 (d, J = 7.07 Hz, 2 H) 3.51 (s, 2 H) 6.94 (d, J = 5.05 Hz, 1 H) 7.26 (m, J = 8.59 Hz, 2 H) 7.68 (m, J = 9.09 Hz, 2 H) 8.40 (s, 1 H) 8.43 (d, J = 5.56 Hz, 1 H) |

| Example | R | HRMS (ES+ m/z) | HPLC $t_R$ (min) | 1H NMR |
|---|---|---|---|---|
| 16f | | M + 1 = 448.2443 | 4.41 | (400 MHz, DMSO-$d_6$) δ ppm 0.06 (d, J = 2.53 Hz, 2 H) 0.36 (d, J = 7.58 Hz, 2 H) 1.13 (s, 6 H) 2.01 (s, 3 H) 2.82 (d, J = 7.07 Hz, 2 H) 3.38 (br. s., 2 H) 6.97 (d, J = 5.05 Hz, 1 H) 7.27 (d, J = 8.59 Hz, 1 H) 7.47 (d, J = 9.09 Hz, 2 H) 7.61 (d, J = 8.59 Hz, 2 H) 8.43 (s, 1 H) 8.45 (d, J = 5.05 Hz, 1 H) 9.50 (s, 1 H) 9.80 (s, 1 H) |
| 16g | | M + 1 = 490.2603 | 3.82 | (400 MHz, DMSO-$d_6$) δ ppm 0.13 (d, J = 10.61 Hz, 2 H) 0.39 (d, J = 7.07 Hz, 2 H) 0.96-1.17 (m, 8 H) 1.19-1.47 (m, 4 H) 1.92 (d, J = 10.11 Hz, 4 H) 2.80 (br. s., 2 H) 2.91 (s, 3 H) 3.08 (d, J = 2.02 Hz, 1 H) 3.67 (br. s., 1 H) 4.58 (br. s., 1 H) 6.71 (d, J = 5.05 Hz, 1 H) 6.93-7.19 (m, 3 H) 8.25 (d, J = 5.05 Hz, 1 H) 8.36 (br. s., 1 H) |

Example 7

Preparation of 1-Cyclopropyl-3-[2-(methylsulfinyl)pyrimidin-4-yl]propan-2-one (7)

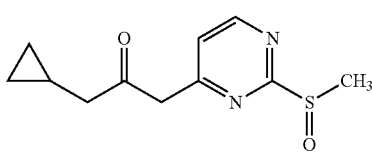

(7)

To a solution of 1-cyclopropyl-3-[2-(methylsulfanyl)pyrimidin-4-yl]propan-2-one (2) (3.00 g, 13.49 mmol) in DCM (54.0 mL) at rt, mCPBA (3.99 g, 16.19 mmol) was added in portions. The reaction mixture was stirred at rt for 1 hour. The reaction was partitioned between saturated sodium carbonate solution and DCM and the aqueous layer was back-extracted. The organic extracts were combined, washed with brine, dried over sodium sulfate, then concentrated in vacuo. The crude product was purified by Biotage™ silica gel chromatography [100% DCM to 5% MeOH/DCM] to afford the desired product as a viscous yellow oil (1.88 g, 58.5% yield), which was still contaminated with residual m-chlorobenzoic acid and carried on to the next step. MS (ES+): m/z=239.2 (100) [MH$^{+2}$]. HPLC: $t_R$=0.73 minute over 3 minutes. Purity: 67.7% [HPLC (LC/MS) at 220 nm].

Example 8

Preparation of 1-Cyclopropyl-3-[2-(pyridin-4-ylamino)pyrimidin-4-yl]propan-2-one (8)

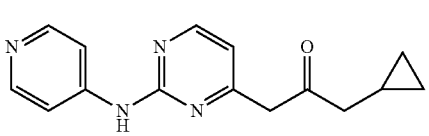

(8)

To a solution of 4-aminopyridine (328 mg, 3.49 mmol) in THF (2.344 mL) cooled to −78° C. was added LHMDS (583 mg, 3.49 mmol). The reaction was warmed to rt and stirred for 15 minutes. The reaction was again cooled to −78° C. and 1-cyclopropyl-3-[2-(methylsulfinyl)pyrimidin-4-yl]propan-2-one (7) (277 mg, 1.162 mmol) was added as a solution in THF (2 mL). The reaction was warmed to rt and stirred for 1 hour. The reaction was quenched by slow addition of saturated ammonium chloride and the volatiles evaporated. The residue was then partitioned between water and DCM. The organic layer was washed with brine, dried with sodium sulfate, and concentrated in vacuo. The crude residue was purified by Biotage™ silica gel chromatography [2-10% MeOH in DCM with 1% triethylamine] to afford the desired product as a yellow oil (269 mg, 86%). MS (ES+): m/z=269.2 (100) [MH$^{+2}$]. HPLC: $t_R$=0.69 minute over 3 minutes. Purity: >95% [HPLC (LC/MS) at 220 nm].

Example 9

Preparation of (3Z)-1-Cyclopropyl-4-(dimethylamino)-3-[2-(pyridin-4-ylamino)pyrimidin-4-yl]but-3-en-2-one (9)

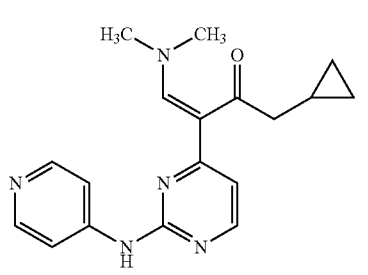

(9)

1-Cyclopropyl-3-[2-(pyridin-4-ylamino)pyrimidin-4-yl]propan-2-one (8) (269 mg, 1.003 mmol) was taken up in DMF-DMA (5.369 mL, 40.1 mmol) and stirred at 80° C. for 30 minutes. The solvent was evaporated and the residue partitioned between DCM and water. The organic layer was washed with saturated sodium bicarbonate and brine, dried with sodium sulfate, and concentrated in vacuo. The crude residue was purified by Biotage™ silica gel chromatography [1-13% MeOH in DCM with 1% triethylamine] to afford the desired product as an orange/brown foam (320 mg, 99% yield). MS (ES+): m/z=324.3 (100) [MH$^{+2}$]. HPLC: $t_R$=0.88 minute over 3 minutes. Purity: >90% [HPLC (LC/MS) at 220 nm].

Examples 10a-10v

General method for synthesis of 4'-(cyclopropylmethyl)-N$^2$-pyridin-4-yl-4,5'-bipyrimidine-2,2'-diamines 10a-v Preparation of 4'-Cyclopropylmethyl-N$^2$-pyridin-4-yl-[4,5']bipyrimidinyl-2,2'-diamine (10a)

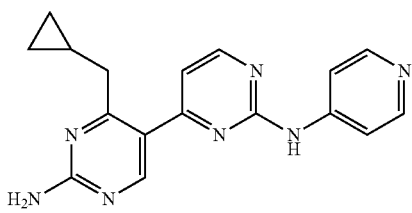

(10a)

To a solution of (3Z)-1-cyclopropyl-4-(dimethylamino)-3-[2-(pyridin-4-ylamino)pyrimidin-4-yl]but-3-en-2-one (9) (80 mg, 0.247 mmol) in DMF (2061 μl), Guanidine HCl (35.3 mg, 0.371 mmol) and potassium carbonate (103 mg, 0.742 mmol) were added and the reaction was heated at 60° C. for 4 hours. The crude product was purified by reverse-phase HPLC [30-90% organic phase over 15 minutes] followed by Biotage™ silica gel chromatography [10 g SNAP column, 100% DCM to 12% MeOH/DCM] to obtain the desired product as a white solid (24.72 mg, 31.3% yield). $^1$H NMR (400 MHz, MeOD) δ ppm 0.01-0.14 (m, 2H) 0.39 (q, J=6.06 Hz, 2H) 0.94-1.10 (m, 1H) 2.87 (d, J=7.07 Hz, 2H) 7.10 (d, J=5.05 Hz, 1H) 7.83 (d, J=6.57 Hz, 2H) 8.30 (d, J=6.57 Hz, 2H) 8.41 (s, 1H) 8.57 (d, J=5.05 Hz, 1H). HRMS (ES+) for C17H17N7.H$^+$ [MH$^+$]: calcd, 320.1624; found, 320.1636. UV-LC: 100% UV purity at 254/214 nm; $t_R$=4.67 minute over 7.75 minutes.

Preparation of N2'-cyclopentyl-4'-(cyclopropylmethyl)-N2-(pyridin-4-yl)-4,5'-bipyrimidine-2,2'-diamine (10e)

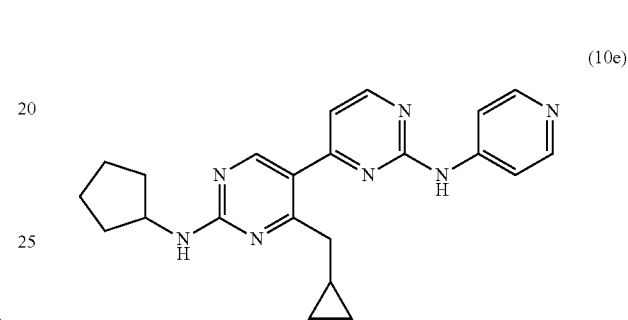

(10e)

To a solution of tert-butyl(tert-butoxycarbonylamino)(cyclopentylamino)methylenecarbamate (74.3 mg, 0.186 mmol) in DCM (515 μl), TFA (143 μl, 1.855 mmol) was added dropwise, and the reaction mixture was stirred at rt. After 2 hours the Boc deprotection was only ~50% complete and additional TFA (143 μl, 1.855 mmol) was added. The reaction mixture was stirred at rt for an additional 2 hours, after which time the deprotection was complete by LC/MS to give the Boc-deprotected intermediate (MW=127.1906). The reaction mixture was concentrated in vacuo, rinsed twice with diethyl ether, then taken up in DMF (515 μl). To the reaction mixture, (Z)-1-cyclopropyl-4-(dimethylamino)-3-(2-(pyridin-4-ylamino)pyrimidin-4-yl)but-3-en-2-one (9) (40 mg, 0.124 mmol) and potassium carbonate (68.4 mg, 0.495 mmol) were added, and the reaction mixture was stirred at 60° C. for 4 h followed by 40° C. for 18 hours. The crude product was purified by reverse-phase HPLC [30-90% organic phase over 15 minutes] followed by Biotage™ silica gel chromatography to obtain the desired product (16.1 mg, 32%).

Preparation of (S)-1-[4'-Cyclopropylmethyl-2-(pyridin-4-ylamino)-[4,5']bipyrimidinyl-2'-ylamino]-propan-2-ol (10k)

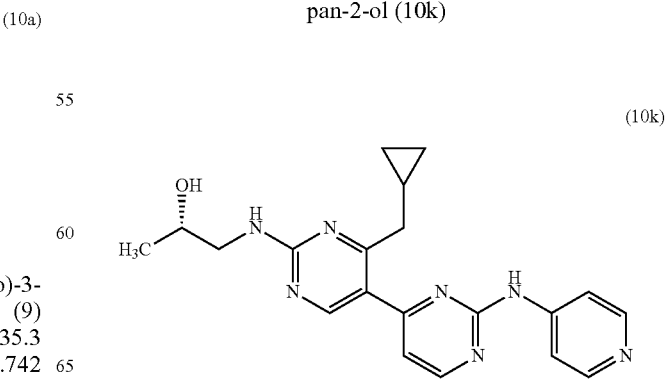

(10k)

To a solution of (Z)-1-cyclopropyl-4-(dimethylamino)-3-(2-(pyridin-4-ylamino)pyrimidin-4-yl)but-3-en-2-one (9) (50 mg, 0.155 mmol) in DMF (1288 µl), (S)-1-(2-hydroxypropyl)guanidine (18.11 mg, 0.115 mmol), and potassium carbonate (64.1 mg, 0.464 mmol) were added, and the reaction mixture was stirred at 90° C. for 3 hours. The crude product was purified by reverse-phase HPLC [30-90% organic phase over 15 minutes] followed by Biotage™ silica gel chromatography [10 g SNAP column, 100% DCM to 12% MeOH/DCM] to obtain the desired product (19.76 mg, 33%).

Preparation of 2-(4'-(cyclopropylmethyl)-2-(pyridin-4-ylamino)-4,5'-bipyrimidin-2'-ylamino)ethanol (10m)

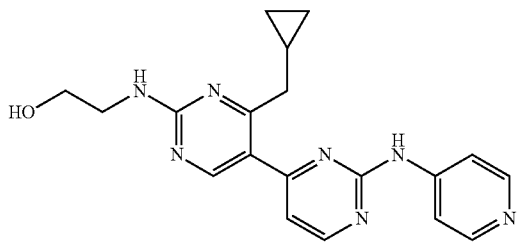

(10m)

To a solution (3Z)-1-cyclopropyl-4-(dimethylamino)-3-[2-(pyridin-4-ylamino)pyrimidin-4-yl]but-3-en-2-one (9) (50 mg, 0.155 mmol) in DMF (1288 µl), 1-(2-hydroxyethyl)guanidine (23.92 mg, 0.232 mmol) and potassium carbonate (107 mg, 0.773 mmol) were added dropwise, and the reaction mixture was stirred at 120° C. for 2 hours. The crude product was purified by reverse-phase HPLC [30-90% organic phase over 15 minutes] followed by Biotage™ silica gel chromatography [10 g SNAP column, 100% DCM to 12% MeOH/DCM] to obtain the desired product (9.13 mg, 16.3%).

Preparation of (S)-2-(4'-(cyclopropylmethyl)-2-(pyridin-4-ylamino)-4,5'-bipyrimidin-2'-ylamino)propan-1-ol (10q)

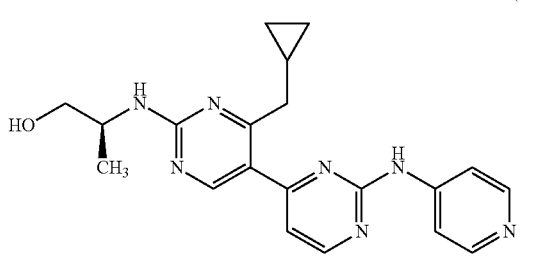

(10q)

To a solution of (Z)-1-cyclopropyl-4-(dimethylamino)-3-(2-(pyridin-4-ylamino)pyrimidin-4-yl)but-3-en-2-one (9) (50 mg, 0.155 mmol) in DMF (541 µl), (S)-1-(1-hydroxypropan-2-yl)guanidine (147 mg, 0.773 mmol) and potassium carbonate (214 mg, 1.546 mmol) were added, and the reaction mixture was stirred at 90° C. for 3 hours. The crude product was purified by reverse-phase HPLC [30-90% organic phase over 15 minutes] followed by Biotage™ silica gel chroma-tography [10 g SNAP column, 100% DCM to 12% MeOH/DCM] to obtain the desired product (23.9 mg, 41%).

Preparation of 4'-(cyclopropylmethyl)-N2'-neopentyl-N2-(pyridin-4-yl)-4,5'-bipyrimidine-2,2'-diamine (10r)

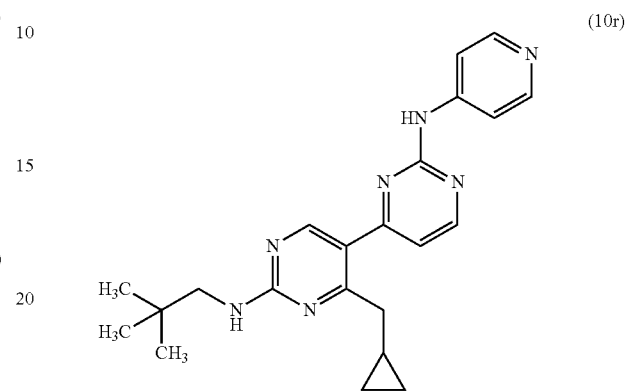

(10r)

To a solution of tert-butyl(tert-butoxycarbonylamino)(neopentylamino)methylenecarbamate (122 mg, 0.371 mmol) in DCM (515 µl), TFA (476 µl, 6.18 mmol) was added dropwise, and the reaction mixture was stirred at rt for 2 hours. The reaction mixture was concentrated in vacuo, rinsed twice with diethyl ether, then taken up in DMF (515 µl). To the reaction mixture, (Z)-1-cyclopropyl-4-(dimethylamino)-3-(2-(pyridin-4-ylamino)pyrimidin-4-yl)but-3-en-2-one (9) (40 mg, 0.124 mmol) and K₂CO₃ (85 mg, 0.618 mmol) were added and the reaction mixture was stirred at 120° C. for 2 hours. The crude products were purified by reverse-phase HPLC [30-90% organic phase over 15 minutes] followed by Biotage™ silica gel chromatography [10 g SNAP column, 100% DCM to 12% MeOH/DCM] to obtain the desired product (18.37 mg, 38%).

Preparation of 1-(4'-(cyclopropylmethyl)-2-(pyridin-4-ylamino)-4,5'-bipyrimidin-2'-ylamino)-2-methylpropan-2-ol (10t)

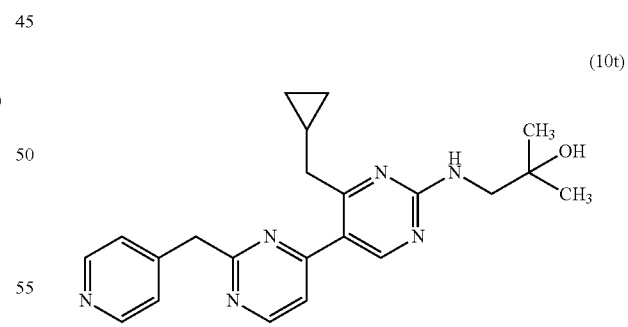

(10t)

To a solution of (Z)-1-cyclopropyl-4-(dimethylamino)-3-(2-(pyridin-4-ylamino)pyrimidin-4-yl)but-3-en-2-one (9) (50 mg, 0.155 mmol) in DMF (1288 µl), 1-(2-hydroxy-2-methylpropyl)guanidine and potassium carbonate (107 mg, 0.773 mmol) were added and the reaction mixture was stirred at 120° C. for 2 hours. The crude product was purified by reverse-phase HPLC [30-90% organic phase over 15 minutes] followed by Biotage™ silica gel chromatography [10 g SNAP column, 100% DCM to 12% MeOH/DCM] to obtain the desired product (23.8 mg, 39%).

TABLE 5

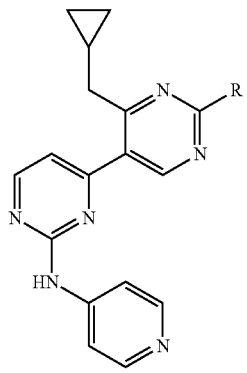

| Example | R | HRMS (ES+ m/z) | HPLC $t_R$ (min) | 1H NMR |
|---|---|---|---|---|
| 10a | NH2 | M + 1 = 320.1636 | 4.67 | (400 MHz, MeOD) δ ppm 0.01-0.14 (m, 2 H) 0.39 (q, J = 6.06 Hz, 2 H) 0.94-1.10 (m, 1 H) 2.87 (d, J = 7.07 Hz, 2 H) 7.10 (d, J = 5.05 Hz, 1 H) 7.83 (d, J = 6.57 Hz, 2 H) 8.30 (d, J = 6.57 Hz, 2 H) 8.41 (s, 1 H) 8.57 (d, J = 5.05 Hz, 1H) |
| 10b | ethylamino | M + 1 = 348.1950 | 3.13 | (400 MHz, MeOD) δ ppm 0.04 (br. s., 2 H) 0.36 (br. s., 2 H) 1.00 (br. s., 1 H) 1.16 (t, J = 7.03 Hz 3 H) 2.82 (d, J = 6.53 Hz, 2 H) 3.37 (d, J = 6.53 Hz, 2 H) 7.16 (d, J = 5.02 Hz, 1 H) 7.55 (t, J = 5.27 Hz, 1 H) 7.77 (d, J = 6.53 Hz, 2 H) 8.35 (d, J = 6.53 Hz, 2 H) 8.44 (s, 1 H) 8.59 (d, J = 5.52 Hz, 1 H) 10.10 (s, 1 H) |
| 10c | benzylamino | M + 1 = 410.2099 | 3.74 | (400 MHz, MeOD) δ ppm 0.05 (q, J = 5.05 Hz, 2 H) 0.26-0.45 (m, 2 H) 0.97-1.11 (m, 1 H) 2.86 (d, J = 7.07 Hz, 2 H) 4.67 (s, 2 H) 7.07 (d, J = 5.05 Hz, 1 H) 7.17-7.25 (m, 1 H) 7.29 (t, J = 7.58 Hz, 2 H) 7.34-7.41 (m, 2 H) 7.82 (d, J = 6.57 Hz, 2 H) 8.29 (d, J = 6.57 Hz, 2 H) 8.42 (s, 1 H) 8.53 (d, J = 5.05 Hz, 1 H) |
| 10d | isobutylamino | M + 1 = 376.2253 | 3.64 | (400 MHz, MeOD) δ ppm 0.03-0.26 (m, 2 H) 0.27-0.55 (m, 2 H) 0.98 (d, J = 6.53 Hz, 6 H) 1.02-1.20 (m, 1 H) 1.85-2.08 (m, 1 H) 2.88 (d, J = 7.03 Hz, 2 H) 3.28 (d, J = 6.02 Hz, 2 H) 7.09 (d, J = 5.02 Hz, 1 H) 7.70-7.96 (m, 2 H) 8.19-8.35 (m, 2 H) 8.41 (s, 1 H) 8.55 (d, J = 5.02 Hz, 1 H) |
| 10e | cyclopentylamino | M + 1 = 388.2248 | 3.74 | (400 MHz, MeOD) δ ppm 0.09 (d, J = 4.02 Hz, 2 H) 0.29-0.51 (m, 2 H) 1.07 (br. s., 1 H) 1.52-1.71 (m, 4 H) 1.72-1.84 (m, 2 H) 2.05 (dt, J = 12.05, 6.02 Hz, 2 H) 2.87 (d, J = 6.53 Hz, 2 H) 4.19-4.43 (m, 1 H) 7.09 (d, J = 5.52 Hz, 1 H) 7.84 (d, J = 6.53 Hz, 2 H) 8.29 (d, J = 6.53 Hz, 2 H) 8.41 (s, 1 H) 8.55 (d, J = 5.02 Hz, 1 H) |
| 10f | cyclobutylamino | M + 1 = 374.2105 | 3.55 | (400 MHz, MeOD) δ ppm 0.09 (d, J = 4.52 Hz, 2 H) 0.31-0.48 (m, 2 H) 1.07 (br. s., 1 H) 1.61-1.89 (m, 2 H) 1.93-2.13 (m, 2 H) 2.30-2.51 (m, 2 H) 2.87 (d, J = 6.53 Hz, 2 H) 4.37-4.62 (m, 1 H) 7.08 (d, J = 5.02 Hz, 1 H) 7.83 (d, J = 7.03 Hz, 2 H) 8.29 (d, J = 6.52 Hz, 2 H) 8.40 (s, 1 H) 8.54 (d, J = 5.52 Hz, 1 H) |

TABLE 5-continued

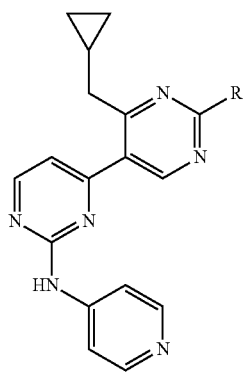

| Example | R | HRMS (ES+ m/z) | HPLC $t_R$ (min) | 1H NMR |
|---|---|---|---|---|
| 10g | (tetrahydropyran-4-yl-NH–) | M + 1 = 404.2197 | 3.12 | (400 MHz, MeOD) δ ppm 0.10 (d, J = 5.02 Hz, 2 H) 0.41 (d, J = 7.53 Hz, 2 H) 0.95-1.19 (m, 1 H) 1.54-1.76 (m, 2 H) 1.95-2.09 (m, 2 H) 2.88 (d, J = 7.03 Hz, 2 H) 3.51-3.63 (m, 2 H) 4.00 (d, J = 11.04 Hz, 2 H) 4.05-4.22 (m, 1 H) 7.10 (d, J = 5.52 Hz, 1 H) 7.84 (d, J = 6.53 Hz, 2 H) 8.30 (d, J = 6.52 Hz, 2 H) 8.43 (s, 1 H) 8.53-8.60 (m, 1 H) |
| 10h | (1-phenylethyl-NH–) | M + 1 = 424.2264 | 3.93 | (400 MHz, DMSO-$d_6$) δ ppm 0.30 (br. s., 8 H) 0.97 (t, J = 7.07 Hz, 4 H) 1.48 (d, J = 7.07 Hz, 12 H) 2.80 (br. s., 7 H) 5.10-5.28 (m, 4 H) 7.12 (d, J = 5.56 Hz, 4 H) 7.15-7.25 (m, 4 H) 7.30 (t, J = 7.58 Hz, 8 H) 7.42 (d, J = 7.58 Hz, 8 H) 7.75 (d, J = 6.06 Hz, 8 H) 8.06 (d, J = 8.08 Hz, 4 H) 8.34 (d, J = 6.06 Hz, 8 H) 8.41 (br. s., 4 H) 8.57 (d, J = 5.05 Hz, 4 H) 10.04 (s, 4 H) |
| 10i | (tert-butyl-NH–) | M + 1 = 376.2248 | 3.81 | (400 MHz, DMSO-$d_6$) δ ppm 0.07 (d, J = 3.54 Hz, 7 H) 0.39 (d, J = 7.07 Hz, 8 H) 1.06 (br. s., 4 H) 1.39 (br. s., 1 H) 1.44 (s, 36 H) 2.84 (d, J = 7.07 Hz, 8 H) 7.10 (s, 4 H) 7.16 (d, J = 5.05 Hz, 4 H) 7.78 (d, J = 6.57 Hz, 8 H) 8.35 (d, J = 6.57 Hz. 8 H) 8.44 (s, 4 H) 8.58 (d, J = 5.05 Hz, 4 H) 10.08 (s, 4H) |
| 10j | (2-hydroxypropyl-NH–) | M + 1 = 378.2050 | 4.23 | (400 MHz, DMSO-$d_6$) δ ppm 0.01-0.13 (m, 2 H) 0.36 (d, J = 6.57 Hz, 2 H) 0.87-1.14 (m, 4 H) 2.82 (d, J = 6.57 Hz, 2 H) 3.85 (d, J = 5.05 Hz, 1 H) 4.70 (d, J = 5.05 Hz, 1 H) 7.15 (d, J = 5.56 Hz, 1 H) 7.36 (t, J = 5.81 Hz, 1 H) 7.77 (d, J = 6.57 Hz, 2 H) 8.35 (d, J = 6.06 Hz, 2 H) 8.44 (s, 1 H) 8.59 (d, J = 5.05 Hz, 1 H) 10.06 (s, 1 H) |
| 10k | ((S)-2-hydroxypropyl-NH–) | M + 1 = 378.2038 | 5.92 | (400 MHz, MeOD) δ ppm 0.09 (d, J = 5.05 Hz, 2 H) 0.33-0.48 (m, 2 H) 1.06 (d, J = 6.06 Hz, 1 H) 1.22 (d, J = 6.06 Hz, 3 H) 2.88 (d, J = 7.07 Hz, 2 H) 3.39 (dd, J = 13.64, 7.07 Hz, 1 H) 3.54 (dd, J = 13.64, 4.55 Hz, 1 H) 3.92-4.10 (m, 1 H) 7.09 (d, J = 5.05 Hz, 1 H) 7.83 (d, J = 6.57 Hz, 2 H) 8.30 (d, J = 6.57 Hz, 2 H) 8.43 (s, 1 H) 8.55 (d, J = 5.05 Hz, 1 H) |

TABLE 5-continued

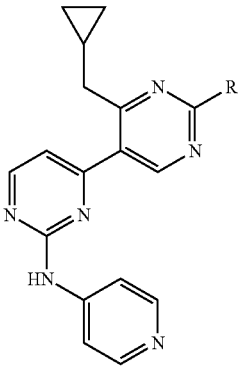

| Example | R | HRMS (ES+ m/z) | HPLC $t_R$ (min) | 1H NMR |
|---|---|---|---|---|
| 10l | 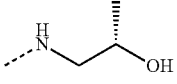 | M + 1 = 378.2048 | 2.86 | (400 MHz, MeOD) δ ppm 0.09 (d, J = 5.05 Hz, 2 H) 0.34-0.49 (m, 2 H) 1.06 (d, J = 6.06 Hz, 1 H) 1.22 (d, J = 6.57 Hz, 3 H) 2.88 (d, J = 7.07 Hz, 2 H) 3.33-3.45 (m, 2 H) 3.50-3.63 (m, 1 H) 3.90-4.09 (m, 1 H) 7.10 (d, J = 5.05 Hz, 1 H) 7.83 (d, J = 6.57 Hz, 2 H) 8.30 (d, J = 6.57 Hz, 2 H) 8.43 (s, 1 H) 8.56 (d, J = 5.56 Hz, 1 H) |
| 10m | 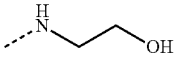 | M + 1 = 364.1884 | 2.70 | (400 MHz, MeOD) δ ppm 0.05-0.17 (m, 2 H) 0.35-0.49 (m, 2 H) 1.06 (d, J = 5.05 Hz, 1 H) 2.89 (d, J = 7.07 Hz, 2 H) 3.60 (t, J = 5.81 Hz, 2 H) 3.75 (t, J = 5.81 Hz, 2 H) 7.10 (d, J = 5.05 Hz, 1 H) 7.83 (d, J = 6.57 Hz, 2 H) 8.30 (d, J = 6.57 Hz, 2 H) 8.44 (s, 1 H) 8.56 (d, J = 5.05 Hz, 1 H) |
| 10n |  | M + 1 = 378.2036 | 4.85 | (400 MHz, DMSO-$d_6$) δ ppm 0.03 (br. s., 2 H) 0.36 (br. s., 2H) 0.90-1.11 (m, 1 H) 2.82 (d, J = 6.53 Hz, 2 H) 3.23-3.30 (m, 3 H) 3.50 (br. s., 4 H) 7.16 (d, J = 5.52 Hz, 1 H) 7.47-7.59 (m, 1 H) 7.77 (d, J = 6.02 Hz, 2 H) 8.30-8.40 (m, 2 H) 8.45 (s, 1 H) 8.59 (d, J = 5.02 Hz, 1 H) 10.11 (s, 1 H) |
| 10o | 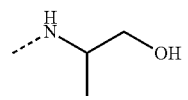 | M + 1 = 378.2051 | 4.44 | (400 MHz, DMSO-$d_6$) δ ppm 0.03 (d, J = 5.52 Hz, 2 H) 0.15 (s, 2 H) 0.36 (d, J = 6.02 Hz, 1 H) 1.00 (d, J = 5.52 Hz, 1 H) 1.16 (d, J = 6.53 Hz, 3 H) 2.82 (d, J = 6.53 Hz, 2 H) 3.44-3.59 (m, 1 H) 3.98-4.16 (m, 1 H) 4.71 (t, J = 5.77 Hz, 1 H) 7.16 (d, J = 5.02 Hz, 1 H) 7.77 (d, J = 6.53 Hz, 2 H) 8.35 (d, J = 6.02 Hz, 2 H) 8.44 (s, 1H) 8.59 (d, J = 5.02 Hz, 1 H) 10.10 (s, 1 H) |
| 10p | 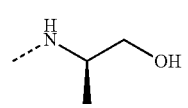 | M + 1 = 378.2044 | 5.99 | (400 MHz, DMSO-$d_6$) δ ppm 0.01-0.13 (m, 2 H) 0.36 (d, J = 7.58 Hz, 2 H) 0.92-1.06 (m, 1 H) 1.16 (d, J = 6.57 Hz, 3 H) 2.82 (d, J = 7.07 Hz, 2 H) 3.33-3.44 (m, 1 H) 3.44-3.60 (m, 1 H) 3.95-4.15 (m, 1 H) 4.68 (t, J = 5.81 Hz, 1 H) 7.09-7.24 (m, 2 H) 7.77 (d, J = 6.57 Hz, 2 H) 8.35 (d, J = 6.57 Hz, 2 H) 8.44 (s, 1 H) 8.58 (d, J = 5.05 Hz, 1 H) 10.06 (s, 1 H) |

TABLE 5-continued

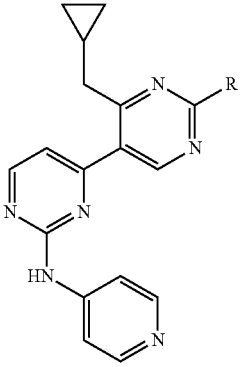

| Example | R | HRMS (ES+ m/z) | HPLC $t_R$ (min) | 1H NMR |
|---|---|---|---|---|
| 10q | 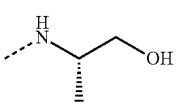 | M + 1 = 378.2056 | 5.98 | (400 MHz, DMSO-d$_6$) δ ppm 0.00-0.14 (m, 2 H) 0.36 (d, J = 7.07 Hz, 2 H) 0.93-1.06 (m, 1 H) 1.16 (d, J = 6.57 Hz, 3 H) 2.82 (d, J = 7.07 Hz, 2 H) 3.32-3.39 (m, 1 H) 3.52 (d, J = 5.05 Hz, 1 H) 3.95-4.14 (m, 1 H) 4.68 (t, J = 5.81 Hz, 1 H) 7.09-7.26 (m, 2 H) 7.77 (d, J = 6.57 Hz, 2 H) 8.35 (d, J = 6.57 Hz, 2 H) 8.44 (s, 1 H) 8.58 (d, J = 5.05 Hz, 1 H) 10.06 (s, 1 H) |
| 10r | 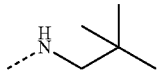 | M + 1 = 390.2398 | 3.89 | (400 MHz, DMSO-d$_6$) δ ppm 0.07 (br. s., 2 H) 0.36 (br. s., 2 H) 0.92 (s, 9 H) 1.07 (br. s., 1 H) 2.83 (d, J = 7.03 Hz, 2 H) 3.27 (br. s., 2 H) 7.16 (d, J = 5.02 Hz, 1 H) 7.55 (br. s., 1 H) 7.77 (d, J = 6.53 Hz, 2 H) 8.35 (d, J = 6.02 Hz, 2 H) 8.43 (s, 1 H) 8.58 (d, J = 5.02 Hz, 1 H) 10.09 (s, 1 H) |
| 10s | 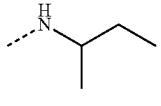 | M + 1 = 376.2258 | 3.65 | (400 MHz, DMSO-d$_6$) δ ppm 0.15 (s, 2 H) 0.36 (br. s., 2 H) 0.89 (t, J = 7.28 Hz, 3 H) 1.04 (br. s., 1 H) 1.15 (d, J = 6.02 Hz, 3 H) 1.41-1.70 (m, 2 H) 2.75-2.90 (m, 2 H) 3.97 (br. s., 1 H) 7.16 (d, J = 5.02 Hz, 1 H) 7.40 (br. s., 1 H) 7.78 (d, J = 6.53 Hz, 2 H) 8.36 (d, J = 6.02 Hz, 2 H) 8.43 (s, 1 H) 8.59 (d, J = 5.02 Hz, 1 H) 10.11 (s, 1 H) |
| 10t | 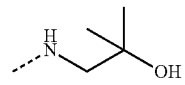 | M + 1 = 392.2211 | 3.02 | (400 MHz, MeOD) δ ppm 0.02-0.18 (m, 2 H) 0.33-0.50 (m, 2 H) 0.97-1.14 (m, 1 H) 1.25 (s, 6 H) 2.89 (d, J = 7.07 Hz, 2 H) 3.52 (s, 2 H) 7.10 (d, J = 5.56 Hz, 1 H) 7.83 (d, J = 6.57 Hz, 2 H) 8.30 (d, J = 6.57 Hz, 2 H) 8.44 (s, 1 H) 8.56 (d, J = 5.05 Hz, 1 H) |

TABLE 5-continued

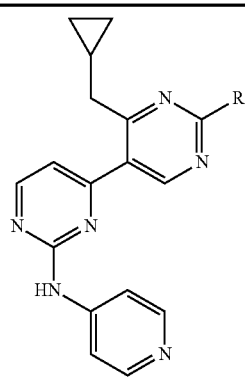

| Example | R | HRMS (ES+ m/z) | HPLC $t_R$ (min) | 1H NMR |
|---------|---|----------------|------------------|--------|
| 10u | ⋯O—  | M + 1 = 335.1621 | 2.96 | (400 MHz, MeOD) δ ppm 0.09-0.14 (m, 2 H) 0.40-0.46 (m, 2 H) 1.03-1.13 (m, 1 H) 2.94 (d, J = 7.07 Hz, 2 H) 4.09 (s, 3 H) 7.16 (d, J = 5.05 Hz, 1 H) 7.83 (d, J = 7.07 Hz, 2 H) 8.30 (d, J = 7.07 Hz, 2 H) 8.63 (d, J = 5.05 Hz, 1 H) 8.65 (s, 1 H) |
| 10v | ⋯H | M + 1 = 305.1513 | 2.50 | (400 MHz, CDCl3) δ ppm 0.12-0.18 (m, 2 H) 0.45-0.52 (m, 2 H) 1.06-1.17 (m, 1 H) 2.92 (d, J = 7.07 Hz, 2H) 7.02 (d, J = 5.05 Hz, 1 H) 7.60 (s, 1 H) 7.65 (d, J = 6.06 Hz, 2 H) 8.49 (s, 2 H) 8.65 (d, J = 5.05 Hz, 1 H) 8.76 (s, 1 H) 9.25 (s, 1 H) |

Example 11

Preparation of 4'-(Cyclopropylmethyl)-2'-(methylsulfanyl)-N-pyridin-4-yl-4,5'-bipyrimidin-2-amine (11)

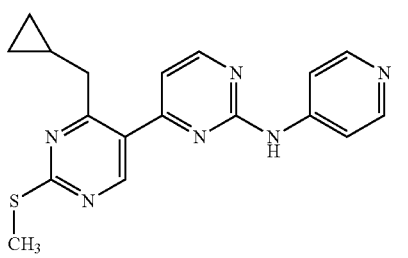

(11)

To a solution of (Z)-1-cyclopropyl-4-(dimethylamino)-3-(2-(pyridin-4-ylamino)pyrimidin-4-yl)but-3-en-2-one (9) (200 mg, 0.618 mmol) in DMF (5.154 ml) was added potassium carbonate (256 mg, 1.855 mmol) and 2-methyl-2-thiopseudourea sulfate (129 mg, 0.928 mmol). The reaction was warmed to 120° C. and stirred for 1 hr. The solvent was evaporated and the crude residue partitioned between DCM and water. The organic layer was washed with brine, dried with sodium sulfate, and concentrated. The crude product was purified by flash chromatography with a gradient of 2-10% MeOH in DCM and further purified reverse phase HPLC with a gradient of 10-100% MeCN in H2O to give 7.8 mg of the desired product as a white solid. HRMS (ES+)=351.1391. UV-LC: 100/100% UV purity at 214/254 nm; HPLC: $t_R$=3.38 minute over 7.75 minutes. 1H NMR (400 MHz, MeOD) δ ppm 0.10-0.14 (m, 2H) 0.41-0.47 (m, 2H) 1.03-1.15 (m, 1H) 2.63 (s, 3H) 2.94 (d, J=7.07 Hz, 2H) 7.18 (d, J=5.56 Hz, 1H) 7.83 (d, J=7.07 Hz, 2H) 8.31 (d, J=7.07 Hz, 2H) 8.64 (s, 1H) 8.65 (d, J=5.05 Hz, 1H)

Example 12a-12c

General method for synthesis of 4'-(cyclopropylmethyl)-N²-pyridin-4-yl-4,5'-bipyrimidine-2,2'-diamines 12a-c Preparation of 4'-Cyclopropylmethyl-N²'-isopropyl-N²-pyridin-4-yl-[4,5']bipyrimidinyl-2,2'-diamine (12a)

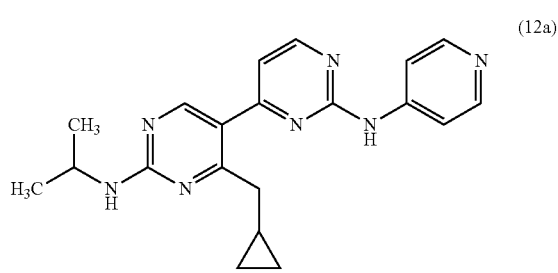 [SMILES: CC(C)Nc1ncc(-c2ccnc(Nc3ccncc3)n2)c(CC2CC2)n1]

(12a)

To a solution of 4'-(cyclopropylmethyl)-2'-(methylsulfanyl)-N-pyridin-4-yl-4,5'-bipyrimidin-2-amine (11) (35 mg, 0.096 mmol) in DMSO (1 mL), isopropylamine (24.55 μl, 0.287 mmol) was added and the reaction was microwaved for 20 minutes at 160° C. The crude product was purified by reverse-phase HPLC [30-100% organic phase over 15 minutes] followed by Biotage™ silica gel chromatography [10 g SNAP column, 100% DCM to 10% MeOH/DCM] to afford the title compound as a pale-yellow solid (13.67 mg, 39.6% yield). 1H NMR (400 MHz, MeOD) δ ppm 0.04-0.17 (m, 2H) 0.31-0.50 (m, 2H) 0.97-1.17 (m, 1H) 1.27 (d, J=6.57 Hz, 6H) 2.88 (d, J=7.07 Hz, 2H) 4.22 (ddd, J=13.01, 6.44, 6.32 Hz, 1H) 7.10 (d, J=5.05 Hz, 1H) 7.84 (d, J=7.07 Hz, 2H) 8.30 (d, J=6.57 Hz, 2H) 8.42 (s, 1H) 8.55 (d, J=5.05 Hz, 1H). HRMS (ES+) for C20H23N7.H⁺ [MH⁺]: calcd, 362.2093; found, 362.2083. UV-LC: 100% UV purity at 254/214 nm; $t_R$=3.39 minutes over 7.75 minutes.

TABLE 6

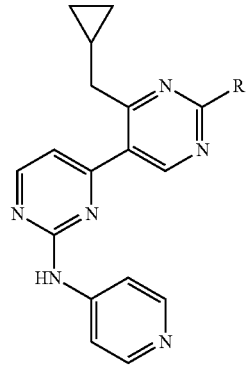

| Example | R | HRMS (ES+ m/z) | HPLC $t_R$ (min) | 1H NMR |
|---|---|---|---|---|
| 12a | ⋯NH-iPr | M + 1 = 362.2083 | 3.39 | (400 MHz, MeOD) δ ppm 0.04-0.17 (m, 2 H) 0.31-0.50 (m, 2 H) 0.97-1.17 (m, 1 H) 1.27 (d, J = 6.57 Hz, 6 H) 2.88 (d, J = 7.07 Hz, 2 H) 4.22 (ddd, J = 13.01, 6.44, 6.32 Hz, 1 H) 7.10 (d, J = 5.05 Hz, 1 H) 7.84 (d, J = 7.07 Hz, 2 H) 8.30 (d, J = 6.57 Hz, 2 H) 8.42 (s, 1 H) 8.55 (d, J = 5.05 Hz, 1 H) |
| 12b | ⋯NH-cyclohexyl | M + 1 = 402.2408 | 3.92 | (400 MHz, MeOD) δ ppm 0.10 (d, J = 5.05 Hz, 2 H) 0.32-0.49 (m, 2 H) 1.05 (d, J = 7.58 Hz, 1 H) 1.21-1.51 (m, 5 H) 1.67 (br. s., 1 H) 1.75-1.89 (m, 2 H) 1.98-2.11 (m, 2 H) 2.87 (d, J = 7.07 Hz, 2 H) 3.88 (br. s., 1 H) 7.09 (d, J = 5.56 Hz, 1 H) 7.83 (d, J = 7.07 Hz, 2 H) 8.30 (d, J = 6.57 Hz, 2 H) 8.41 (s, 1 H) 8.55 (d, J = 5.05 Hz, 1 H) |
| 12c | ⋯NH-cyclopropyl | M + 1 = 360.1941 | 3.07 | (400 MHz, MeOD) δ ppm 0.09 (q, J = 5.05 Hz, 2 H) 0.35-0.45 (m, 2 H) 0.53-0.63 (m, 2 H) 0.75-0.85 (m, 2 H) 1.07 (t, J = 7.07 Hz, 1 H) 2.80 (ddd, J = 6.95, 3.41, 3.28 Hz, 1 H) 2.89 (d, J = 6.57 Hz, 2 H) 7.11 (d, J = 5.05 Hz, 1 H) 7.84 (d, J = 6.57 Hz, 2 H) 8.30 (d, J = 6.57 Hz, 2 H) 8.45 (s, 1 H) 8.57 (d, J = 5.05 Hz, 1 H) |

Examples 16a-16g

General Method for Synthesis of 16a-f

Preparation of 1-(2-(2-chloropyridin-4-ylamino)-4'-(cyclopropylmethyl)-4,5'-bipyrimidin-2'-ylamino)-2-methylpropan-2-ol (16a)

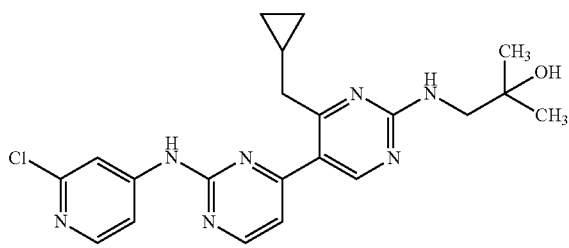

(16a)

To a solution of 4-amino-2-chloropyridine (53.3 mg, 0.415 mmol) in THF (277 µl) cooled to −78° C. under nitrogen, LiHMDS (415 µl, 0.415 mmol) was added dropwise. The reaction mixture was warmed up to rt, then was stirred for 30 minutes. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 hour. According to LC/MS, the reaction was complete. The crude product was purified by reverse-phase HPLC [30-100% organic phase over 15 minutes] followed by Biotage™ silica gel chromatography [10 g SNAP column, 100% DCM to 12% MeOH/DCM] to obtain the desired product (29 mg, 49%).

Preparation of 4-(4'-(cyclopropylmethyl)-2'-(2-hydroxy-2-methylpropylamino)-4,5'-bipyrimidin-2-ylamino)benzonitrile (16b)

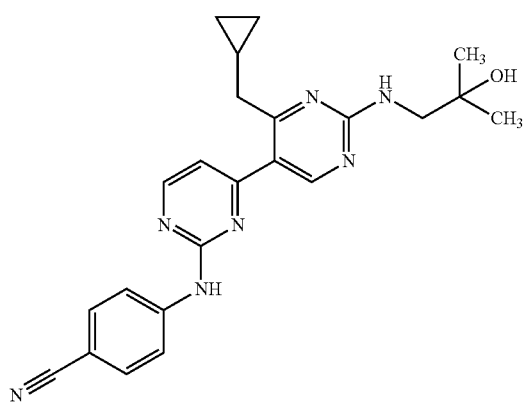

(16b)

To a solution of 4-aminobenzonitrile (16.34 mg, 0.138 mmol) in THF (277 µl) cooled to −78° C. under nitrogen, LiHMDS (415 µl, 0.415 mmol) was added dropwise. The reaction mixture was warmed up to rt, then was stirred for 30 minutes. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 hour. According to LC/MS, the reaction was complete. The crude product was purified by reverse-phase HPLC [30-100% organic phase over 15 minutes] followed by Biotage™ silica gel chromatography [10 g SNAP column, 100% DCM to 12% MeOH/DCM] to obtain the desired product (16 mg, 28%).

Preparation of 1-(4'-(cyclopropylmethyl)-2-(4-(methylsulfonyl)phenylamino)-4,5'-bipyrimidin-2'-ylamino)-2-methylpropan-2-ol (16d)

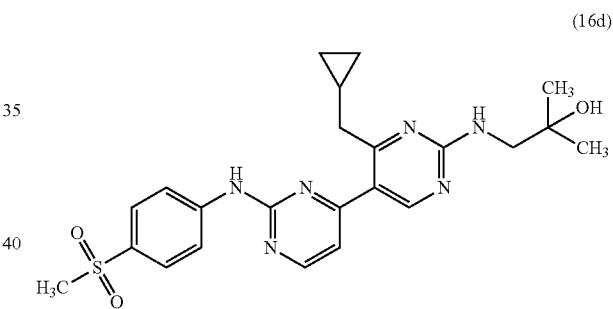

(16d)

To a solution of 4-sulfonylaniline (71.1 mg, 0.415 mmol) in THF (277 µl) cooled to −78° C. under nitrogen, LiHMDS (69.4 mg, 0.415 mmol) was added dropwise. The reaction mixture was warmed up to rt, then was stirred for 30 minutes. To the reaction mixture cooled back to −78° C., 1-(4'-(cyclopropylmethyl)-2-(methylsulfinyl)-4,5'-bipyrimidin-2'-ylamino)-2-methylpropan-2-ol (5-3) (50 mg, 0.138 mmol) was added, and the reaction mixture was warmed up to rt, then was stirred for additional 1 hour. According to LC/MS, the reaction was complete. The crude product was purified by reverse-phase HPLC [30-100% organic phase over 15 minutes] followed by Biotage™ silica gel chromatography [10 g SNAP column, 100% DCM to 12% MeOH/DCM] to obtain the desired product (11 mg, 17%).

The compounds listed in Table 7 below were prepared using the procedures as indicated above using the appropriate starting materials.

TABLE 7

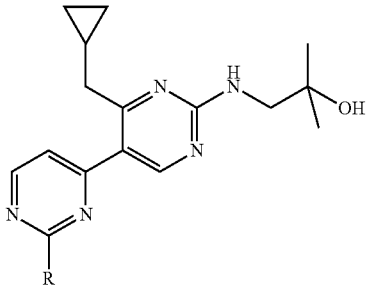

| Example | R | HRMS (ES+ m/z) | HPLC t_R (min) | 1H NMR |
|---|---|---|---|---|
| 16a | 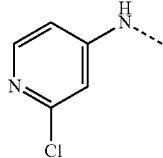 | M + 1 = 426.1819 | 5.57 | (400 MHz, DMSO-$d_6$) δ ppm 0.05 (br. s., 2 H) 0.37 (d, J = 6.57 Hz, 2 H) 0.97 (br. s., 1 H) 1.08 (d, J = 7.07 Hz, 1 H) 1.13 (s, 7 H) 2.83 (d, J = 7.07 Hz, 2 H) 3.39 (d, J = 3.54 Hz, 2 H) 4.57 (s, 1 H) 7.17 (br. s., 1 H) 7.23 (d, J = 5.05 Hz, 2 H) 7.64-7.73 (m, 1 H) 8.01 (s, 1 H) 8.17 (d, J = 5.56 Hz, 1 H) 8.45 (s, 1 H) 8.63 (d, J = 5.05 Hz, 1 H) 10.35 (s, 1 H) |
| 16b | 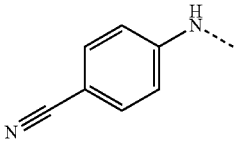 | M + 1 = 416.2200 | 5.71 | (400 MHz, DMSO-$d_6$) δ ppm 0.04 (br. s., 2 H) 0.35 (d, J = 7.07 Hz, 2 H) 0.99 (d, J = 14.15 Hz, 1 H) 1.13 (s, 6 H) 2.81 (d, J = 6.57 Hz, 2 H) 3.38 (d, J = 5.56 Hz, 2 H) 4.57 (br. s., 1 H) 7.15 (d, J = 5.05 Hz, 1 H) 7.22 (br. s., 1 H) 7.73 (m, J = 9.09 Hz, 2 H) 7.98 (m, J = 8.59 Hz, 2 H) 8.43 (s, 1 H) 8.58 (d, J = 5.05 Hz, 1 H) 10.17 (s, 1 H) |
| 16c | 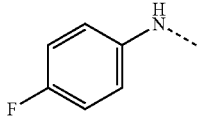 | M + 1 = 409.2154 | 6.09 | (400 MHz, DMSO-$d_6$) δ ppm 0.04 (br. s., 2 H) 0.35 (d, J = 7.07 Hz, 2 H) 0.89-1.07 (m, 1 H) 1.12 (s, 6 H) 2.79 (d, J = 6.57 Hz, 2 H) 3.37 (d, J = 5.56 Hz, 2 H) 4.57 (br. s., 1 H) 6.99 (d, J = 5.05 Hz, 1 H) 7.12 (t, J = 8.84 Hz, 2 H) 7.14-7.22 (m, 1 H) 7.74 (dd, J = 9.09, 5.05 Hz, 2 H) 8.40 (s, 1 H) 8.47 (d, J = 5.05 Hz, 1 H) 9.59 (s, 1 H) |
| 16d | 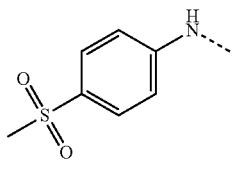 | M + 1 = 469.2026 | 5.01 | (400 MHz, MeOD) δ ppm 0.09 (d, J = 4.55 Hz, 2 H) 0.36-0.48 (m, 2 H) 1.08 (d, J = 13.14 Hz, 1 H) 1.21-1.30 (m, 6 H) 2.88 (d, J = 6.57 Hz, 2 H) 3.05-3.13 (m, 3 H) 3.52 (s, 2 H) 7.06 (d, J = 5.56 Hz, 1 H) 7.84 (m, J = 8.59 Hz, 2 H) 8.01 (m, J = 9.09 Hz, 2 H) 8.44 (s, 1 H) 8.53 (d, J = 5.05 Hz, 1 H) |
| 16e | 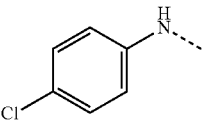 | M + 1 = 425.1857 | 6.47 | (400 MHz, MeOD) δ ppm 0.02-0.15 (m, 2 H) 0.29-0.51 (m, 2 H) 0.96-1.16 (m, 1 H) 1.16-1.34 (m, 6 H) 2.85 (d, J = 7.07 Hz, 2 H) 3.51 (s, 2 H) 6.94 (d, J = 5.05 Hz, 1 H) 7.26 (m, J = 8.59 Hz, 2 H) 7.68 (m, J = 9.09 Hz, 2 H) 8.40 (s, 1 H) 8.43 (d, J = 5.56 Hz, 1 H) |

TABLE 7-continued

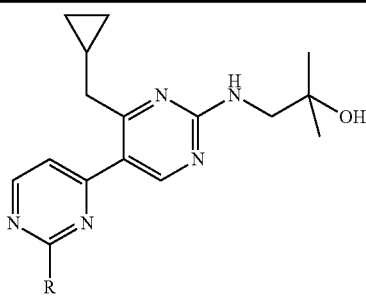

| Example | R | HRMS (ES+ m/z) | HPLC $t_R$ (min) | 1H NMR |
|---|---|---|---|---|
| 16f | 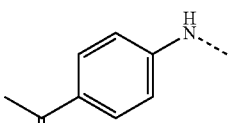 | M + 1 = 448.2443 | 4.41 | (400 MHz, DMSO-$d_6$) δ ppm 0.06 (d, J = 2.53 Hz, 2 H) 0.36 (d, J = 7.58 Hz, 2 H) 1.13 (s, 6 H) 2.01 (s, 3 H) 2.82 (d, J = 7.07 Hz, 2 H) 3.38 (br. s., 2 H) 6.97 (d, J = 5.05 Hz, 1 H) 7.27 (d, J = 8.59 Hz, 1 H) 7.47 (d, J = 9.09 Hz, 2 H) 7.61 (d, J = 8.59 Hz, 2 H) 8.43 (s, 1 H) 8.45 (d, J = 5.05 Hz, 1 H) 9.50 (s, 1 H) 9.80 (s, 1 H) |
| 16g | 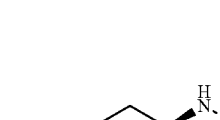 | M + 1 = 490.2603 | 3.82 | (400 MHz, DMSO-$d_6$) δ ppm 0.13 (d, J = 10.61 Hz, 2 H) 0.39 (d, J = 7.07 Hz, 2 H) 0.96-1.17 (m, 8 H) 1.19-1.47 (m, 4 H) 1.92 (d, J = 10.11 Hz, 4 H) 2.80 (br. s., 2 H) 2.91 (s, 3 H) 3.08 (d, J = 2.02 Hz, 1 H) 3.67 (br. s., 1 H) 4.58 (br. s., 1 H) 6.71 (d, J = 5.05 Hz, 1 H) 6.93-7.19 (m, 3 H) 8.25 (d, J = 5.05 Hz, 1 H) 8.36 (br. s., 1 H) |

Preparation of intermediate 1-(2-Methylsulfanyl-pyrimidin-4-yl)-propan-2-one (17)

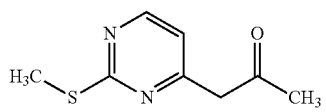
(17)

To a solution of 4-Methyl-2-(methylthio)pyrimidine (1) (3 g, 21.40 mmol) in THF (35.7 mL) at −10° C. was added LHMDS (32.1 mL, 32.1 mmol, 1M in THF). The resulting reaction was warmed to rt and stirred for 15 minutes, after which time the reaction was cooled back to −10° C. and Benzyl Acetate (3.21 mL, 23.54 mmol) was added. The reaction was then warmed to rt and stirred for 1 hour, after which time complete conversion to product was observed by LCMS. TLC after 1 hour still showed the presence of some starting material and the reaction was continued stirring for an additional hour. After this time there was no change in TLC and the reaction was worked up. The reaction was quenched by slow addition of saturated ammonium chloride and the volatile solvent evaporated. The mixture was then diluted with EtOAc and water. The organic layer was then washed with brine, dried with sodium sulfate, and concentrated. The crude residue was purified by flash chromatography with a gradient of 8-66% EtOAc in Heptane to give the desired product as a yellow liquid (1.93 g, 50%). MS (ES+): m/z=183.1 (100) [MH⁺]. HPLC: $t_R$=0.91 minute over 3 minutes. Purity: 76% [HPLC (LC/MS) at 220 nm].

Preparation of intermediate 4-Dimethylamino-3-(2-methylsulfanyl-pyrimidin-4-yl)-but-3-en-2-one (18)

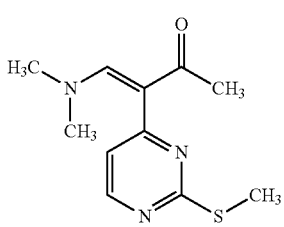
(18)

1-(2-Methylsulfanyl-pyrimidin-4-yl)-propan-2-one (17) (1.93 g, 10.59 mmol) was taken up in DMF-DMA (20 mL, 149 mmol) and the resulting reaction was warmed to 80° C. and stirred for 2 hours. The solvent was evaporated and the crude residue partitioned between DCM and water. The organic layer was washed with brine, dried with sodium sulfate, and concentrated. The crude residue was purified by flash column chromatography with a gradient of 1-12% MeOH in DCM to give the desired product as a brown/orange oil (1.24 g, 49%). MS (ES+): m/z=238.2/239.3 (100/30) [MH+]. HPLC: $t_R$=0.78 minute over 3 minutes. Purity: 100% [HPLC (LC/MS) at 220 nm].

Preparation of intermediate 4'-Methyl-2-methylsulfanyl-[4,5']bipyrimidinyl-2'-ylamine (19)

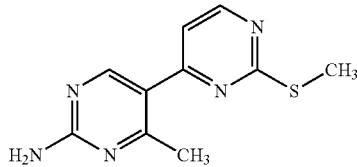
(19)

To a solution of 4-Dimethylamino-3-(2-methylsulfanyl-pyrimidin-4-yl)-but-3-en-2-one (18) (1.02 g, 4.30 mmol) in DMF (14 mL) was added $K_2CO_3$ (1.782 g, 12.89 mmol) and Guanidine HCl (0.616 g, 6.45 mmol) and the resulting suspension was stirred at 120° C. for 1 hour. The DMF was evaporated and the crude residue partitioned between water and ethyl acetate. The organic layer was washed with water and brine, dried with sodium sulfate, and concentrated. The crude residue was purified by flash chromatography with a gradient of 1-12% MeOH in DCM to give the desired product as a light yellow solid (800 mg, 80%). MS (ES+): m/z=234.3/235.4 (100/20) [MH+]. HPLC: $t_R$=1.01 minutes over 3 minutes. Purity: 70% [HPLC (LC/MS) at 220 nm].

Preparation of intermediate 2-Methanesulfinyl-4'-methyl-[4,5']bipyrimidinyl-2'-ylamine (20)

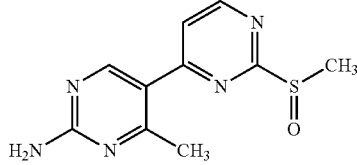
(20)

To a suspension of 4'-Methyl-2-methylsulfanyl-[4,5']bipyrimidinyl-2'-ylamine (19) (380 mg, 1.629 mmol) in DCM (3.258 mL) was added mCPBA (402 mg, 1.629 mmol). The reaction turned to a brown solution, and immediately the reaction was complete. The reaction mixture was diluted with DCM and water. The organic layer was washed with saturated sodium bicarbonate and brine, dried with sodium sulfate, and concentrated. The crude residue was purified by flash chromatography with a gradient of 2-10% MeOH in DCM to give the desired product (70 mg, 17%). MS (ES+): m/z=250.1 (100) [MH+]. HPLC: $t_R$=0.64 minute over 3 minutes.

Example 21

Preparation of 4'-Methyl-$N^2$-pyridin-4-yl-[4,5']bipyrimidinyl-2,2'-diamine (21)

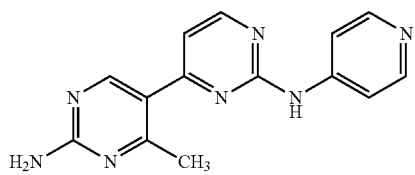
(21)

To a solution of 4-aminopyridine (423 mg, 4.49 mmol) in THF (0.562 mL) cooled to −10° C. was added LHMDS (1M in THF) (1.123 mL, 1.123 mmol). The resulting suspension was warmed to rt and stirred for 15 minutes, after which time it was cooled back to −10° C. and 2-Methanesulfinyl-4'-methyl-[4,5']bipyrimidinyl-2'-ylamine (20) (70 mg, 0.281 mmol) was then added. The reaction mixture was again warmed to rt and stirred for 1.5 hours. The reaction was quenched by slow addition of saturated ammonium chloride and the volatiles evaporated. The mixture was then diluted with DCM, the layers separated, and the organic layer washed with brine, dried with sodium sulfate, and concentrated. The crude residue was purified by flash column chromatography with a gradient of 2-20% MeOH in DCM. The product was further purified by reverse phase HPLC with a gradient of 10-90% MeCN in water over 15 minutes, to give the desired product as a white solid (1.39 mg, 0.44%). 1H NMR (400 MHz, MeOD) δ ppm 2.57 (s, 3H) 7.13 (d, J=5.56 Hz, 1H) 7.84 (d, J=6.57 Hz, 2H) 8.30 (d, J=6.57 Hz, 2H) 8.50 (s, 1H) 8.57 (d, J=5.05 Hz, 1H). HRMS (ES+) for C14H13N7.H+ [MH+]: calcd, 280.1311; found, 280.1318. UV-LC: 100/100% UV purity at 214/254 nm; $t_R$=2.93 minutes over 7.75 minutes.

Example 22

Preparation of N2-(pyridin-4-yl)-4'-(trifluoromethyl)-4,5'-bipyrimidine-2,2'-diamine (22)

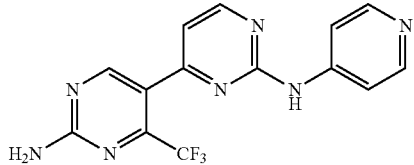
(22)

This compound was synthesized in an analogous manner to 21 utilizing benzyl 2,2,2-trifluoroacetate in step 1. To a solution of 4-aminopyridine (17.38 mg, 0.185 mmol) in THF (92 μl) cooled to −78° C. under nitrogen, LiHMDS (852 μl, 0.852 mmol) was added dropwise. The reaction mixture was warmed up to rt, then was stirred for 30 minutes. To the reaction mixture cooled back to −78° C., 2-(methylsulfinyl)-4'-(trifluoromethyl)-4,5'-bipyrimidin-2'-amine (14 mg, 0.046 mmol) was added, and the reaction mixture was warmed up to rt, then was stirred for 1 hour. The crude product was purified by reverse-phase HPLC [30-100% organic phase over 15 minutes] followed by Biotage™ silica gel chromatography [10 g SNAP column, 100% DCM to 12% MeOH/DCM] to obtain the desired product as a pale yellow solid (3.98 mg, 25% yield). 1H NMR (400 MHz, DMSO-$d_6$) δ ppm 7.13 (d, J=4.52 Hz, 1H) 7.67 (br. s., 2H) 7.77 (d, J=6.02 Hz, 2H) 8.34 (d, J=6.02 Hz, 2H) 8.56-8.74 (m, 2H) 10.23 (s, 1H). HRMS (ES+) for C14H10F3N7.H+ [MH+]: calcd, 334.1028; found, 334.1037. UV-LC: 97.31/100% UV purity at 214/254 nm; $t_R$=2.47 minutes over 7.75 minutes.

Example 13

Preparation of 4'-Benzyloxymethyl-N²-pyridin-4-yl-[4,5']bipyrimidinyl-2,2'-diamine (13)

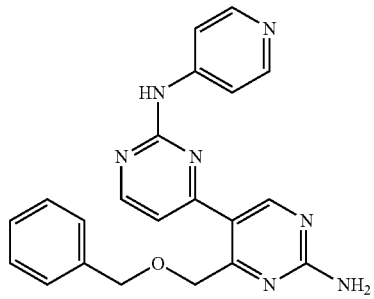

This compound was synthesized in an analogous manner to compound 21 utilizing 2-(benzyloxy)-N-methoxy-N-methylacetamide in step one. To a solution of 4-aminopyridine (79 mg, 0.836 mmol) in THF (1114 μl) cooled to −78° C. was added LHMDS (836 μl, 0.836 mmol). The reaction was stirred −78° C. for 15 minutes, after which time 4'-(benzyloxymethyl)-2-(methylsulfinyl)-4,5'-bipyrimidin-2'-amine (99 mg, 0.279 mmol) was added as a solution in THF (2 mL). The reaction was warmed to rt and stirred for 1 hour. The reaction was quenched by slow addition of saturated ammonium chloride and the reaction mixture was diluted with EtOAc. The residue was then partitioned between water and EtOAc. The organic layer was washed with brine, dried with sodium sulfate, and concentrated in vacuo. The crude product was purified by reverse-phase HPLC [30-100% organic phase over 15 minutes] followed by Biotage™ silica gel chromatography [10 g SNAP column, 100% DCM to 10% MeOH/DCM] to obtain the desired product as a pale yellow solid (94 mg, 88% yield). 1H NMR (400 MHz, DMSO-$d_6$) δ ppm 4.42 (s, 2H) 4.68 (s, 2H) 7.07-7.19 (m, 4H) 7.19-7.31 (m, 4H) 7.76 (d, J=6.57 Hz, 2H) 8.34 (d, J=6.06 Hz, 2H) 8.50-8.64 (m, 2H) 10.05 (s, 1H). HRMS (ES+) for C21H19N7O.H⁺ [MH⁺]: calculated, 386.1729; found, 386.1731. UV-LC: 100/100% UV purity at 214/254 nm; $t_R$=2.78 minutes over 7.75 minutes.

Example 23

Preparation of [2'-Amino-2-(pyridin-4-ylamino)-4,5'-bipyrimidin-4'-yl]methanol (23)

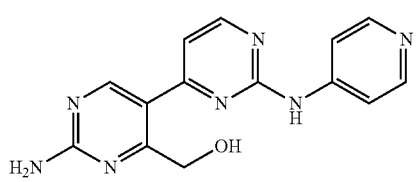

This compound was synthesized in an analogous manner to 21 utilizing benzyl 2-(tert-butyldiphenylsilyloxy)acetate in step one, and further TBDPS deprotection as the last step. To 4'-(tert-Butyl-diphenyl-silanyloxymethyl)-N²-pyridin-4-yl-[4,5']bipyrimidinyl-2,2'-diamine (150 mg, 0.281 mmol), TBAF (1N in THF) (562 μl, 0.562 mmol) was added. The reaction was stirred rt for 1 hour. Additional TBAF (1N in THF) (281 μl, 0.281 mmol) was added, and the reaction mixture was stirred for an additional 2 hours. The reaction was quenched by slow addition of saturated ammonium chloride and the volatiles were evaporated. The residue was then partitioned between water and EtOAc. The organic layer was washed with brine, dried with sodium sulfate, and concentrated. The crude product was purified by reverse-phase HPLC [100% aqueous phase to 60% organic phase over 15 minutes] to obtain the desired product as a slightly pale yellow solid (50 mg, 60% yield). 1H NMR (400 MHz, DMSO-$d_6$) ppm 4.66 (d, J=2.53 Hz, 2H) 5.04 (br. s., 1H) 7.18 (s, 2H) 7.30 (d, J=5.05 Hz, 1H) 7.77 (d, J=6.06 Hz, 2H) 8.36 (d, J=6.06 Hz, 2H) 8.57 (d, J=5.56 Hz, 1H) 8.63 (s, 1H) 10.03 (s, 1H). HRMS (ES+) for C14H13N7O.H⁺ [MH⁺]: calcd. 296.1260; found 296.1263. UV-LC: 100/100% UV purity at 214/254 nm; $t_R$=2.87 minutes over 7.75 minutes

Example 24

Preparation of 2-methyl-1-(2-(pyridin-4-ylamino)-4'-(trifluoromethyl)-4,5'-bipyrimidin-2'-ylamino)propan-2-ol (24)

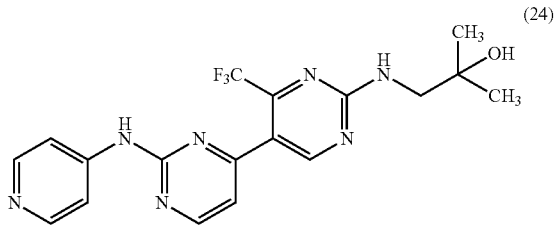 [SMILES: CC(C)(O)CNc1ncc(-c2ccnc(Nc3ccncc3)n2)c(C(F)(F)F)n1]

This compound was synthesized in an analogous manner to 22 utilizing 1-(2-hydroxy-2-methylpropyl)guanidine in step 3. To a solution of 4-aminopyridine (80 mg, 0.852 mmol) in THF (426 μl) cooled at −78° C. under nitrogen, LiHMDS (852 μl, 0.852 mmol) was added dropwise. The reaction mixture was warmed up to rt, then was stirred for 30 minutes. To the reaction mixture cooled back to −78° C., 2-methyl-1-(2-(methylsulfinyl)-4'-(trifluoromethyl)-4,5'-bipyrimidin-2'-ylamino)propan-2-ol (80 mg, 0.213 mmol) was added, and the reaction mixture was warmed up to rt, then was stirred for 1 hour. The crude product was purified by reverse-phase HPLC [30-100% organic phase over 15 minutes] followed by Biotage™ silica gel chromatography [10 g SNAP column, 100% DCM to 12% MeOH/DCM] to obtain the desired product as a pale yellow solid (25.7 mg, 30% yield). 1H NMR (400 MHz, DMSO-$d_6$) δ ppm 1.14 (s, 6H) 3.40 (br. s., 2H) 4.51 (s, 1H) 7.13 (d, J=5.05 Hz, 1H) 7.76 (s, 2H) 8.01 (br. s., 1H) 8.34 (d, J=5.56 Hz, 2H) 8.66 (d, J=4.93 Hz, 1H) 10.19 (s, 1H). HRMS (ES+) for C18H18F3N7O.H⁺ [MH⁺]: calcd, 406.1603; found, 406.1612. UV-LC: 100/100% UV purity at 214/254 nm; $t_R$=2.95 minutes over 7.75 minutes.

Example 25

Preparation of 4-(2'-(2-hydroxy-2-methylpropylamino)-4'-(trifluoromethyl)-4,5'-bipyrimidin-2-ylamino)benzonitrile (25)

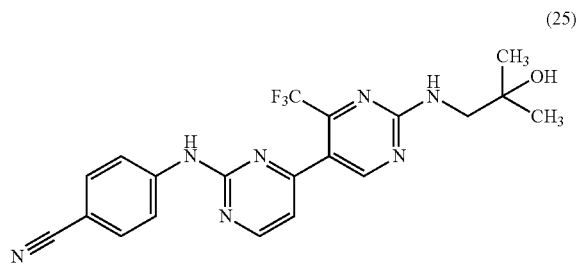 [SMILES: CC(C)(O)CNc1ncc(-c2ccnc(Nc3ccc(C#N)cc3)n2)c(C(F)(F)F)n1]

(25)

This compound was synthesized in an analogous manner to 24 utilizing 4-aminobenzonitrile in step 5. A pale yellow solid (14.5 mg, 13% yield). 1H NMR (400 MHz, DMSO-$d_6$) δ ppm 1.14 (s, 6H) 3.39 (dd, J=14.65, 5.56 Hz, 2H) 4.53 (d, J=19.20 Hz, 1H) 7.12 (d, J=5.05 Hz, 1H) 7.72 (d, J=9.09 Hz, 2H) 7.89-8.07 (m, 3H) 8.65 (d, J=5.05 Hz, 1H) 8.69 (br. s., 1H) 10.29 (s, 1H). HRMS (ES+) for C20H18F3N7O.H$^+$ [MH$^+$]: calcd, 430.1603; found, 430.1622. UV-LC: 100/98.09% UV purity at 214/254 nm; $t_R$=5.76 minutes over 7.75 minutes.

Example 27

Preparation of intermediate N'-{5-[(2E)-3-(dimethylamino)prop-2-enoyl]-4-methylpyrimidin-2-yl}-N,N-dimethylimidoformamide (27)

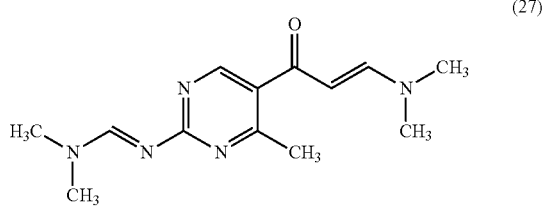

(27)

A solution of 5-acetyl-2-Amino-4-methypyrimidine (Alfa Aesar) (1.00 g, 6.62 mmol) in DMF-DMA (35.4 mL, 265 mmol) was heated at 120° C. for 18 hours. The reaction mixture was concentrated in vacuo, then was purified by Biotage™ silica gel chromatography [50 g SNAP column, 2-10% MeOH/DCM] to obtain a pale yellow solid as the desired product, which was dried over high vacuum for 1 hour (1.06 g, 61% yield). 1H NMR (400 MHz, DMSO-$d_6$) δ ppm 2.42 (s, 3H) 2.86 (br. s., 3H) 3.03 (s, 3H) 3.10 (br. s., 3H) 3.13 (s, 3H) 5.40 (d, J=12.63 Hz, 1H) 7.50 (d, J=12.63 Hz, 1H) 8.48 (s, 1H) 8.64 (s, 1H).

Preparation of intermediate N$^2$-(4-fluorophenyl)-4'-methyl-4,5'-bipyrimidinyl-2,2'-diamine (28)

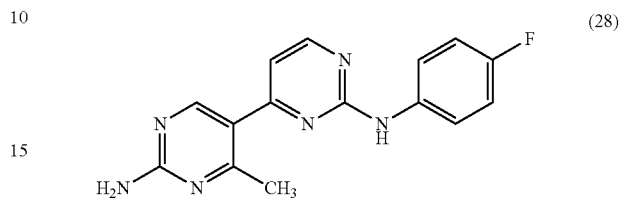

(28)

A solution of N'-{5-[(2E)-3-(dimethylamino)prop-2-enoyl]-4-methylpyrimidin-2-yl}-N,N-dimethylimidoformamide (27) (50 mg, 0.191 mmol), 1-(4-fluorophenyl)guanidine hydrochloride (102 mg, 0.383 mmol), and K$_2$CO$_3$ (106 mg, 0.765 mmol) in DMF (1018 µl) was heated at 120° C. for 2 d. The crude product was filtered through a syringe filter, then the crude product was purified by reverse-phase HPLC [30-100% organic phase over 15 minutes] to obtain ~80% pure desired product. The product was taken up in 10% MeOH/DCM, then was purified by Biotage™ silica gel chromatography [10 g SNAP column, 2-10% MeOH/DCM] and further purified by trituration with acetone and acetonitrile to obtain the desired product as a pale yellow solid (10.23 mg, 18% yield). 1H NMR (400 MHz, DMSO-$d_6$) δ ppm 2.47 (s, 3H) 6.93 (s, 2H) 7.02 (d, J=5.05 Hz, 1H) 7.12 (t, J=8.84 Hz, 2H) 7.77 (dd, J=9.35, 4.80 Hz, 2H) 8.44 (s, 1H) 8.46 (d, J=5.05 Hz, 1H) 9.61 (s, 1H). HRMS (ES+) for C15H13FN6.H$^+$ [MH$^+$]: calcd, 297.1264; found, 297.1274. UV-LC: 98.95/100% UV purity at 214/254 nm; $t_R$=4.30 minutes over 7.75 minutes.

Example 30

Preparation of intermediate 2-chloro-4,5'-bipyrimidin-2'-amine (30)

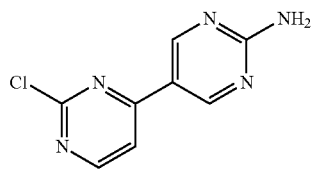

(30)

A suspension of 2-aminopyrimidinylboronic ester (500 mg, 2.262 mmol) (Maybridge), 2,4-Dichloropyrimidine (337 mg, 2.262 mmol), and sodium carbonate (479 mg, 4.52 mmol) in a 10:1 mixture of DME (9047 µl) and water (2262 µl) was degassed with nitrogen for 15 min, then PdCl$_2$(dppf). CH$_2$Cl$_2$ adduct (185 mg, 0.226 mmol) was added. The reaction mixture was heated at 85° C. for 78 hours. The reaction mixture was concentrated in vacuo, then the resulting bright red residue was taken up in EtOAc, filtered through a syringe filter, then concentrated in vacuo. The crude product was taken up in DCM, then was purified by Biotage™ silica gel chromatography [25 g SNAP column, 100% DCM to 20% MeOH/DCM] to obtain the desired product (110 mg, 23% yield). 1H NMR (400 MHz, DMSO-d$_6$) δ ppm 7.47 (s, 2H) 8.02 (d, J=5.56 Hz, 1H) 8.69 (d, J=5.56 Hz, 1H) 9.02 (s, 2H). MS (ES+): m/z=208.2 (100/80) [MH$^+$]. HPLC: t$_R$=0.75 minute over 3 minutes. Purity: 100% [HPLC (LC/MS) at 220 nm].

Preparation of N2-(4-fluorophenyl)-4,5'-bipyrimidine-2,2'-diamine (31)

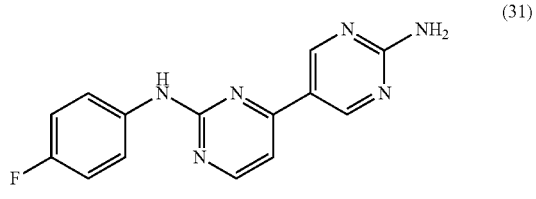 [SMILES: Nc1ncc(-c2ccnc(Nc3ccc(F)cc3)n2)cn1]

To a suspension of 2-chloro-4,5'-bipyrimidin-2'-amine (30) (110 mg, 0.530 mmol) in THF (5298 µl), 4-Fluoroaniline (100 µl, 1.060 mmol) was added. DMSO (1 mL) was added to dissolve the starting chloride, and the suspension was heated to 150° C. in the microwave for 2 hours. The crude reaction mixture was filtered through a syringe filter, then purified by reverse-phase HPLC [30-100% organic phase over 15 minutes] to obtain a reddish purple product. The product was triturated with acetone and acetonitrile, then filtered to obtain a slightly gray solid as the desired product (19 mg, 13% yield). 1H NMR (400 MHz, DMSO-d$_6$) δ ppm 7.15 (t, J=9.09 Hz, 2H) 7.22 (s, 2H) 7.31 (d, J=5.05 Hz, 1H) 7.79 (dd, J=9.09, 5.05 Hz, 2H) 8.44 (d, J=5.05 Hz, 1H) 8.99 (s, 2H) 9.59 (s, 1H). HRMS (ES+) for C14H11FN6.H$^+$ [MH$^+$]: calcd, 283.1107; found, 283.1108. UV-LC: 100/100% UV purity at 214/254 nm; t$_R$=1.07 minutes over 7.75 minutes.

Example 33

Preparation of intermediate 5-acetyl-2-(methylthio) pyrimidin-4(3H)-one (33)

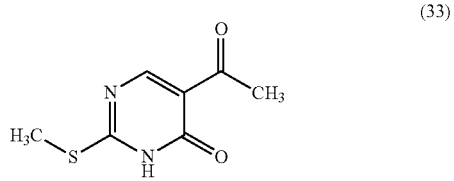

5-Acetyl-2-thioxo-2,3-dihydropyrimidin-4(1H)-one (Ryan Scientific) (2.3 g, 13.51 mmol) was dissolved in NaOH (20.27 mL, 20.27 mmol), then MeI (0.894 mL, 14.30 mmol) was added to the reaction mixture while stirring. The reaction mixture was heated at 40° C. for 1.5 hours. Additional MeI (0.894 mL, 14.30 mmol) was added and the reaction was allowed to stir at rt for 18 hours. The reaction mixture was cooled with an ice-water bath, acidified to pH 6 with concentrated HCl solution, then the resulting precipitate was filtered to obtain 1.72 g of the desired product (69% yield). 1H NMR (400 MHz, DMSO-d$_6$) δ ppm 2.49 (br. s., 6H) 8.35 (s, 1H) 13.40 (br. s., 1H). MS (ES+): m/z=185.1 (100) [MH$^+$]. HPLC: t$_R$=1.0 minute over 3 minutes. Purity: >90% [HPLC (LC/MS) at 220 nm].

Preparation of intermediate 4-(4-(2-(methylthio)-6-oxo-1,6-dihydropyrimidin-5-yl)pyrimidin-2-ylamino)benzonitrile (34)

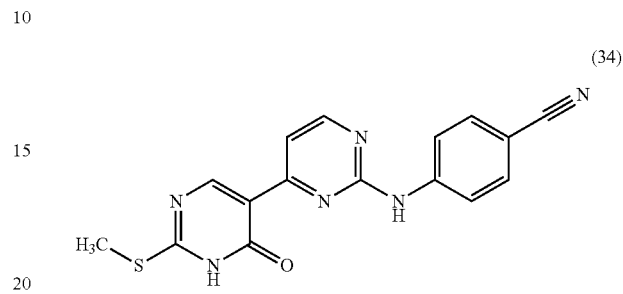

5-Acetyl-2-(methylthio)pyrimidin-4(3H)-one (33) (1.094 g, 5.94 mmol) was dissolved in 1-tert-butoxy-N,N,N',N'-tetramethylmethanediamine (12.26 mL, 59.4 mmol), then the reaction mixture was heated at 120° C. for 6 hours. The reaction mixture was concentrated in vacuo, and dried over high vacuum for 1 hour. The crude intermediate was taken up in DMF (31.6 mL), then 1-(4-cyanophenyl)guanidine (2.076 g, 8.91 mmol) and K$_2$CO$_3$ (4.10 g, 29.7 mmol) were added. The reaction mixture was heated at 120° C. for 48 hours. Additional 1-(4-cyanophenyl)guanidine (2.076 g, 8.91 mmol) and K$_2$CO$_3$ (3.69 g, 26.7 mmol) were added, and the reaction mixture was stirred at 120° C. for additional 18 hours. The reaction mixture was cooled to rt, then was slowly poured into an ice-cooled 1N HCl solution while stirring vigorously. The reaction mixture was neutralized with additional 1N HCl, then the reaction mixture was allowed to stir for an additional 30 minutes. The resulting precipitate was filtered, washed multiple times with DI water, 2-propanol, then diethyl ether. The resulting crude product was dried over high vacuum for 18 hours to obtain the desired product as a red/brown solid (940 mg, 47% yield). MS (ES+): m/z=337.2 (100) [MH$^+$]. HPLC: t$_R$=1.35 minutes over 3 minutes. Purity: 72% [HPLC (LC/MS) at 220 nm].

Example 35

Preparation of intermediate 4-(4'-chloro-2'-(methylthio)-4,5'-bipyrimidin-2-ylamino)benzonitrile (35)

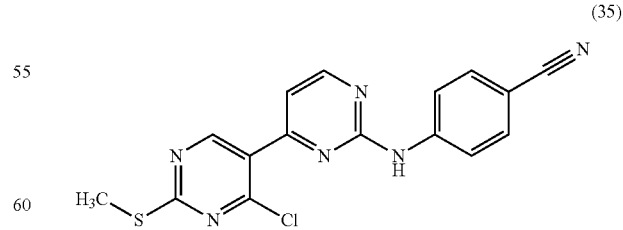

4-(4-(2-(Methylthio)-6-oxo-1,6-dihydropyrimidin-5-yl) pyrimidin-2-ylamino)benzonitrile (34) (700 mg, 2.081 mmol) was dissolved in POCl$_3$ (1940 µl, 20.81 mmol), then the reaction mixture was heated at 120° C. for 3 hours. The reaction mixture was cooled to rt, then was slowly poured into an ice-cooled saturated Na₂CO₃ solution while stirring vigorously. The reaction mixture was then adjusted to pH 7 with additional Na₂CO₃ solution. DCM was added to the mixture and the aqueous layer was extracted twice with DCM. The organic extracts were combined, washed with brine, dried over sodium sulfate, then concentrated in vacuo to obtain the desired product as a bright yellow solid (428 mg, 53% yield). 1H NMR (400 MHz, DMSO-d₆) δ ppm 2.62 (s, 3H) 7.39 (d, J=5.05 Hz, 1H) 7.74 (m, 2H) 8.00 (m, J=9.09 Hz, 2H) 8.69-8.80 (m, 1H) 8.93 (s, 1H) 10.42 (s, 1H). MS (ES+): m/z=355.3 (100) [MH⁺]. HPLC: $t_R$=1.57 minutes over 3 minutes. Purity: 91% [HPLC (LC/MS) at 220 nm].

Example 36

Preparation of 4-(4'-ethyl-2'-(methylthio)-4,5'-bipyrimidin-2-ylamino)benzonitrile (36a)

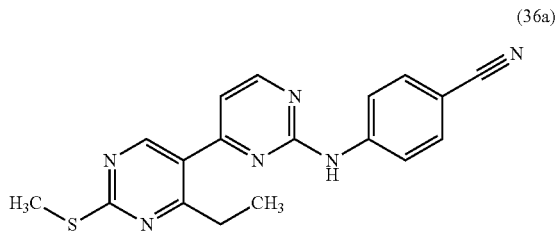 [SMILES: CCc1nc(SC)ncc1-c1ccnc(Nc2ccc(C#N)cc2)n1]

(36a)

4-(4'-Chloro-2'-(methylthio)-4,5'-bipyrimidin-2-ylamino) benzonitrile (35) (205 mg, 0.526 mmol) and ferric acetylacetonate (18.57 mg, 0.053 mmol) were dissolved in THF (3305 μl) and NMP (248 μl), then ethylmagnesium bromide (789 μl, 0.789 mmol) was added dropwise under nitrogen. The reaction was quenched with 1N HCl, then was extract with EtOAc. The organic extracts were combined, washed with brine, dried over sodium sulfate, then concentrated in vacuo. The crude product was dry-loaded onto silica gel and purified by Biotage™ silica gel chromatography [25 g SNAP column, 30% EtOAc/heptane to 100% EtOAc] to obtain 49 mg of the desired product (21%). 1H NMR (400 MHz, DMSO-d₆) δ ppm 1.19 (t, J=7.58 Hz, 3H) 2.59 (s, 3H) 2.95 (q, J=7.58 Hz, 2H) 7.25 (d, J=5.05 Hz, 1H) 7.68-7.78 (m, 2H) 7.95-8.03 (m, 2H) 8.67-8.75 (m, 2H) 10.33 (s, 1H). MS (ES+): m/z=349.5 [M+1] (100). HPLC: $t_R$=1.57 minutes over 3 minutes. Purity: 93% [HPLC (LC/MS) at 220 nm].

Preparation of 4-(4'-Isopropyl-2'-(methylthio)-4,5'-bipyrimidin-2-ylamino)benzonitrile (36b)

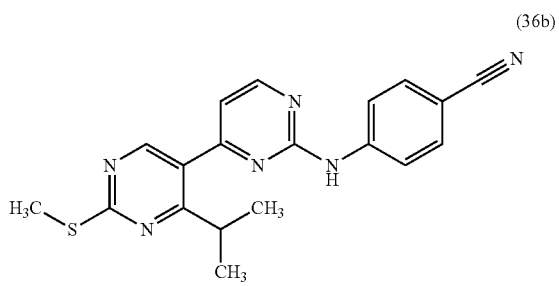 [SMILES: CSc1ncc(-c2ccnc(Nc3ccc(C#N)cc3)n2)c(C(C)C)n1]

(36b)

4-(4'-Chloro-2'-(methylthio)-4,5'-bipyrimidin-2-ylamino) benzonitrile (35) (125 mg, 0.352 mmol) and ferric acetylacetonate (12.44 mg, 0.035 mmol) were dissolved in THF (1791 μl) and NMP (134 μl), then isopropylmagnesium bromide (528 μl, 0.528 mmol) was added dropwise. According to LC/MS, approximately 40% conversion was observed. Additional isopropylmagnesium bromide (528 μl, 0.528 mmol) was added, and the reaction was stirred at rt for an additional 1 hour. The reaction was quenched with 1N HCl, then was extract with EtOAc. The organic extracts were combined, washed with brine, dried over sodium sulfate, then concentrated in vacuo. The crude product was dry-loaded onto silica gel, then was purified by Biotage™ silica gel chromatgraphy [25 g SNAP column, 30% EtOAc/heptane to 100% EtOAc] to obtain the desired product (51.1 mg, 40%). MS (ES+): m/z=363.3 [M+1] (100). HPLC: $t_R$=1.70 minutes over 3 minutes.

Example 37

Preparation of 4-(4'-ethyl-2'-(2-hydroxy-2-methylpropylamino)-4,5'-bipyrimidin-2-ylamino)benzonitrile (37a)

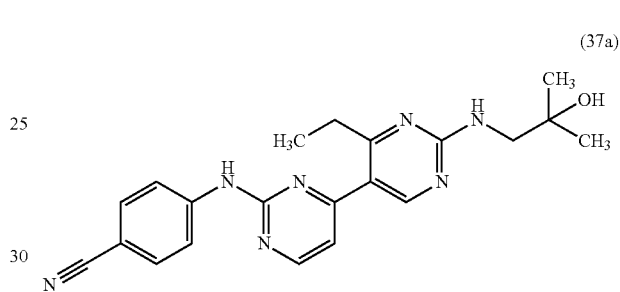

(37a)

4-(4'-Ethyl-2'-(methylthio)-4,5'-bipyrimidin-2-ylamino) benzonitrile (36a) (48.6 mg, 0.112 mmol) and 1-amino-2-propanol (29.8 mg, 0.335 mmol) were dissolved in THF (540 μl) and NMP (54.0 μl), then the reaction mixture was microwaved at 150° C. for 1 hour. Additional 1-amino-2-methylpropanol (99.8 mg, 1.12 mmol) was added, and the reaction mixture was microwaved further at 150° C. an additional 1 hour. Additional 1-amino-2-methylpropanol (99.8 mg, 1.12 mmol) was added, and the reaction mixture was microwaved further at 200° C. The crude reaction mixture was purified by reverse-phase HPLC [30-100% organic phase over 15 minutes using 0.1% TFA modifier] followed by Biotage™ silica gel chromatography [10 g SNAP column, 100% DCM to 10% MeOH/DCM] to obtain the desired product as a pale yellow solid (4.14 mg, 9% yield). 1H NMR (400 MHz, MeOD) δ ppm 1.20-1.27 (m, 9H) 2.94 (q, J=7.58 Hz, 2H) 3.51 (s, 2H) 4.55 (s, 1H) 7.04 (d, J=5.56 Hz, 1H) 7.62 (m, J=9.09 Hz, 2H) 7.96 (m, J=8.59 Hz, 2H) 8.44 (s, 1H) 8.52 (d, J=5.05 Hz, 1H). HRMS (ES+) for C21H23N7O.H⁺ [MH⁺]: calcd, 390.2042; found, 390.2023. UV-LC: 96.40/95.08% UV purity at 214/254 nm; $t_R$=5.31 minutes over 7.75 minutes.

4-(2'-(2-hydroxy-2-methylpropylamino)-4'-isopropyl-4,5'-bipyrimidin-2-ylamino)benzonitrile (37b)

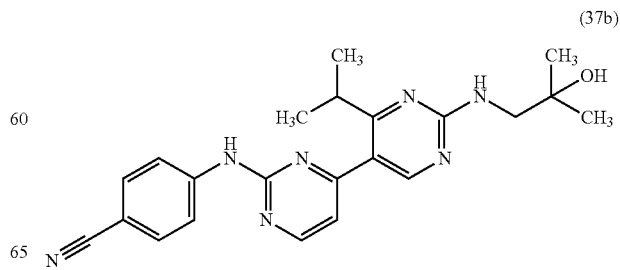

(37b)

4-(4'-Isopropyl-2'-(methylthio)-4,5'-bipyrimidin-2-ylamino)benzonitrile (36b) (51.1 mg, 0.141 mmol) and 1-amino-2-methylpropanol (126 mg, 1.410 mmol) were dissolved in THF (513 µl) and NMP (51.3 µl), then the reaction mixture was microwaved at 200° C. for 2 hours. The reaction was approximately 10% complete. Additional 1-amino-2-methylpropanol (126 mg, 1.410 mmol) was added, and the reaction mixture was microwaved at 200° C. for an additional 2 hours. The reaction mixture was microwaved at 200° C. for additional 3.5 hours. The crude reaction mixture was purified by reverse-phase HPLC [30-100% organic phase over 15 minutes using 0.1% TFA modified mobile phase] to obtain the desired product as a yellow foamy solid. 1H NMR (400 MHz, MeOD) δ ppm 1.27 (d, J=6.57 Hz, 6H) 1.30 (s, 6H) 3.43-3.65 (m, 2H) 3.71 (ddd, J=13.52, 6.69, 6.57 Hz, 1H) 7.08 (d, J=5.05 Hz, 1H) 7.63 (m, J=9.09 Hz, 2H) 7.95 (m, J=8.59 Hz, 2H) 8.45 (s, 1H) 8.61 (d, J=5.05 Hz, 1H). HRMS (ES+) for C22H25N7O.H$^+$ [MH$^+$]: calcd, 404.2199; found, 404.2201. UV-LC: 95.41/100% UV purity at 214/254 nm; $t_R$=5.73 minutes over 7.75 minutes.

Biological Activity

Vps34 KinaseGlo assay: 50 nL of compound dilutions were dispensed onto black 384-well low volume Non Binding Styrene (NBS) plates (Costar Cat. No. NBS#3676). L-a-phosphatidylinositol (PI), provided as 10 mg/mL solution in methanol (Avanti Polar Lipid; Cat. No. 840042C, Lot#LPI-274), was transferred into a glass tube and dried under nitrogen beam. It was then resuspended in 3% OctylGlucoside by vortexing and stored at 4° C. 5 µL of a mix of PI/OG with recombinant human Vps34 were added.

Kinase reactions were started by addition of 5 µl of ATP-mix containing in a final volume 10 µL 10 mM TRIS-HCl pH 7.5, 3 mM MgCl2, 50 mM NaCl, 0.05% CHAPS, 1 mM DTT and 1 µM ATP, and occurred at room temperature. Reactions were stopped with 10 µl of KinaseGlo and plates were read 10 minutes later in a Synergy2 reader using an integration time of 0.1 seconds per well. The luminescence-based ATP detection reagent KinaseGlo was obtained from Promega, (Cat. No. V6714, Lot No. 236161) through Catalys, Wallisellen, Switzerland.

IC50 values of the percentage inhibition of each compound at 8 concentrations (usually 10, 3.0, 1.0, 0.3, 0.1, 0.030, 0.010 and 0.003 µM) n=2 were derived by fitting a sigmoidal dose response curve to a plot of assay readout over inhibitor concentration.

| Example | Vps34 IC50 (µM) |
|---|---|
| 6a | 1.00 |
| 6b | 0.264 |
| 6c | 0.775 |
| 6d | 0.728 |
| 6e | 0.111 |
| 6f | 4.00 |
| 10a | 0.0175 |
| 10b | 0.02 |
| 10c | 0.0755 |
| 10d | 0.072 |
| 10e | 0.0785 |
| 10f | 0.0455 |
| 10g | 0.2365 |
| 10h | 0.2575 |
| 10i | 0.035 |
| 10j | 0.029 |
| 10k | 0.2755 |
| 10l | 0.0805 |
| 10m | 0.0115 |
| 10n | 0.031 |
| 10o | 0.0315 |
| 10p | 0.2105 |
| 10q | 0.053 |
| 10r | 0.085 |
| 10s | 0.0515 |
| 10t | 0.015 |
| 10u | 0.0905 |
| 10v | 0.214 |
| 11 | 0.1065 |
| 12a | 0.0345 |
| 12b | 0.5695 |
| 12c | 0.0455 |
| 13 | 0.007 |
| 14a | 0.115 |
| 14b | 0.286 |
| 14c | 0.037 |
| 14d | 0.133 |
| 14e | 1.10 |
| 14f | 0.722 |
| 14g | 0.398 |
| 14h | 1.36 |
| 14i | 0.348 |
| 14j | 0.411 |
| 14k | 0.857 |
| 14l | 0.048 |
| 14m | 0.119 |
| 14n | 0.439 |
| 14o | 0.374 |
| 14p* | 5.17 |
| 14q* | 0.862 |
| 14r* | 1.54 |
| 14s* | 7.13 |
| 15a | 0.577 |
| 15b | 0.199 |
| 15c | 6.62 |
| 15d | 1.50 |
| 15e | 0.196 |
| 15f | Not determined |
| 15g | 2.23 |
| 15h | 0.048 |
| 15i | 0.924 |
| 15j | 0.053 |
| 15k | 0.781 |
| 15l | 0.025 |
| 15m | 0.101 |
| 15n | 0.062 |
| 15o | 0.057 |
| 15p | 0.122 |
| 15q | 1.29 |
| 15r | Not determined |
| 15s | 1.66 |
| 15t | 0.187 |
| 15u | 0.104 |
| 15v | 0.193 |
| 15w | 0.036 |
| 15x | 0.027 |
| 15y | 0.231 |
| 16a | 0.004 |
| 16b | 0.025 |
| 16c | 0.150 |
| 16d | 0.026 |
| 16e | 0.105 |
| 16f | 0.138 |
| 16g | 0.872 |
| 21 | 0.02225 |
| 22 | 0.031 |
| 23 | 0.1305 |
| 24 | 0.096 |
| 25 | 0.117 |
| 37a | 0.031 |
| 37b | Not determined |

Thus while there have been described what are presently believed to be preferred embodiments of the invention, those skilled in the art will realize that changes and modifications may be made thereto without departing from the spirit of the invention, and it is intended to claim all such changes and modifications as fall within the true scope of the invention.

What is claimed is:

1. A compound of formula I:

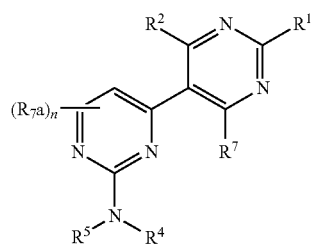

or a pharmaceutically acceptable salt thereof, wherein $R^1$ is $C_{1-6}$alkyl, $NR^3R^6$, $C_{1-6}$alkoxy, or —S—$C_{1-6}$alkyl;

$R^2$ is $C_{1-6}$alkyl, $C_{2-6}$alkenyl, $C_{2-6}$alkynyl, a $C_{6-14}$aryl group, a $C_{3-14}$cycloalkyl group, a 5 to –14 membered heteroaryl containing 1 to 3 heteroatoms each independently selected from N, O, and S, $C_{1-6}$alkoxy, $C_{2-6}$-alkenyloxy, $C_{2-6}$-alkynyloxy, $C_{1-6}$alkyl-O—$R^{27}$, $C_{1-6}$alkyl-$C_{3-14}$cycloalkyl, $C_{1-6}$alkyl-O—$C_{0-6}$alkyl-$C_{6-14}$ aryl, $C_{1-6}$alkyl-O—$SiR^8R^9R^{10}$, halogen, or $C_{1-6}$haloalkyl, wherein $R^2$ may be unsubstituted or substituted with OH, C1-6alkoxy, or halogen;

$R^4$ and $R^5$ are independently H, $C_{1-6}$alkyl, $C_{2-6}$alkenyl, $C_{2-6}$alkynyl, a $C_{6-14}$aryl group, a $C_{3-14}$cycloalkyl group, a 3-14 membered cycloheteroalkyl group, a 5-14 membered heteroaryl group, $C_{1-6}$alkoxy, OH, $C_{1-6}$alkyl$NR^{11}R^{12}$, $C_{1-6}$alkyl-O—$R^{13}$, $C_{1-6}$alkyl-5-14membered heteroaryl group, or C(O)—$C_{1-6}$alkyl, wherein said $C_{1-6}$alkyl, $C_{2-6}$alkenyl, $C_{2-6}$alkynyl, $C_{6-14}$aryl group, $C_{3-14}$cycloalkyl group, 3-14 membered cycloheteroalkyl group, 5-14 membered heteroaryl group, $C_{1-6}$alkoxy, $C_{1-6}$alkyl-$NR^{11}R^{12}$, $C_{1-6}$alkyl$OR^{13}$, $C_{1-6}$alkyl-5-14 membered heteroaryl group, or C(O)—$C_{1-6}$alkyl may be optionally substituted by one or more from the group of halogen, a 5-14 membered heteroaryl group, OH, $C_{1-6}$alkyl, $C_{1-6}$haloalkyl, $C_{1-6}$alkyl$OR^{27}$, $C_{1-6}$alkoxy, $NR^{14}R^{15}$, $CONR^{16}R^{17}$, $NR^{18}COR^{19}$, $NR^{20}COOR^{21}$, $COR^{22}$, $COOR^{23}$, —CN, $SO_2R^{26}$, or $NR^{24}SO_2R^{25}$;

$R^3$ and $R^6$ are independently H, $C_{1-6}$alkyl, $C_{1-6}$alkyl-aryl, $C_{1-6}$alkoxy, a $C_{3-14}$cycloalkyl group, a 3-14 membered cycloheteroalkyl group, a $C_{6-14}$aryl group, a 5-14 membered heteroaryl group, or $C_{1-6}$alkyl-O—$R^8$, wherein $C_{1-6}$alkyl, $C_{1-6}$alkyl-aryl, $C_{1-6}$alkoxy, a $C_{3-14}$cycloalkyl group, a 3-14 membered cycloheteroalkyl group, a $C_{6-14}$aryl group, a 5-14 membered heteroaryl group, or $C_{1-6}$alkyl-O—$R^8$, may be substituted by one of more of $C_{1-6}$alkyl, or OH;

$R^{11}$ and $R^{12}$ are the same or different, and independently are selected from hydrogen, $C_{1-6}$alkyl, a $C_{3-8}$cycloalkyl group, a $C_{6-14}$ aryl group, a 5-14 membered heteroaryl group, and a 3-14 membered cycloheteroalkyl group, or $NR^{11}R^{12}$ forms a non-aromatic four to seven membered ring optionally containing a second heteroatom selected from O, N and S, and optionally substituted by one or more substituents $R^{28}$;

$R^7$ and $R^{7a}$ are independently H or $C_{1-6}$alkyl n is 0, 1, or 2; and $R^8$, $R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$, and $R^{28}$ are independently H, $C_{1-6}$alkyl, $C_{2-6}$alkenyl, $C_{2-6}$alkynyl, a $C_{6-14}$ aryl group, A $C_{3-14}$ cycloalkyl group, a 3-14 membered cycloheteroalkyl group, or a 5-14 membered heteroaryl group.

2. The compound of formula (I) according to claim 1, wherein $R^1$ is $C_{1-6}$alkyl, $NR^3R^6$, or $C_{1-6}$alkoxy, and $R^3$ and $R^6$ are independently H, $C_{1-6}$alkyl, $C_{1-6}$alkyl-aryl, a $C_{3-14}$cycloalkyl group, $C_{1-6}$alkylOH, $C_{1-6}$alkyl$OC_{1-6}$alkyl, or a 3-14 membered cycloheteroalkyl group.

3. The compound of formula (I) according to claim 1 wherein $R^1$ is methyl, ethyl, propyl, methoxy, ethoxy, methylphenyl, $NH_2$, NH-pentyl-OH, NHbutyl, $NHCH_3$, or NHisopropyl.

4. The compound of formula (I) according to claim 1 wherein $R^1$ is $NH_2$, NH-pentyl-OH, NHbutyl, $NHCH_3$, or NHisopropyl.

5. The compound of formula (I) according to claim 1 wherein $R^2$ is $C_{1-6}$alkyl, a $C_{3-14}$cycloalkyl group, or $C_{1-6}$alkyl-$C_{3-14}$cycloalkyl.

6. The compound of formula (I) according to claim 1 wherein $R^2$ is methyl, ethyl, propyl, phenyl, cyclopropyl, cyclopentyl, cyclohexyl, methoxy, —$CH_2$—O—$CH_3$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, —$CH_2CH_2$-cyclohexyl, or —$CH_2$—O—$CH_2$-phenyl.

7. The compound of formula (I) according to claim 1 wherein $R^2$ is —$CH_2$-cyclopropyl.

8. The compound of formula (I) according to claim 1 wherein $R^4$ and $R^5$ are independently H, a $C_{6-14}$aryl group, $C_{3-14}$cycloalkyl group, a 3-14 membered cycloheteroalkyl group, or a 5-14 membered heteroaryl group wherein said $C_{6-14}$aryl group, $C_{3-14}$cycloalkyl group, 3-14 membered cycloheteroalkyl group, or 5-14 membered heteroaryl group, is optionally mono- or di-substituted by one or more of halogen, OH, $C_{1-6}$alkyl, $C_{1-6}$haloalkyl, $C_{1-6}$alkylOH, $C_{1-6}$alkoxy, $NR^{14}R^{15}$, $CONR^{16}R^{12}$, $NR^{18}COR^{19}$, $NR^{20}COOR^{21}$, $COR^{22}$, $COOR^{23}$, or $NR^{24}SO_2R^{25}$.

9. The compound of formula (I) according to claim 1 where one of $R^4$ or $R^5$ is H, and the other is methyl, ethyl, propyl, phenyl, cyclopentyl, cyclohexyl, piperidinyl, piperazinyl, pyrrolidinyl, tetrahydropyranyl, pyridinyl, pyrimidinyl, or pyridazinyl; each of which may be unsubstituted or substituted with one or more of halogen, a 5-14 membered heteroaryl group, OH, $C_{1-6}$alkyl, $C_{1-6}$haloalkyl, $C_{1-6}$alkyl$OR^{22}$, $C_{1-6}$alkoxy, $NR^{14}R^{15}$, $CONR^{16}R^{17}$, $NR^{18}COR^{19}$, $NR^{20}COOR^{21}$, $COR^{22}$, $COOR^{23}$, —CN, $SO_2R^{26}$, —O—, or $NR^{24}SO_2R^{25}$.

10. The compound of formula (I) according to claim 1 where one of $R^4$ and $R^5$ is H, and the other is phenyl or pyridinyl, each of which may be unsubstituted or substituted with one or more of F, Cl, OH, methyl, ethyl, CN, or $CF_3$.

11. The compound of formula (I) according to claim 1 where $R^2$ is H and n is 0.

12. A compound of Formula II,

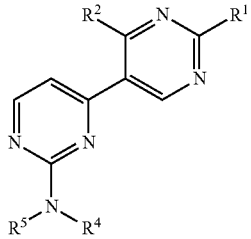

or a pharmaceutically acceptable salt thereof, wherein
$R^1$ is $(C_1-C_6)$alkyl, —$OCH_3$, —$NH_2$, —$NH(C_1-C_6)$alkyl, —$NHCH_2$(phenyl), —$NHCH_2CH_2OH$, —$NHCH_2CH(OH)CH_3$, —$NHCH(CH_3)CH_2OH$, —$NHCH_2CH(CH_3)_2OH$, —$NHCH_2CH_2OCH_3$, —$NH(C_3-C_6)$cycloalkyl, phenethylamino-, tetrahydropyranylamino-, or —$SCH_3$;
$R^2$ is $(C_1-C_6)$alkyl, —$CF_3$, —$CH_2$(cyclopropyl), —$CH_2OH$, or —$CH_2OCH_2$(phenyl);
$R^4$ is H; and
$R^5$ is
(i) —$(CH_2)_n$—$R^{5a}$, where n is 0, 1 or 2 and $R^{5a}$ is pyridinyl, 6-methoxypyridin-3-yl, furanyl, imidazolyl, isoxazolyl, thiazolyl, thiadiazolyl, quinolinyl, 1H-indolyl, benzo[d][1,3]dioxolyl, morpholinyl, tetrahydropyranyl, or piperidinyl, where said chemical moiety is optionally substituted with a methyl or halo; or
(ii) $(C_1-C_6)$alkyl, $(C_3-C_6)$cycloalkyl, or phenyl, wherein said $(C_1-C_6)$alkyl, said $(C_3-C_6)$cycloalkyl, and said phenyl are optionally substituted with one to two substituents each independently selected from F, Cl, —$CH_3$, —$CN$, —$OH$, —$OCH_3$, —$NHC(O)$—$(C_1-C_4)$alkyl, —$NH_2$, —$N(CH_3)_2$, —$NHSO_2CH_3$, —$C(O)CH_3$, —$C(O)OH$, or —$SO_2CH_3$.

13. The compound according to claim 12 wherein n is 0.

14. The compound according to claim 1 which is 1-(4'-(cyclopropylmethyl)-2-(pyridin-4-ylamino)-4,5'-bipyrimidin-2'-ylamino)-2-methylpropan-2-ol having the following formula:

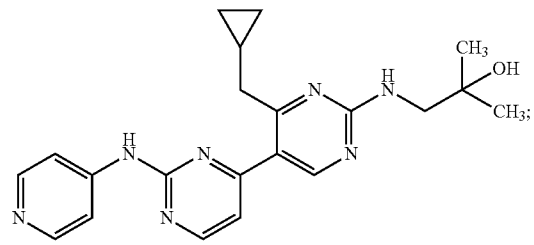 [SMILES: CC(C)(O)CNc1ncc(-c2ccnc(Nc3ccncc3)n2)c(CC2CC2)n1]

or a pharmaceutically acceptable salt thereof.

15. The compound according to claim 1 which is 4'-Cyclopropylmethyl-$N^2$-pyridin-4-yl-[4,5']bipyrimidinyl-2,2'-diamine having the following formula:

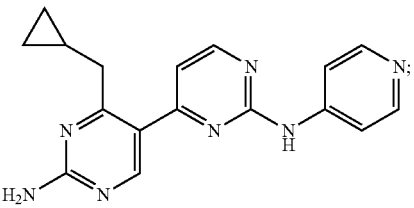 [SMILES: Nc1ncc(-c2ccnc(Nc3ccncc3)n2)c(CC2CC2)n1]

or a pharmaceutically acceptable salt thereof.

16. The compound according to claim 1 which is 4'-Benzyloxymethyl-$N^2$-pyridin-4-yl-[4,5']bipyrimidinyl-2,2'-diamine having the following formula:

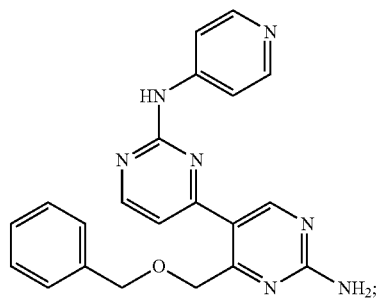 [SMILES: Nc1ncc(-c2ccnc(Nc3ccncc3)n2)c(COCc2ccccc2)n1]

or a pharmaceutically acceptable salt thereof.

17. The compound according to claim 1 which is N2-(pyridin-4-yl)-4'-(trifluoromethyl)-4,5'-bipyrimidine-2,2'-diamine having the following formula:

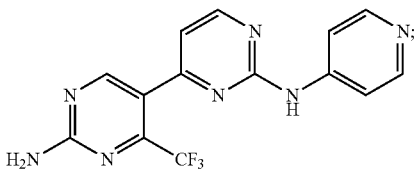 [SMILES: Nc1ncc(-c2ccnc(Nc3ccncc3)n2)c(C(F)(F)F)n1]

or a pharmaceutically acceptable salt thereof.

18. A pharmaceutical composition comprising a compound of formula I according to claim 1 and a pharmaceutically acceptable carrier or excipient.

19. A pharmaceutical composition comprising a compound of formula I according to claim 1 in combination with a second active agent, and a pharmaceutically acceptable carrier or excipient.

* * * * *